US008980281B2

(12) United States Patent
Hsiao et al.

(10) Patent No.: US 8,980,281 B2
(45) Date of Patent: Mar. 17, 2015

(54) HIGH-YIELD TRANSGENIC MAMMALIAN EXPRESSION SYSTEM FOR GENERATING VIRUS-LIKE PARTICLES

(75) Inventors: Pei-Wen Hsiao, Taipei (TW); Chia-Ying Wu, Kaohsiung (TW); Yi-Chun Yeh, Taipei (TW)

(73) Assignee: Academia Sinica, Taipei (TW)

( * ) Notice: Subject to any disclaimer, the term of this patent is extended or adjusted under 35 U.S.C. 154(b) by 734 days.

(21) Appl. No.: 12/704,928

(22) Filed: Feb. 12, 2010

(65) Prior Publication Data

US 2010/0166769 A1   Jul. 1, 2010

Related U.S. Application Data

(63) Continuation-in-part of application No. 11/515,843, filed on Sep. 5, 2006, now abandoned.

(51) Int. Cl.
| A61K 39/42 | (2006.01) |
| C12P 21/00 | (2006.01) |
| C12N 9/26 | (2006.01) |
| C07K 16/08 | (2006.01) |
| C12N 5/07 | (2010.01) |
| C12N 15/00 | (2006.01) |
| A61P 31/16 | (2006.01) |
| A61K 39/215 | (2006.01) |
| A61K 39/145 | (2006.01) |
| C07K 14/005 | (2006.01) |
| A61K 39/00 | (2006.01) |

(52) U.S. Cl.
CPC ............ *A61K 39/215* (2013.01); *A61K 39/145* (2013.01); *C07K 14/005* (2013.01); *A61K 2039/5258* (2013.01); *C12N 2760/16122* (2013.01); *C12N 2760/16123* (2013.01); *C12N 2760/16134* (2013.01); *C12N 2770/20022* (2013.01); *C12N 2770/20023* (2013.01); *C12N 2830/006* (2013.01)
USPC ........ 424/209.1; 435/364; 435/69.1; 435/455

(58) Field of Classification Search
CPC ............. A61K 39/145; A61K 39/215; A61K 2039/5258; C12N 2760/1622; C12N 2760/16123; C12N 2760/16134; C12N 2770/20022; C12N 2770/20023; C12N 2830/006; C07K 14/005
See application file for complete search history.

(56) References Cited

U.S. PATENT DOCUMENTS

| 5,820,870 A | 10/1998 | Joyce et al. |
| 2005/0002953 A1 | 1/2005 | Herold |
| 2005/0130127 A1 | 6/2005 | Rottier et al. |
| 2005/0186575 A1 | 8/2005 | Rottier et al. |
| 2007/0184526 A1 | 8/2007 | Smith et al. |
| 2009/0022762 A1 | 1/2009 | Galarza et al. |

FOREIGN PATENT DOCUMENTS

| WO | 2005035556 A2 | 4/2005 |
| WO | 2005063801 A2 | 7/2005 |

OTHER PUBLICATIONS

Latham et al. Formation of Wild-Type and Chimeric Influenza Virus-Like Particles following Simultaneous Expression of Only Four Structural Proteins. Journal of Virology 2001, vol. 75, No. 13, pp. 6154-6165.*
Webby et al. Responsiveness to a pandemic alert: use of reverse genetics for rapid development of influenza vaccines. Lancet 2004; vol. 363, pp. 1099-1103.*
Yao et al. Tetracycline Repressor, tetR, rather than the t e t R—Mammalian Cell Transcription Factor Fusion Derivatives, Regulates Inducible Gene Expression in Mammalian Cells. Human Gene Therapy 1998, vol. 9, pp. 1939-1950.*
Kuiken, T. et al., "Newly discovered coronavirus as the primary cause of severe acute respiratory syndrome", The Lancet, vol. 362, pp. 263-270, (2003).
Lin, Y. et al., "Probing the structure of the SARS coronavirus using scanning electron microscopy", Antivir Ther., vol. 9, pp. 287-289, (2004).
Ksiazek, T.G. et al., "A novel coronavirus associated with severe acute respiratory syndrome" New England Journal of Medicine, vol. 348, pp. 1953-1966, (2003).
McGuigan, L.D., et al., "Recombinant-expressed virus-like particle pseudotypes as an approach to vaccine development", Vaccine, vol. 11, pp. 675-678, (1993).
Vennema, H. et al., "Nucleocapsid-independent assembly of coronavirus-like particles by co-expression of viral envelope protein genes", the Embo Journal, vol. 15, pp. 2020-2028, (1996).
Godeke, G.J. et al., "Assembly of spikes into coronavirus particles is mediated by the carboxy-terminal domain of the spike protein", Journal of Virology, vol. 74, pp. 1566-1571, (2000).
Ho, Y. et al., "Assembly of human severe acute respiratory syndrome coronavirus-like particles", Biochemical and Biophysical Research Communications, vol. 318, pp. 833-838, (2004).
Mortola, E. et al., "Efficient assembly and release of SARS coronavirus-like particles by a heterologous expression system", Federation of European Biochemical Societies Letters, vol. 576, pp. 174-178, (2004).
Wu, H.S. et al., "Early detection of antibodies against various structural proteins of the SARS-associated coronavirus in SARS patients", J Biomed Sci vol. 11, pp. 117-126, (2004).
Chang, M.S. et al., "Antibody detection of SARS-Co V spike and nucleocapsid protein" Biochemical and Biophysical Research Communications, vol. 314, pp. 931-936, (2004).

(Continued)

*Primary Examiner* — Louise Humphrey
(74) *Attorney, Agent, or Firm* — Panitch Schwarze Belisario & Nadel LLP

(57) ABSTRACT

Virus-like particles (VLPs) of mammalian-hosted viruses, such as SARS-CoV and influenza viruses, have been recombinantly produced from Vero cells. The VLPs closely emulate the exterior of authentic virus particles and are highly immunogenic. They can elicit not only humoral but also cellular immune responses in a mammal. Compositions and methods related to the VLPs are also described.

20 Claims, 14 Drawing Sheets
(9 of 14 Drawing Sheet(s) Filed in Color)

(56) References Cited

OTHER PUBLICATIONS

Strategic and operational review update [online]. Select Vaccines Limited, Melbourne, Australia, Dec. 15, 2008 [retrieved on Apr. 21, 2009]. Retrieved from the internet <URL: http://media.wotnews.com/au/asxann/00913363.pdf>.

Lindenburg et al. Long-term follow-up: no effect of therapeutic vaccination with HIV-1 p17/p24; Ty virus-like particles on HIV-1 disease progression. Vaccine 2002, vol. 20, pp. 2343-2347.

Navas-Martin et al. Coronavirus replication and pathogenesis: Implications for the recent outbreak of severe acute respiratory syndrome (SARS), and the challenge for vaccine development. Journal of neuroVirology 2004, vol. 10, pp. 75-85.

Letvin. Progress toward an HIV vaccine. Annual Review of Medicine 2005, vol. 56, p. 213-223.

Tonini et al. Current approaches to developing a preventative HIV vaccine. Current Opinion in Invenstigational Drugs 2005, vol. 6, No. 2, p. 155-162.

Puls et al. Therapeutic vaccination against HIV: current progress and future possibilities. Clinical Science 2006, vol. 110, p. 59-71.

Encke et al. Development of a heterologous, multigenotype vaccine against hepatitis C virus infection. European Journal of Clinical Investigation 2007, vol. 37, pp. 396-406.

Abrignani et al. Perspectives for a vaccine against hepatitis C virus. Journal of Hepatology 1999, vol. 31, Supplement 1, pp. 259-263.

Yee et al. Prospects for Gene Therapy Using HIV-based Vectors. Somatic Cell and Molecular Genetics 2001, vol. 26, No. 1, pp. 159-174.

Jiang et al. SARS Vaccine Development. Emerging Infectious Diseases 2005, vol. 11, No. 7, pp. 1016-1020.

Zhi et al. SARS Vaccine: Progress and Challenge. Cellular & Molecular Immunology 2005, vol. 2, No. 2, pp. 101-105.

Chen et al.; Influenza Virus Hemagglutinin and Neuraminidase, but Not the Matrix Protein, Are Required for Assembly and Budding of Plasmid-Derived Virus-Like Particles; Journal of Virology; vol. 81, No. 13; Jul. 2007,pp. 7111-7123.

Noad et al.; Virus-like Particles as Immunogens; Trends in Microbiology; vol. 11, No. 9; Sep. 2003; pp. 438-444.

Shaw et al.; Cellular Proteins in Influenza Virus Particles; PLoS Pathogens; vol. 4, Issue 6; Jun. 2008; pp. 1-13.

Kang et al.; "Influenza Vaccines Based on Virus-Like Particles"; Virus Res. Aug. 2009; 143(2): 140-146. doi:10.1016/j.virusres.2009.04.005.

Margine et al.; "Residual Baculovirus in Insect Cell-Derived Influenza Virus-Like Particle Preparations Enchances Immunogenicity"; PLoS One, Dec. 2012, vol. 7, Issue 12, e51559.

Wu et al.; "Mammalian Expression of Virus-Like Particles for Advanced Mimicry of AUthentic Influenza Virus"; PLoS One, Mar. 2010, vol. 5, Issue 3, e9784.

Wu et al.; "A VLP Vaccine Induces Broad-Spectrum Cross Protective Antibody Immunity Against H5N1 and H1N1 Subtypes of Influenza A Virus"; PLoS One, Aug. 2012, vol. 7, Issue 9, e42363.

Quan et al.; "Virus-Like Particle Vaccine Induces Protective Immunity Against Homologous and Heterologous Strains of Influenza Virus"; J. Virol. 2007 81(7):3514. DOI. 10.1128/JVI.02052-06., Published Ahead of Print Jan. 24, 2007.

\* cited by examiner

*Fig. 1A*
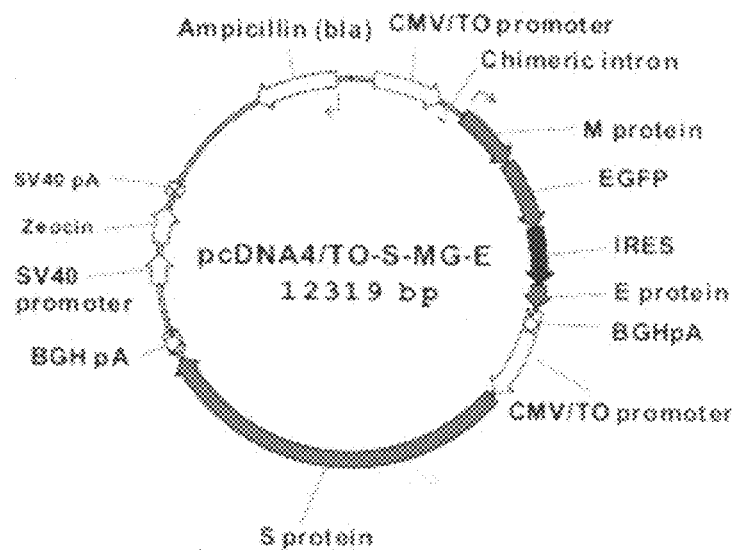
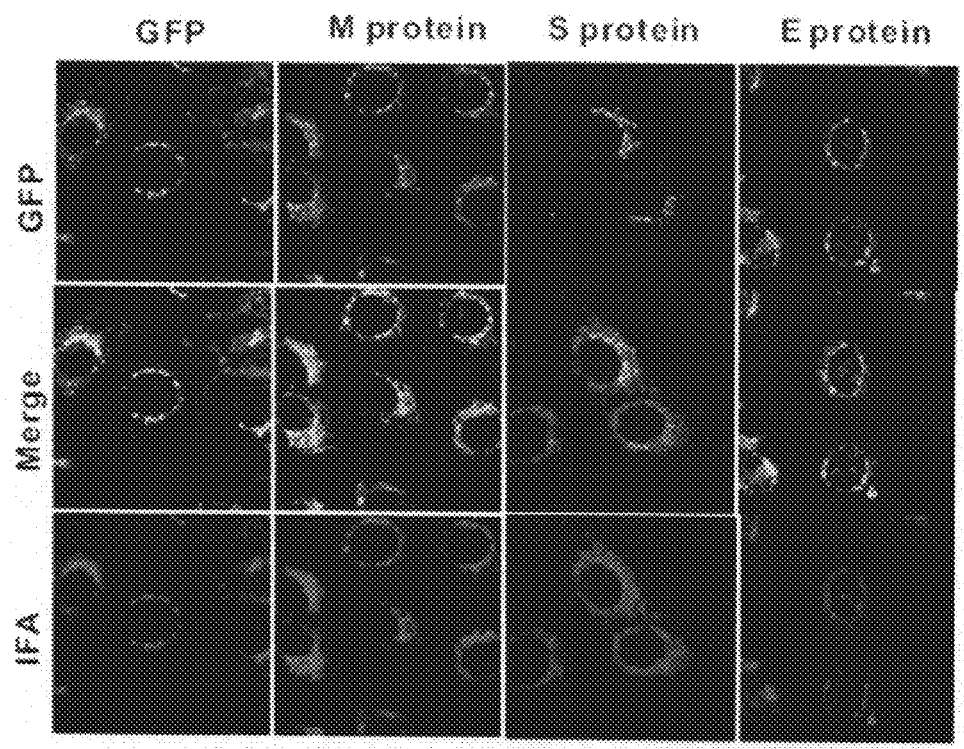
*Fig. 1B*

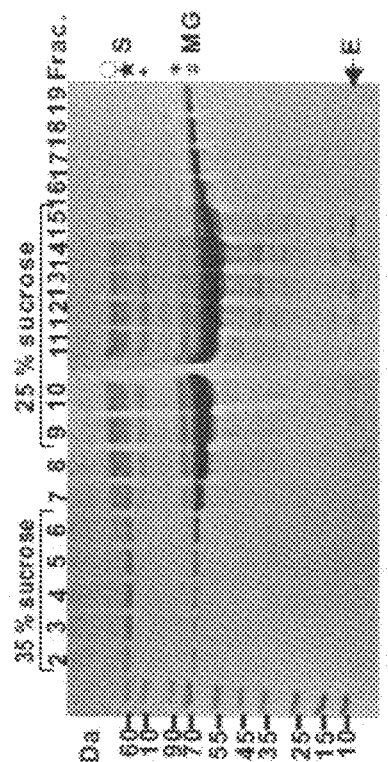
Fig. 2B
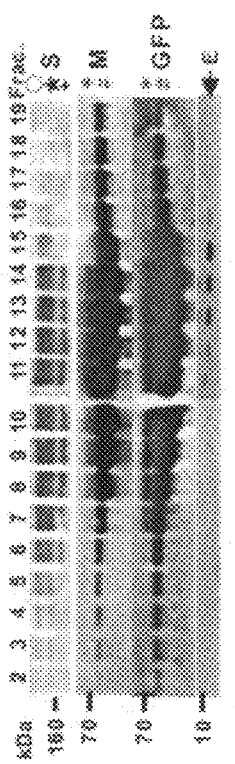
Fig. 2C
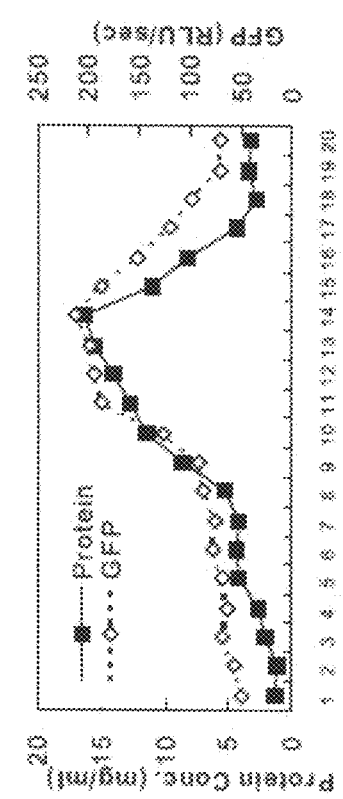
Fig. 2A
Fig. 2D

Figure 5
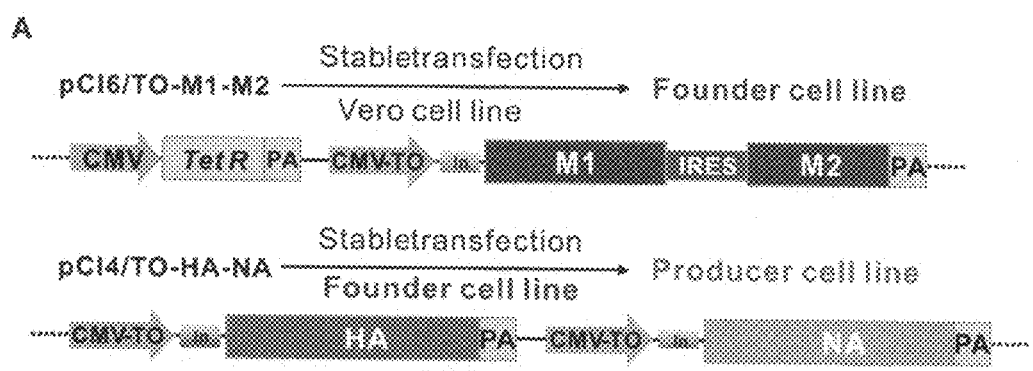
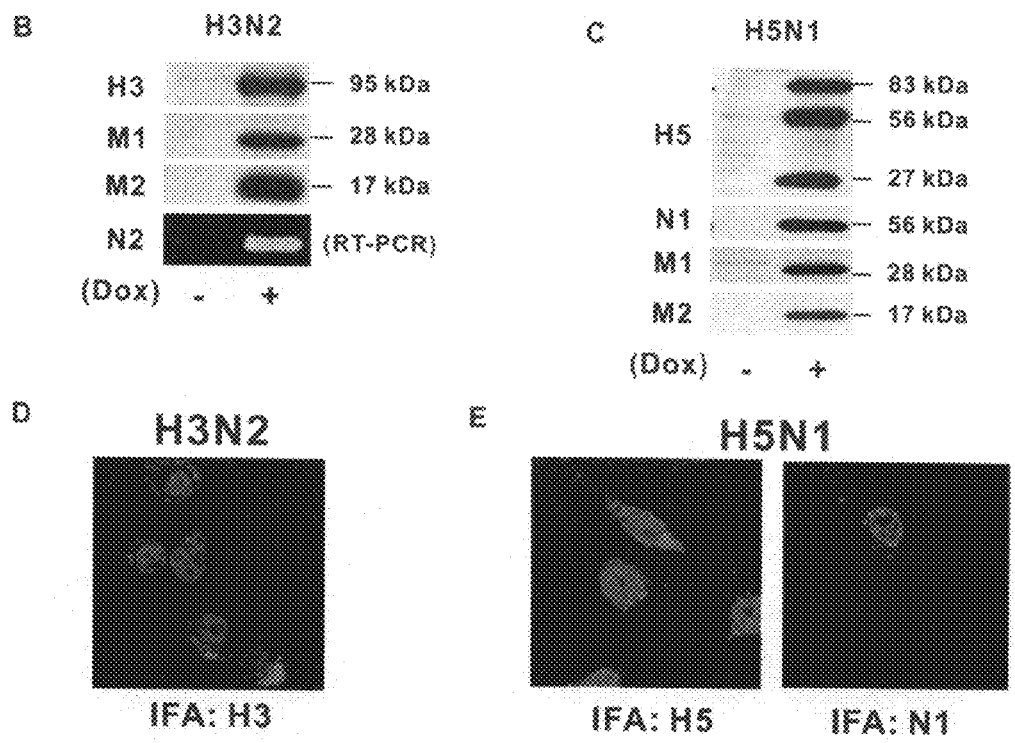

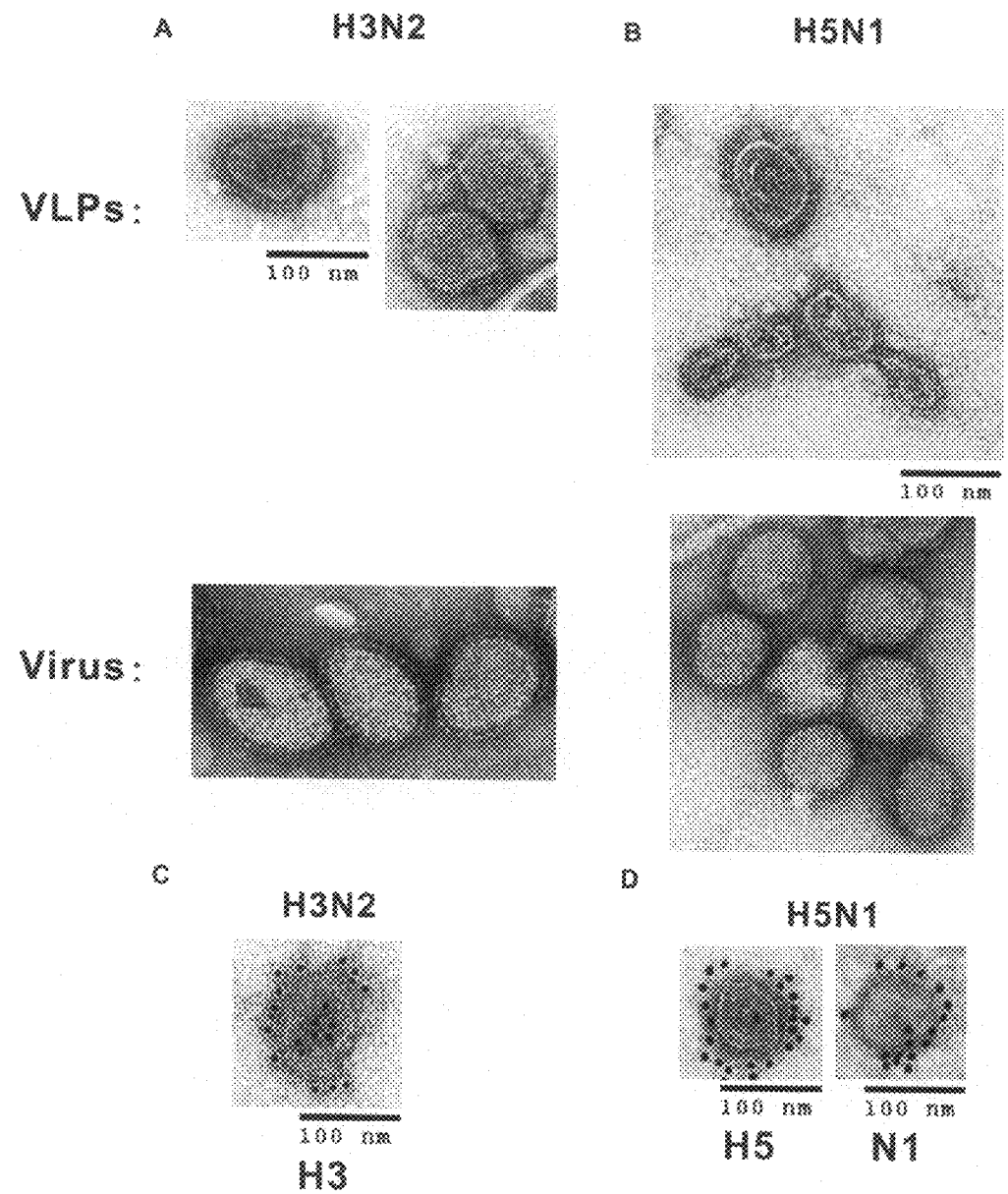

H3N2-VLPs
Average diam. 108.2± 17.9 nm

H3N2 Virus
Average diam.133.5±15.4nm

Figure 7C

H5N1-VLPs
Average diam.125.6±10.5 nm

Figure 7D

H5N1 Virus
Average diam.104.1±12.4 nm

Figure 8
A SDS-PAGE
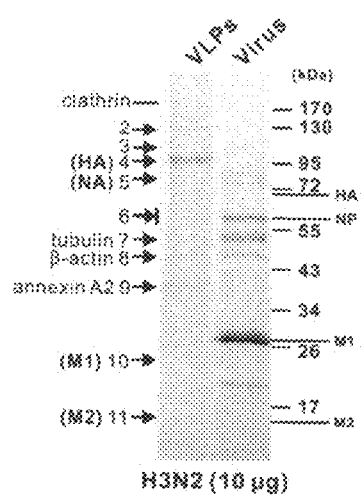
B Anti-H3 & M1 & M2
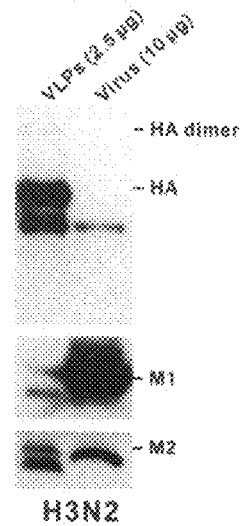
C SDS-PAGE
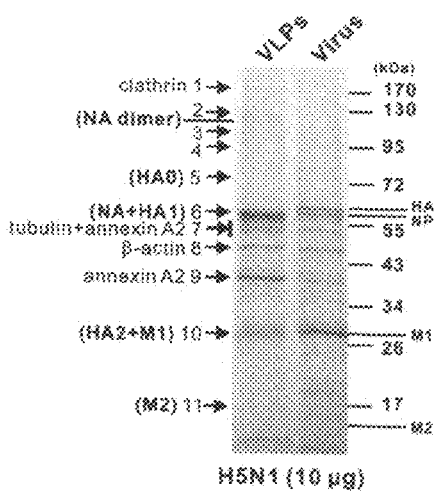
D Anti-H5 & N1 & M1 & M2
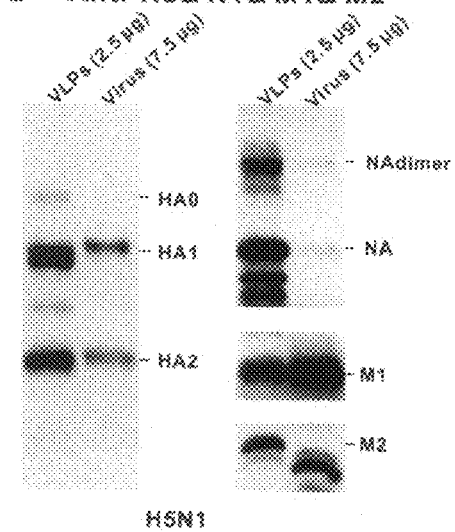
E
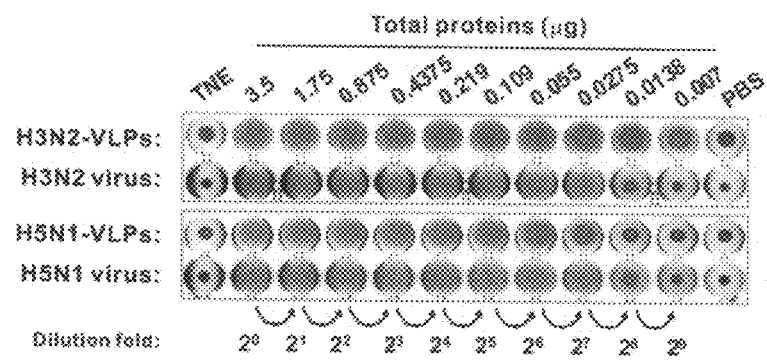

Figure 9

Figure 10
A SDS-PAGE
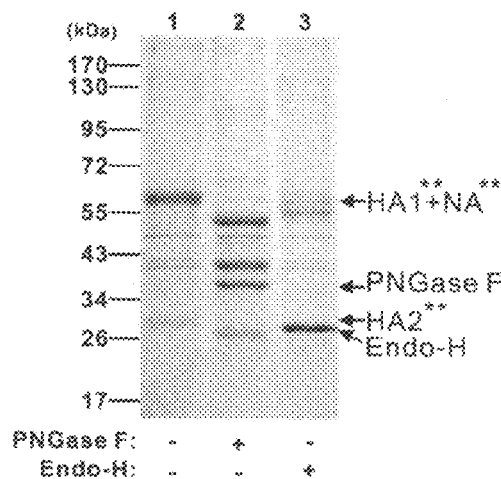
B Anti-H5
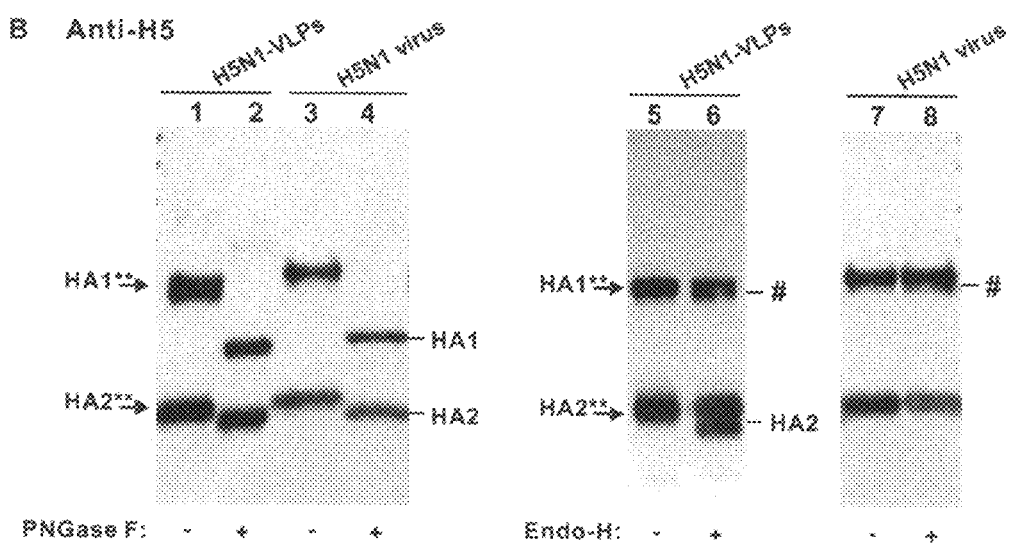
C Anti-N1    D Anti-H3
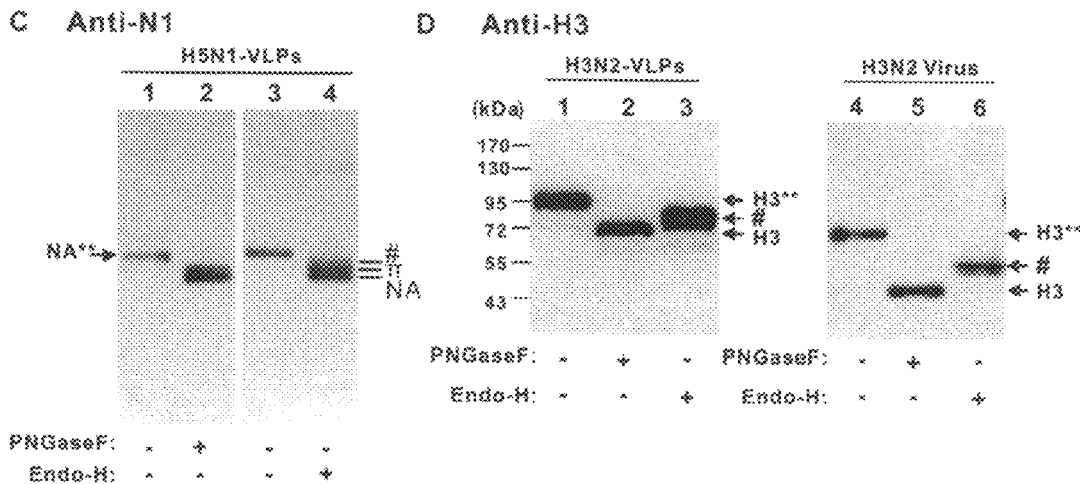

SEQUENCE LISTING

```
<160> NUMBER OF SEQ ID NOS: 17

<210> SEQ ID NO 1
<211> LENGTH: 3484
<212> TYPE: DNA
<213> ORGANISM: Artificial Sequence
<220> FEATURE:
<223> OTHER INFORMATION: expression cassette

<400> SEQUENCE: 1
gttgacattg attattgact agttattaat agtaatcaat tacgggtca ttagttcata    60
```

```
gcccatatat ggagttccgc gttacataac ttacggtaaa tggcccgcct ggctgaccgc    120
ccaacgaccc ccgcccattg acgtcaataa tgacgtatgt tcccatagta acgccaatag    180
ggactttcca ttgacgtcaa tgggtggagt atttacggta aactgcccac ttggcagtac    240
atcaagtgta tcatatgcca agtacgcccc ctattgacgt caatgacggt aaatggcccg    300
cctggcatta tgcccagtac atgaccttat gggactttcc tacttggcag tacatctacg    360
tattagtcat cgctattacc atggtgatgc ggttttggca gtacatcaat gggcgtggat    420
agcggtttga ctcacgggga tttccaagtc tccaccccat tgacgtcaat gggagtttgt    480
tttggcacca aaatcaacgg gactttccaa aatgtcgtaa caactccgcc ccattgacgc    540
aaatgggcgg taggcgtgta cggtgggagg tctatataag cagagctctc cctatcagtg    600
atagagatct cccatcagt gatagagatc gtcgacgagc tcgtttagtg aaccgtcaga    660
tcgcctggag acgccatcca cgctgttttg acctccatag aagacaccgg gaccgatcca    720
gcctccggac tctagcgttt aaacttaagc ttggtaccga gctcggatcc cttgcagaag    780
ttggtcgtga ggcactgggc aggtaagtat caaggttaca agacaggttt aaggagacca    840
atagaaactg ggcttgtcga dacagagaag actcttgcgt ttctgatagg cacctattgg    900
tcttactgac atccactttg cctttctctc cacaggtgtc cactcccagt tcaattacag    960
ctcttaaggc tagagtactt aatacgactc actataggct agcatggcag acaacggtac   1020
tattaccgtt gaggagctta acaactcct ggaacaatgg aacctagtaa taggtttcct   1080
attcctagcc tggattatgt tactacaatt tgcctattct aatcggaaca ggttttgta    1140 cataataaag cttgttttcc tctggctctt gtggccagta acacttgctt gttttgtgct   1200
tgctgctgtc tacagaatta attgggtgac tggcgggatt gcgattgcaa tggcttgtat   1260
tgtaggcttg atgtgctta gctacttcgt tgcttccttc aggctgtttg ctcgtacccg   1320
ctcaatgtgg tcattcaacc cagaaacaaa cattcttctc aatgtgcctc tccggggac   1380 aattgtgacc agaccgctca tggaaagtga acttgtcatt ggtgctgtga tcattcgtgg   1440
tcacttgcga atggccggac acccctagg gcgctgtgac attaaggacc tgccaaaaga   1500
gatcactgtg gctacatcac gaacgctttc ttattacaaa ttaggagcgt cgcagcgtgt   1560
aggcactgat tcaggttttg ctgcatacaa ccgctaccgt attggaaact ataaattaaa   1620
tacagaccac gccggtagca acgacaatat tgctttgcta gtacaggagc tcgtgagcaa   1680
gggcgaggag ctgttcaccg gggtggtgcc catcctggtc gagctggacg gcgacgtaaa   1740
cggccacaag ttcagcgtgt ccggcgaggg cgagggcgat gccacctacg gcaagctgac   1800
cctgaagttc atctgcacca ccggcaagct gcccgtgccc tggcccgccc tcgtgaccac   1860
cctgacctac ggcgtgcagt gcttcagccg ctaccccgac cacatgaagc agcacgactt   1920
cttcaagtcc gccatgcccg aaggctacgt ccaggagcgc accatcttct tcaaggacga   1980
cggcaactac aagacccgcg ccgaggtgaa gttcgagggc gacaccctgg tgaaccgcat   2040
cgagctgaag ggcatcgact tcaaggagga cggcaacatc ctggggcaca agctggagta   2100
caactacaac agccacaacg tctatatcat ggccgacaag cagaagaacg gcatcaaggt   2160
gaacttcaag atccgccaca acatcgagga cggcagcgtg cagctcgccg accactacca   2220
gcagaacacc cccatcggcg acggccccgt gctgctgccc gacaaccact acctgagcac   2280
ccagtccgcc ctgagcaaag accccaacga gaagcgcgat cacatggtcc tgctggagtt   2340
cgtgaccgcc gccgggatca ctctcggcat ggacgagctg tacaagtaag aattccgccc   2400 ctctcccctcc ccccccccta cgttactggg ccgaagccgc ttggaataag gccggtgtgt   2460
```

```
gtttgtctat atgtgatttt ccaccatatt gccgtctttt ggcaatgtga gggcccggaa    2520 acctggcccct gtcttcttga cgagcattcc tagggggtctt tcccctctcg ccaaaggaat   2580
gcaaggtctg ttgaatgtcg tgaaggaagc agttcctctg gaagcttctt gaagacaaac    2640
aacgtctgta gcgacccttt gcaggcagcg gaaccccca cctggcgaca ggtgcctctg     2700
cggccaaaag ccacgtgtat aagatacacc tgcaaaggcg gcacaacccc agtgccacgt    2760
tgtgagttgg atagttgtgg aaagagtcaa atggctctcc tcaagcgtag tcaacaaggg    2820
gctgaaggat gcccagaagg taccccattg tatgggaatc tgatctgggg cctcggtgca    2880
catgctttac atgtgtttag tcgaggttaa aaaaacgtct aggcccccg aaccacgggg     2940 acgtggtttt cctttgaaaa acacgatgat aatatggcca caaccggatc tatgtactca    3000
ttcgtttcgg aagaaacagg tacgttaata gttaatagcg tacttctttt tcttgctttc    3060
gtggtattct tgctagtcac actagccatc cttactgcgc ttcgattgtg tgcgtactgc    3120
tgcaatattg ttaacgtgag tttagtaaaa ccaacggttt acgtctactc gcgtgttaaa    3180
aatctgaact cttctgaagg agttcctgat cttctggtct aatctagagg gcccgtttaa    3240
acccgctgat cagcctcgac tgtgccttct agttgccagc catctgttgt ttgccctcc    3300 cccgtgcctt ccttgaccct ggaaggtgcc actcccactg tcctttccta ataaaatgag    3360
gaaattgcat cgcattgtct gagtaggtgt cattctattc tggggggtgg ggtggggcag    3420
gacagcaagg gggaggattg ggaagacaat agcaggcatg ctggggatgc ggtgggctct    3480
atgg                                                                 3484
```

<210> SEQ ID NO 2
<211> LENGTH: 4837
<212> TYPE: DNA
<213> ORGANISM: Artificial Sequence
<220> FEATURE:
<223> OTHER INFORMATION: expression cassette

<400> SEQUENCE: 2

```
gttgacattg attattgact agttattaat agtaatcaat tacggggtca ttagttcata     60
gcccatatat ggagttccgc gttacataac ttacggtaaa tggcccgcct ggctgaccgc    120
ccaacgaccc ccgcccattg acgtcaataa tgacgtatgt tcccatagta acgccaatag    180
ggactttcca ttgacgtcaa tgggtggagt atttacggta aactgcccac ttggcagtac    240
atcaagtgta tcatatgcca agtacgcccc ctattgacgt caatgacggt aaatggcccg    300
cctggcatta tgcccagtac atgaccttat gggactttcc tacttggcag tacatctacg    360
tattagtcat cgctattacc atggtgatgc ggttttggca gtacatcaat gggcgtggat    420
agcggtttga ctcacgggga tttccaagtc tccacccccat tgacgtcaat gggagtttgt    480
tttggcacca aaatcaacgg gactttccaa aatgtcgtaa caactccgcc ccattgacgc    540
aaatgggcgg taggcgtgta cggtgggagg tctatataag cagagctctc cctatcagtg    600
atagagatct cccctatcagt gatagagatc gtcgacgagc tcgtttagtg aaccgtcaga    660
tcgcctggag acgccatcca cgctgttttg acctccatag aagacaccgg gaccgatcca    720
gcctccggac tctagcgttt aaacttaagc ttggtaccga gctcggatcc atgtttattt    780
tcttattatt tcttactctc actagtggta gtgaccttga ccggtgcacc acttttgatg    840
atgttcaagc tcctaattac actcaacata cttcatctat gaggggggtt tactatcctg    900
atgaaatttt tagatcagac actctttatt taactcagga tttatttctt ccatttatt    960
```

```
ctaatgttac agggtttcat actattaatc atacgtttgg caaccctgtc atacctttta   1020
aggatggtat ttattttgct gccacagaga aatcaaatgt tgtccgtggt tgggttttg    1080
gttctaccat gaacaacaag tcacagtcgg tgattattat taacaattct actaatgttg   1140
ttatacgagc atgtaacttt gaattgtgtg acaacccttt ctttgctgtt tctaaaccca   1200
tgggtacaca gacacatact atgatattcg ataatgcatt taattgcact ttcgagtaca   1260
tatctgatgc cttttcgctt gatgtttcag aaaagtcagg taattttaaa cacttacgag   1320
agtttgtgtt taaaaataaa gatgggtttc tctatgttta aagggctat caacctatag    1380
atgtagttcg tgatctacct tctggtttta acactttgaa acctattttt aagttgcctc   1440
ttggtattaa cattacaaat tttagagcca ttcttacagc cttttcacct gctcaagaca   1500
tttggggcac gtcagctgca gcctattttg ttggctattt aaagccaact acatttatgc   1560
tcaagtatga tgaaaatggt acaatcacag atgctgttga ttgttctcaa aatccacttg   1620
ctgaactcaa atgctctgtt aagagctttg agattgacaa aggaatttac cagacctcta   1680
atttcagggt tgttccctca ggagatgttg tgagattccc taatattaca aacttgtgtc   1740
cttttggaga ggttttaat gctactaaat tcccttctgt ctatgcatgg gagagaaaaa    1800
aaatttctaa ttgtgttgct gattactctg tgctctacaa ctcaacattt ttttcaacct   1860
ttaagtgcta tggcgtttct gccactaagt tgaatgatct ttgcttctcc aatgtctatg   1920
cagattcttt tgtagtcaag ggagatgatg taagacaaat agcgccagga caaactggtg   1980
ttattgctga ttataattat aaattgccag atgatttcat gggttgtgtc cttgcttgga   2040
atactaggaa cattgatgct acttcaactg gtaattataa ttataaatat aggtatctta   2100
gacatggcaa gcttaggccc tttgagagag acatatctaa tgtgcctttc tccctgatg    2160
gcaaaccttg caccccacct gctcttaatt gttattggcc attaaatgat tatggttttt   2220
acaccactac tggcattggc taccaacctt acagagttgt agtactttct tttgaacttt   2280
taaatgcacc ggccacggtt tgtggaccaa aattatccac tgaccttatt aagaaccagt   2340
gtgtcaattt taattttaat ggactcactg gtactggtgt gttaactcct tcttcaaaga   2400
gatttcaacc atttcaacaa tttggccgtg atgtttctga tttcactgat tccgttcgag   2460
atcctaaaac atctgaaata ttagacattt caccttgctc ttttgggggt gtaagtgtaa   2520
ttacacctgg aacaaatgct tcatctgaag ttgctgttct atatcaagat gttaactgca   2580
ctgatgtttc tacagcaatt catgcagatc aactcacacc agcttggcgc atatattcta   2640
ctggaaacaa tgtattccag actcaagcag gctgtcttat aggagctgag catgtcgaca   2700
cttcttatga gtgcgacatt cctattggag ctggcatttg tgctagttac catacagttt   2760
ctttattacg tagtactagc caaaaatcta ttgtggctta tactatgtct ttaggtgctg   2820
atagttcaat tgcttactct aataacacca ttgctatacc tactaacttt tcaattagca   2880
ttactacaga agtaatgcct gtttctatgg ctaaaacctc cgtagattgt aatatgtaca   2940
tctgcggaga ttctactgaa tgtgctaatt tgcttctcca atatggtagc ttttgcacac   3000
aactaaatcg tgcactctca ggtattgctg ctgaacagga tcgcaacaca cgtgaagtgt   3060
tcgctcaagt caaacaaatg tacaaaaccc aactttgaa atattttggt ggttttaatt    3120
tttcacaaat attacctgac cctctaaagc caactaagag gtcttttatt gaggacttgc   3180
tctttaataa ggtgacactc gctgatgctg gcttcatgaa gcaatatggc gaatgcctag   3240
gtgatattaa tgctagagat ctcatttgtg cgcagaagtt caatggactt acagtgttgc   3300
caccctctgct cactgatgat atgattgctg cctacactgc tgctctagtt agtggtactg   3360
```

```
ccactgctgg atggacattt ggtgctggcg ctgctcttca ataccttttt gctatgcaaa    3420
tggcatatag gttcaatggc attggagtta cccaaaatgt tctctatgag aaccaaaaac    3480
aaatcgccaa ccaatttaac aaggcgatta gtcaaattca agaatcactt acaacaacat    3540
caactgcatt gggcaagctg caagacgttg ttaaccagaa tgctcaagca ttaaacacac    3600
ttgttaaaca acttagctct aattttggtg caatttcaag tgtgctaaat gatatccttt    3660
cgcgacttga taaagtcgag gcggaggtac aaattgacag gttaattaca ggcagacttc    3720
aaagccttca aacctatgta acacaacaac taatcagggc tgctgaaatc agggcttctg    3780
ctaatcttgc tgctactaaa atgtctgagt gtgttcttgg acaatcaaaa agagttgact    3840
tttgtggaaa gggctaccac cttatgtcct cccacaagc agccccgcat ggtgttgtct    3900
tcctacatgt cacgtatgtg ccatcccagg agaggaactt caccacagcg ccagcaattt    3960
gtcatgaagg caaagcatac ttccctcgtg aaggtgtttt tgtgtttaat ggcacttctt    4020
ggtttattac acagaggaac ttcttttctc cacaaataat tactacagac aatacatttg    4080
tctcaggaaa ttgtgatgtc gttattggca tcattaacaa cacagtttat gatcctctgc    4140
aacctgagct tgactcattc aaagaagagc tggacaagta cttcaaaaat catacatcac    4200
cagatgttga tcttggcgac atttcaggca ttaacgcttc tgtcgtcaac attcaaaaag    4260
aaattgaccg cctcaatgag gtcgctaaaa atttaaatga atcactcatt gaccttcaag    4320
aattgggaaa atatgagcaa tatattaaat ggccttggta tgtttggctc ggcttcattg    4380
ctggactaat tgccatcgtc atggttacaa tcttgctttg ttgcatgact agttgttgca    4440
gttgcctcaa gggtgcatgc tcttgtggtt cttgctgcaa gtttgatgag gatgactctg    4500
agccagttct caaggtgtc aaattacatt acacataaaa gcttgcaatc actagtgaat    4560
tcgcggccgc tcgagtctag agggcccgtt taaacccgct gatcagcctc gactgtgcct    4620
tctagttgcc agccatctgt tgtttgcccc tcccccgtgc cttccttgac cctggaaggt    4680
gccactccca ctgtcctttc ctaataaaat gaggaaattg catcgcattg tctgagtagg    4740
tgtcattcta ttctgggggg tggggtgggg caggacagca agggggagga ttgggaagac    4800
aatagcaggc atgctgggga tgcggtgggc tctatgg                              4837
```

<210> SEQ ID NO 3
<211> LENGTH: 221
<212> TYPE: PRT
<213> ORGANISM: SARS coronavirus Urbani

<400> SEQUENCE: 3

```
Met Ala Asp Asn Gly Thr Ile Thr Val Glu Glu Leu Lys Gln Leu Leu
1               5                   10                  15

Glu Gln Trp Asn Leu Val Ile Gly Phe Leu Phe Leu Ala Trp Ile Met
            20                  25                  30

Leu Leu Gln Phe Ala Tyr Ser Asn Arg Asn Arg Phe Leu Tyr Ile Ile
        35                  40                  45

Lys Leu Val Phe Leu Trp Leu Leu Trp Pro Val Thr Leu Ala Cys Phe
    50                  55                  60

Val Leu Ala Ala Val Tyr Arg Ile Asn Trp Val Thr Gly Gly Ile Ala
65                  70                  75                  80

Ile Ala Met Ala Cys Ile Val Gly Leu Met Trp Leu Ser Tyr Phe Val
                85                  90                  95

Ala Ser Phe Arg Leu Phe Ala Arg Thr Arg Ser Met Trp Ser Phe Asn
            100                 105                 110
```

-continued

```
Pro Glu Thr Asn Ile Leu Leu Asn Val Pro Leu Arg Gly Thr Ile Val
        115                 120                 125

Thr Arg Pro Leu Met Glu Ser Glu Leu Val Ile Gly Ala Val Ile Ile
    130                 135                 140

Arg Gly His Leu Arg Met Ala Gly His Pro Leu Gly Arg Cys Asp Ile
145                 150                 155                 160

Lys Asp Leu Pro Lys Glu Ile Thr Val Ala Thr Ser Arg Thr Leu Ser
                165                 170                 175

Tyr Tyr Lys Leu Gly Ala Ser Gln Arg Val Gly Thr Asp Ser Gly Phe
            180                 185                 190

Ala Ala Tyr Asn Arg Tyr Arg Ile Gly Asn Tyr Lys Leu Asn Thr Asp
        195                 200                 205

His Ala Gly Ser Asn Asp Asn Ile Ala Leu Leu Val Gln
    210                 215                 220

<210> SEQ ID NO 4
<211> LENGTH: 76
<212> TYPE: PRT
<213> ORGANISM: SARS coronavirus Urbani

<400> SEQUENCE: 4

Met Tyr Ser Phe Val Ser Glu Glu Thr Gly Thr Leu Ile Val Asn Ser
1               5                   10                  15

Val Leu Leu Phe Leu Ala Phe Val Val Phe Leu Leu Val Thr Leu Ala
            20                  25                  30

Ile Leu Thr Ala Leu Arg Leu Cys Ala Tyr Cys Cys Asn Ile Val Asn
        35                  40                  45

Val Ser Leu Val Lys Pro Thr Val Tyr Val Tyr Ser Arg Val Lys Asn
    50                  55                  60

Leu Asn Ser Ser Glu Gly Val Pro Asp Leu Leu Val
65                  70                  75

<210> SEQ ID NO 5
<211> LENGTH: 1255
<212> TYPE: PRT
<213> ORGANISM: SARS coronavirus TW1

<400> SEQUENCE: 5

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140
```

-continued

```
Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
            165                 170                 175

Gly Asn Phe Lys His Leu Arg Glu Phe Val Phe Lys Asn Lys Asp Gly
        180                 185                 190

Phe Leu Tyr Val Tyr Lys Gly Tyr Gln Pro Ile Asp Val Val Arg Asp
    195                 200                 205

Leu Pro Ser Gly Phe Asn Thr Leu Lys Pro Ile Phe Lys Leu Pro Leu
210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Tyr Phe Val Gly Tyr
            245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
            275                 280                 285

Ser Val Lys Ser Phe Glu Ile Asp Lys Gly Ile Tyr Gln Thr Ser Asn
290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
            325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
            355                 360                 365

Val Ser Ala Thr Lys Leu Asn Asp Leu Cys Phe Ser Asn Val Tyr Ala
370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
            405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
            435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
            485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
            515                 520                 525

Phe Asn Gly Leu Thr Gly Thr Gly Val Leu Thr Pro Ser Ser Lys Arg
        530                 535                 540

Phe Gln Pro Phe Gln Gln Phe Gly Arg Asp Val Ser Asp Phe Thr Asp
545                 550                 555                 560
```

-continued

```
Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
        595                 600                 605

Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
        675                 680                 685

Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
        755                 760                 765

Gln Met Tyr Lys Thr Pro Thr Leu Lys Tyr Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
        835                 840                 845

Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
```

```
                      980              985              990
       Gln Leu Ile Arg Ala Ala Glu Ile  Arg Ala Ser Ala Asn  Leu Ala Ala
                       995              1000             1005

Thr Lys Met Ser Glu Cys Val Leu  Gly Gln Ser Lys  Arg Val Asp
           1010             1015             1020

Phe Cys Gly Lys Gly Tyr His Leu  Met Ser Phe Pro  Gln Ala Ala
           1025             1030             1035

Pro His Gly Val Val Phe Leu His  Val Thr Tyr Val  Pro Ser Gln
           1040             1045             1050

Glu Arg Asn Phe Thr Thr Ala Pro  Ala Ile Cys His  Glu Gly Lys
           1055             1060             1065

Ala Tyr Phe Pro Arg Glu Gly Val  Phe Val Phe Asn  Gly Thr Ser
           1070             1075             1080

Trp Phe Ile Thr Gln Arg Asn Phe  Phe Ser Pro Gln  Ile Ile Thr
           1085             1090             1095

Thr Asp Asn Thr Phe Val Ser Gly  Asn Cys Asp Val  Val Ile Gly
           1100             1105             1110

Ile Ile Asn Asn Thr Val Tyr Asp  Pro Leu Gln Pro  Glu Leu Asp
           1115             1120             1125

Ser Phe Lys Glu Glu Leu Asp Lys  Tyr Phe Lys Asn  His Thr Ser
           1130             1135             1140

Pro Asp Val Asp Leu Gly Asp Ile  Ser Gly Ile Asn  Ala Ser Val
           1145             1150             1155

Val Asn Ile Gln Lys Glu Ile Asp  Arg Leu Asn Glu  Val Ala Lys
           1160             1165             1170

Asn Leu Asn Glu Ser Leu Ile Asp  Leu Gln Glu Leu  Gly Lys Tyr
           1175             1180             1185

Glu Gln Tyr Ile Lys Trp Pro Trp  Tyr Val Trp Leu  Gly Phe Ile
           1190             1195             1200

Ala Gly Leu Ile Ala Ile Val Met  Val Thr Ile Leu  Leu Cys Cys
           1205             1210             1215

Met Thr Ser Cys Cys Ser Cys Leu  Lys Gly Ala Cys  Ser Cys Gly
           1220             1225             1230

Ser Cys Cys Lys Phe Asp Glu Asp  Asp Ser Glu Pro  Val Leu Lys
           1235             1240             1245

Gly Val Lys Leu His Tyr Thr
           1250             1255

<210> SEQ ID NO 6
<211> LENGTH: 252
<212> TYPE: PRT
<213> ORGANISM: influenza A/Taiwan/083/2006

<400> SEQUENCE: 6

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
                20                  25                  30

Ala Gly Lys Asn Thr Asp Leu Glu Ala Leu Met Glu Trp Leu Lys Thr
            35                  40                  45

Arg Pro Ile Leu Ser Pro Leu Thr Lys Gly Ile Leu Gly Phe Val Phe
        50                  55                  60

Thr Leu Thr Val Pro Ser Glu Arg Gly Leu Gln Arg Arg Arg Phe Val
65                  70                  75                  80
```

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ala Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Ala Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Ile Ala Ser Gln
        195                 200                 205

Ala Arg Gln Met Val Gln Ala Met Arg Ala Ile Gly Thr His Pro Ser
    210                 215                 220

Ser Ser Thr Gly Leu Arg Asp Asp Leu Leu Glu Asn Leu Gln Thr Tyr
225                 230                 235                 240

Gln Lys Arg Met Gly Val Gln Met Gln Arg Phe Lys
                245                 250

<210> SEQ ID NO 7
<211> LENGTH: 97
<212> TYPE: PRT
<213> ORGANISM: influenza A/Taiwan/083/2006

<400> SEQUENCE: 7

Met Ser Leu Leu Thr Glu Val Glu Thr Pro Ile Arg Asn Glu Trp Gly
1               5                   10                  15

Cys Arg Cys Asn Asp Ser Ser Asp Pro Leu Val Val Ala Ala Asn Ile
            20                  25                  30

Ile Gly Ile Leu His Leu Ile Leu Trp Ile Leu Asp Arg Leu Phe Phe
        35                  40                  45

Lys Cys Val Tyr Arg Leu Phe Lys His Gly Leu Lys Arg Gly Pro Ser
    50                  55                  60

Thr Glu Gly Val Pro Glu Ser Met Arg Glu Glu Tyr Arg Lys Glu Gln
65                  70                  75                  80

Gln Asn Ala Val Asp Ala Asp Asp Ser His Phe Val Ser Ile Glu Leu
                85                  90                  95

Glu

<210> SEQ ID NO 8
<211> LENGTH: 566
<212> TYPE: PRT
<213> ORGANISM: influenza A/Taiwan/083/2006

<400> SEQUENCE: 8

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr

-continued

```
                50                    55                    60
Gly Gly Ile Cys Asp Ser Pro His Gln Ile Leu Asp Gly Glu Asn Cys
 65                  70                  75                  80

Thr Leu Ile Asp Ala Leu Leu Gly Asp Pro Gln Cys Asp Gly Phe Gln
                 85                  90                  95

Asn Lys Lys Trp Asp Leu Phe Val Glu Arg Ser Lys Ala Tyr Ser Asn
                100                 105                 110

Cys Tyr Pro Tyr Asp Val Pro Asp Tyr Ala Ser Leu Arg Ser Leu Val
                115                 120                 125

Ala Ser Ser Gly Thr Leu Glu Phe Asn Asn Glu Ser Phe Asn Trp Thr
130                 135                 140

Gly Val Thr Gln Asn Gly Thr Ser Ser Ala Cys Lys Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
                180                 185                 190

Leu Tyr Ile Trp Gly Val His His Pro Gly Thr Asp Asn Asp Gln Ile
                195                 200                 205

Phe Leu Tyr Ala Gln Ala Ser Gly Arg Ile Thr Val Ser Thr Lys Arg
                210                 215                 220

Ser Gln Gln Thr Val Ile Pro Asn Ile Gly Ser Arg Pro Arg Val Arg
225                 230                 235                 240

Asp Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
                260                 265                 270

Tyr Phe Lys Ile Arg Ser Gly Lys Ser Ser Ile Met Arg Ser Asp Ala
                275                 280                 285

Pro Ile Gly Lys Cys Asn Ser Glu Cys Ile Thr Pro Asn Gly Ser Ile
                290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
                340                 345                 350

Gly Phe Ile Glu Asn Gly Trp Glu Gly Met Val Asp Gly Trp Tyr Gly
                355                 360                 365

Phe Arg His Gln Asn Ser Glu Gly Ile Gly Gln Ala Ala Asp Leu Lys
                370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
                420                 425                 430

Lys Ile Asp Leu Trp Ser Tyr Asn Ala Glu Leu Leu Val Ala Leu Glu
                435                 440                 445

Asn Gln His Thr Ile Asp Leu Thr Asp Ser Glu Met Asn Lys Leu Phe
                450                 455                 460

Glu Arg Thr Lys Lys Gln Leu Arg Glu Asn Ala Glu Asp Met Gly Asn
465                 470                 475                 480
```

```
Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Phe Leu Leu Cys
        530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 9
<211> LENGTH: 469
<212> TYPE: PRT
<213> ORGANISM: influenza A/Taiwan/083/2006

<400> SEQUENCE: 9

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asn Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Val His
    130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Val Thr Gly Asp Asp Lys Asn Ala Thr Ala Ser Phe Ile Tyr Asn
        195                 200                 205

Gly Arg Leu Val Asp Ser Ile Val Ser Trp Ser Lys Glu Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Thr Leu Ser Gly Ser Ala
            260                 265                 270

Gln His Val Glu Glu Cys Ser Cys Tyr Pro Arg Tyr Pro Gly Val Arg
```

```
                275                 280                 285
Cys Val Cys Arg Asp Asn Trp Lys Gly Ser Asn Arg Pro Ile Val Asp
290                 295                 300
Ile Asn Ile Lys Asp Tyr Ser Ile Val Ser Ser Tyr Val Cys Ser Gly
305                 310                 315                 320
Leu Val Gly Asp Thr Pro Arg Lys Asn Asp Ser Ser Ser Ser Gly His
                325                 330                 335
Cys Leu Asp Pro Asn Asn Glu Glu Gly Gly His Gly Val Lys Gly Trp
                340                 345                 350
Ala Phe Asp Asp Gly Asn Asp Val Trp Met Gly Arg Thr Ile Ser Glu
                355                 360                 365
Lys Leu Arg Ser Gly Tyr Glu Thr Phe Lys Val Ile Glu Gly Trp Ser
370                 375                 380
Asn Pro Asn Ser Lys Leu Gln Ile Asn Arg Gln Val Ile Val Asp Arg
385                 390                 395                 400
Gly Asn Arg Ser Gly Tyr Ser Gly Ile Phe Ser Val Glu Gly Lys Ser
                405                 410                 415
Cys Ile Asn Arg Cys Phe Tyr Val Glu Leu Ile Arg Gly Arg Lys Glu
                420                 425                 430
Glu Thr Glu Val Leu Trp Thr Ser Asn Ser Ile Val Val Phe Cys Gly
                435                 440                 445
Thr Ser Gly Thr Tyr Gly Thr Gly Ser Trp Pro Asp Gly Ala Asp Ile
                450                 455                 460
Asn Leu Met Pro Ile
465

<210> SEQ ID NO 10
<211> LENGTH: 567
<212> TYPE: PRT
<213> ORGANISM: influenza A/Hanoi/30408/2005(H5N1)

<400> SEQUENCE: 10

Met Glu Lys Ile Val Leu Leu Phe Ala Ile Val Ser Leu Val Lys Ser
1               5                   10                  15
Asp Gln Ile Cys Ile Gly Tyr His Ala Asn Asn Ser Thr Glu Gln Val
            20                  25                  30
Asp Thr Ile Met Glu Lys Asn Val Thr Val Thr His Ala Gln Asp Ile
        35                  40                  45
Leu Glu Lys Thr His Asn Gly Lys Leu Cys Asp Leu Asp Gly Val Lys
    50                  55                  60
Pro Leu Ile Leu Arg Asp Cys Ser Val Ala Gly Trp Leu Leu Gly Asn
65                  70                  75                  80
Pro Met Cys Asp Glu Phe Ile Asn Val Pro Glu Trp Ser Tyr Ile Val
                85                  90                  95
Glu Lys Ala Asn Pro Val Asn Asp Leu Cys Tyr Pro Gly Asp Phe Asn
            100                 105                 110
Asp Tyr Glu Glu Leu Lys His Leu Leu Ser Arg Ile Asn His Phe Glu
        115                 120                 125
Lys Ile Gln Ile Ile Pro Lys Ser Ser Trp Leu Ser His Glu Ala Ser
    130                 135                 140
Leu Gly Val Ser Ser Ala Cys Pro Tyr Gln Gly Lys Ser Ser Phe Phe
145                 150                 155                 160
Arg Asn Val Val Trp Leu Ile Lys Lys Asn Ser Thr Tyr Pro Thr Ile
                165                 170                 175
```

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
                260                 265                 270

Val Lys Lys Gly Asp Ser Thr Ile Met Lys Ser Glu Leu Glu Tyr Gly
            275                 280                 285

Asn Cys Asn Thr Lys Cys Gln Thr Pro Met Gly Ala Ile Asn Ser Ser
        290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Lys Arg Gly Leu Phe Gly Ala Ile Ala
                340                 345                 350

Gly Phe Ile Glu Gly Gly Trp Gln Gly Met Val Asp Gly Trp Tyr Gly
            355                 360                 365

Tyr His His Ser Asn Glu Gln Gly Ser Gly Tyr Ala Ala Asp Lys Glu
        370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
                420                 425                 430

Phe Leu Asp Val Trp Thr Tyr Asn Ala Glu Leu Leu Val Leu Met Glu
            435                 440                 445

Asn Glu Arg Thr Leu Asp Phe His Asp Ser Asn Val Lys Asn Leu Tyr
450                 455                 460

Asp Lys Val Arg Leu Gln Leu Arg Asp Asn Ala Lys Glu Leu Gly Asn
465                 470                 475                 480

Gly Cys Phe Glu Phe Tyr His Lys Cys Asp Asn Glu Cys Met Glu Ser
                485                 490                 495

Val Arg Asn Gly Thr Tyr Asp Tyr Pro Gln Tyr Ser Glu Glu Ala Lys
            500                 505                 510

Leu Lys Arg Gly Glu Ile Ser Gly Val Lys Leu Glu Ser Ile Gly Ile
        515                 520                 525

Tyr Gln Ile Leu Ser Ile Tyr Ser Thr Val Ala Ser Ser Leu Ala Leu
    530                 535                 540

Ala Ile Met Val Ala Gly Leu Ser Leu Trp Met Cys Ser Asn Gly Ser
545                 550                 555                 560

Leu Gln Cys Arg Ile Cys Ile
                565

<210> SEQ ID NO 11
<211> LENGTH: 449
<212> TYPE: PRT

<213> ORGANISM: influenza A/Hanoi/30408/2005(H5N1)

<400> SEQUENCE: 11

```
Met Asn Pro Asn Gln Lys Ile Ile Thr Ile Gly Ser Ile Cys Met Val
1               5                   10                  15

Thr Gly Ile Val Ser Leu Met Leu Gln Ile Gly Asn Met Ile Ser Ile
            20                  25                  30

Trp Val Ser His Ser Ile His Thr Gly Asn Gln His Gln Ser Glu Pro
        35                  40                  45

Ile Ser Asn Thr Lys Phe Leu Thr Glu Lys Ala Val Ala Ser Val Lys
    50                  55                  60

Leu Ala Gly Asn Ser Ser Leu Cys Pro Ile Asn Gly Trp Ala Val Tyr
65                  70                  75                  80

Ser Lys Asp Asn Ser Ile Arg Ile Gly Ser Lys Gly Asp Val Phe Val
                85                  90                  95

Ile Arg Glu Pro Phe Ile Ser Cys Ser His Leu Glu Cys Arg Thr Phe
            100                 105                 110

Phe Leu Thr Gln Gly Ala Leu Leu Asn Asp Lys His Ser Asn Gly Thr
        115                 120                 125

Val Lys Asp Arg Ser Pro His Arg Thr Leu Met Ser Cys Pro Val Gly
130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
                165                 170                 175

Gly Pro Asp Asn Gly Ala Val Ala Val Leu Lys Tyr Asn Gly Ile Ile
            180                 185                 190

Thr Asp Thr Ile Lys Ser Trp Arg Asn Asn Ile Leu Arg Thr Gln Glu
        195                 200                 205

Ser Glu Cys Ala Cys Val Asn Gly Ser Cys Phe Thr Val Met Thr Asp
210                 215                 220

Gly Pro Ser Asn Gly Gln Ala Ser His Lys Ile Phe Lys Met Glu Lys
225                 230                 235                 240

Gly Lys Val Val Lys Ser Val Glu Leu Asp Ala Pro Asn Tyr His Tyr
                245                 250                 255

Glu Glu Cys Ser Cys Tyr Pro Asp Ala Gly Glu Ile Thr Cys Val Cys
            260                 265                 270

Arg Asp Asn Trp His Gly Ser Asn Arg Pro Trp Val Ser Phe Asn Gln
        275                 280                 285

Asn Leu Glu Tyr Gln Ile Gly Tyr Ile Cys Ser Gly Val Phe Gly Asp
290                 295                 300

Asn Pro Arg Pro Asn Asp Gly Thr Gly Ser Cys Gly Pro Val Ser Ser
305                 310                 315                 320

Asn Gly Ala Tyr Gly Val Lys Gly Phe Ser Phe Lys Tyr Gly Asn Gly
                325                 330                 335

Val Trp Ile Gly Arg Thr Lys Ser Thr Asn Ser Arg Ser Gly Phe Glu
            340                 345                 350

Met Ile Trp Asp Pro Asn Gly Trp Thr Glu Thr Asp Ser Ser Phe Ser
        355                 360                 365

Val Lys Gln Asp Ile Val Ala Ile Thr Asp Trp Ser Gly Tyr Ser Gly
370                 375                 380

Ser Phe Val Gln His Pro Glu Leu Thr Gly Leu Asp Cys Ile Arg Pro
385                 390                 395                 400
```

Cys Phe Trp Val Glu Leu Ile Arg Gly Arg Pro Lys Glu Ser Thr Ile
            405                 410                 415

Trp Thr Ser Gly Ser Ser Ile Ser Phe Cys Gly Val Asn Ser Asp Thr
        420                 425                 430

Val Gly Trp Ser Trp Pro Asp Gly Ala Glu Leu Pro Phe Thr Ile Asp
    435                 440                 445

Lys

<210> SEQ ID NO 12
<211> LENGTH: 2920
<212> TYPE: DNA
<213> ORGANISM: Artificial Sequence
<220> FEATURE:
<223> OTHER INFORMATION: CMV-TO-intron-M1 coding sequence-IRES-M2 coding
      sequence-polyA

<400> SEQUENCE: 12

| | | | | | |
|---|---|---|---|---|---|
| gttgacattg | attattgact | agttattaat | agtaatcaat | tacggggtca | ttagttcata | 60 |
| gcccatatat | ggagttccgc | gttacataac | ttacggtaaa | tggcccgcct | ggctgaccgc | 120 |
| ccaacgaccc | ccgcccattg | acgtcaataa | tgacgtatgt | tcccatagta | acgccaatag | 180 |
| ggactttcca | ttgacgtcaa | tgggtggagt | atttacggta | aactgcccac | ttggcagtac | 240 |
| atcaagtgta | tcatatgcca | agtacgcccc | ctattgacgt | caatgacggt | aaatggcccg | 300 |
| cctggcatta | tgcccagtac | atgaccttat | gggactttcc | tacttggcag | tacatctacg | 360 |
| tattagtcat | cgctattacc | atggtgatgc | ggttttggca | gtacatcaat | gggcgtggat | 420 |
| agcggtttga | ctcacgggga | tttccaagtc | tccaccccat | tgacgtcaat | gggagtttgt | 480 |
| tttggcacca | aaatcaacgg | gactttccaa | aatgtcgtaa | caactccgcc | ccattgacgc | 540 |
| aaatgggcgg | taggcgtgta | cggtgggagg | tctatataag | cagagctctc | cctatcagtg | 600 |
| atagagatct | ccctatcagt | gatagagatc | gtcgacgagc | tcgtttagtg | aaccgtcaga | 660 |
| tcgcctggag | acgccatcca | cgctgttttg | acctccatag | aagacaccgg | gaccgatcca | 720 |
| gcctccggac | tctagcgttt | aaacttaagc | ttggtaccga | gctcggatcc | cttgcagaag | 780 |
| ttggtcgtga | ggcactgggc | aggtaagtat | caaggttaca | agacaggttt | aaggagacca | 840 |
| atagaaactg | gcttgtcga | dacagagaag | actcttgcgt | ttctgatagg | cacctattgg | 900 |
| tcttactgac | atccactttg | cctttctctc | cacaggtgtc | cactcccagt | tcaattacag | 960 |
| ctcttaaggc | tagagtactt | aatacgactc | actataggct | agcatgagcc | ttctaaccga | 1020 |
| ggtcgaaacg | tatgttctct | ctatcgttcc | atcaggcccc | ctcaaagccg | agatcgcgca | 1080 |
| gagacttgaa | gatgtctttg | ctgggaaaaa | cacagatctt | gaggctctca | tggaatggct | 1140 |
| aaagacaaga | ccaattctgt | cacctctgac | taagggggatt | ttggggtttg | tgttcacgct | 1200 |
| caccgtgcca | agtgagcgag | gactgcagcg | tagacgcttt | gtccaaaatg | ccctcaatgg | 1260 |
| gaatggagat | ccaaataaca | tggacaaagc | agttaaactg | tataggaaac | ttaagaggga | 1320 |
| gataacgttc | catgggggcca | aagaaatagc | tctcagttat | tctgctggtg | cacttgccag | 1380 |
| ttgcatgggc | ctcatataca | atagaatggg | ggctgtaacc | actgaagtgg | catttggcct | 1440 |
| ggtatgtgca | acatgtgagc | agattgctga | ctcccagcac | aggtctcata | ggcaaatggt | 1500 |
| ggcaacaacc | aatccattaa | taagacatga | gaacagaatg | gttttggcca | gcactacagc | 1560 |
| taaggctatg | gagcaaatgg | ctggatcaag | tgagcaggca | gcggaggcca | tggagattgc | 1620 |
| tagtcaggcc | aggcagatgg | tgcaggcaat | gagagccatt | gggactcatc | ctagttccag | 1680 |
| tactggtcta | agagatgatc | ttcttgaaaa | tttgcagacc | tatcagaaac | gaatgggggt | 1740 |

```
gcagatgcaa cgattcaagt gagaattccg cccctctccc tcccccccc ctaacgttac    1800 tggccgaagc cgcttggaat aaggccggtg tgtgtttgtc tatatgtgat tttccaccat    1860
attgccgtct tttggcaatg tgagggcccg gaaacctggc cctgtcttct tgacgagcat    1920
tcctaggggt ctttcccctc tcgccaaagg aatgcaaggt ctgttgaatg tcgtgaagga    1980
agcagttcct ctggaagctt cttgaagaca acaacgtct gtagcgaccc tttgcaggca     2040
gcggaacccc ccacctggcg acaggtgcct ctgcggccaa agccacgtg tataagatac     2100 acctgcaaag gcggcacaac cccagtgcca cgttgtgagt tggatagttg tggaaagagt    2160
caaatggctc tcctcaagcg tagtcaacaa ggggctgaag gatgcccaga aggtacccca    2220
ttgtatggga atctgatctg gggcctcggt gcacatgctt tacatgtgtt tagtcgaggt    2280
taaaaaaacg tctaggcccc ccgaaccacg ggacgtggt tttcctttga aaaacacgat     2340
gataatatgg ccacaaccgg atctatgagc cttctaaccg aggtcgaaac acctatcaga    2400
aacgaatggg ggtgcagatg caacgattca agtgacccgc ttgttgttgc cgcgaatatc    2460
attgggatct tgcacttgat attgtggatt cttgatcgtc ttttttttcaa atgcgtctat    2520 cgactcttca aacacggcct taaaagaggc ccttctacgg aaggagtacc tgagtctatg    2580
agggaagaat atcgaaagga acagcagaat gctgtggatg ctgacgacag tcattttgtc    2640
agcatagagt tggagtaatc tagagggccc gtttaaaccc gctgatcagc ctcgactgtg    2700
ccttctagtt gccagccatc tgttgtttgc ccctcccccg tgccttcctt gaccctggaa    2760
ggtgccactc ccactgtcct ttcctaataa aatgaggaaa ttgcatcgca ttgtctgagt    2820
aggtgtcatt ctattctggg gggtggggtg ggcaggaca gcaaggggga ggattgggaa    2880
gacaatagca ggcatgctgg ggatgcggtg ggctctatgg                          2920
```

<210> SEQ ID NO 13
<211> LENGTH: 2246
<212> TYPE: DNA
<213> ORGANISM: Artificial Sequence
<220> FEATURE:
<223> OTHER INFORMATION: CMV promoter-rabbit beta-globin intron II-Tet R
      coding sequence-SV40 polyA

<400> SEQUENCE: 13

```
gttgacattg attattgact agttattaat agtaatcaat tacggggtca ttagttcata     60
gcccatatat ggagttccgc gttacataac ttacggtaaa tggcccgcct ggctgaccgc    120
ccaacgaccc ccgcccattg acgtcaataa tgacgtatgt tcccatagta acgccaatag    180
ggactttcca ttgacgtcaa tgggtggagt atttacggta aactgcccac ttggcagtac    240
atcaagtgta tcatatgcca agtacgcccc ctattgacgt caatgacggt aaatggcccg    300
cctggcatta tgcccagtac atgaccttat gggactttcc tacttggcag tacatctacg    360
tattagtcat cgctattacc atggtgatgc ggttttggca gtacatcaat gggcgtggat    420
agcggtttga ctcacgggga tttccaagtc tccaccccat tgacgtcaat gggagtttgt    480
tttggcacca aaatcaacgg gactttccaa aatgtcgtaa caactccgcc ccattgacgc    540
aaatgggcgg taggcgtgta cggtgggagg tctatataag cagagctctc tggctaacta    600
gagaacccac tgcttactgg cttatcgaaa ttaatacgac tcactatagg gagacccaag    660
ctggctagcg tttaaactta agcttggtac ccggggatcc tctagggcct ctgagctatt    720
ccagaagtag tgaagaggct ttttggagg cctaggcttt tgcaaaaagc tccgatcga     780 tcctgagaac ttcagggtga gtttggggac ccttgattgt tctttctttt tcgctattgt    840
```

```
aaaattcatg ttatatggag ggggcaaagt tttcagggtg ttgtttagaa tgggaagatg    900
tcccttgtat caccatggac cctcatgata attttgtttc tttcactttc tactctgttg    960
acaaccattg tctcctctta ttttcttttc attttctgta acttttcgt taaactttag   1020 cttgcatttg taacgaattt ttaaattcac ttttgtttat ttgtcagatt gtaagtactt   1080
tctctaatca cttttttttc aaggcaatca gggtatatta tattgtactt cagcacagtt   1140
ttagagaaca attgttataa ttaaatgata aggtagaata tttctgcata taaattctgg   1200
ctggcgtgga aatattctta ttggtagaaa caactacatc ctggtcatca tcctgccttt   1260
ctctttatgg ttacaatgat atacactgtt tgagatgagg ataaaatact ctgagtccaa   1320
accgggcccc tctgctaacc atgttcatgc cttcttcttt ttcctacagc tcctgggcaa   1380
cgtgctggtt attgtgctgt ctcatcattt tggcaaagaa ttgtaatacg actcactata   1440
gggcgaattg atatgtctag attagataaa agtaaagtga ttaacagcgc attagagctg   1500
cttaatgagg tcggaatcga aggtttaaca acccgtaaac tcgcccagaa gctaggtgta   1560
gagcagccta cattgtattg gcatgtaaaa ataagcggg ctttgctcga cgccttagcc   1620
attgagatgt tagataggca ccatactcac ttttgcccctt tagaagggga aagctggcaa   1680
gattttttac gtaataacgc taaaagtttt agatgtgctt tactaagtca tcgcgatgga   1740
gcaaaagtac atttaggtac acggcctaca gaaaaacagt atgaaactct cgaaaatcaa   1800
ttagcctttt tatgccaaca aggttttca ctagagaatg cattatatgc actcagcgct   1860
gtggggcatt ttactttagg ttgcgtattg gaagatcaag agcatcaagt cgctaaagaa   1920
gaaagggaaa cacctactac tgatagtatg ccgccattat tacgacaagc tatcgaatta   1980
tttgatcacc aaggtgcaga gccagccttc ttattcggcc ttgaattgat catatgcgga   2040
ttagaaaaac aacttaaatg tgaaagtggg tccgcgtaca gcggatcccg ggaattcaga   2100
tcttattaaa gcagaacttg tttattgcag cttataatgg ttacaaataa agcaatagca   2160
tcacaaattt cacaaataaa gcattttttt cactgcattc tagttgtggt ttgtccaaac   2220
tcatcaatgt atcttatcat gtctgg                                        2246
```

<210> SEQ ID NO 14
<211> LENGTH: 5646
<212> TYPE: DNA
<213> ORGANISM: Artificial Sequence
<220> FEATURE:
<223> OTHER INFORMATION: DNA sequence encoding influenza H3 and N2, including the 5' and 3' expression control region

<400> SEQUENCE: 14

```
gttgacattg attattgact agttattaat agtaatcaat tacggggtca ttagttcata     60
gcccatatat ggagttccgc gttacataac ttacggtaaa tggcccgcct ggctgaccgc    120
ccaacgaccc ccgcccattg acgtcaataa tgacgtatgt tcccatagta acgccaatag    180
ggactttcca ttgacgtcaa tgggtggagt atttacggta aactgcccac ttggcagtac    240
atcaagtgta tcatatgcca agtacgcccc ctattgacgt caatgacggt aaatggcccg    300
cctggcatta tgcccagtac atgaccttat gggactttcc tacttggcag tacatctacg    360
tattagtcat cgctattacc atggtgatgc ggttttggca gtacatcaat gggcgtggat    420
agcggtttga ctcacgggga tttccaagtc tccaccccat tgacgtcaat gggagtttgt    480
tttggcacca aaatcaacgg gactttccaa aatgtcgtaa caactccgcc ccattgacgc    540
aaatgggcgg taggcgtgta cggtgggagg tctatataag cagagctctc cctatcagtg    600
```

```
atagagatct ccctatcagt gatagagatc gtcgacgagc tcgtttagtg aaccgtcaga    660
tcgcctggag acgccatcca cgctgttttg acctccatag aagacaccgg gaccgatcca    720
gcctccggac tctagcgttt aaacttaagc ttggtaccga gctcggatcc cttgcagaag    780
ttggtcgtga ggcactgggc aggtaagtat caaggttaca agacaggttt aaggagacca    840
atagaaactg ggcttgtcga gacagagaag actcttgcgt ttctgatagg cacctattgg    900
tcttactgac atccactttg cctttctctc cacaggtgtc cactcccagt tcaattacag    960
ctcttaaggc tagagtactt aatacgactc actataggct agaatgaatc caaatcaaaa   1020
gataataacg attggctctg tttctctcac catttccaca atatgcttct tcatgcaaat   1080
tgccatcttg ataactactg taacattgca tttcaagcaa tatgaattca actccccccc   1140
aaacaaccaa gtgatgctgt gtgaaccaac aataatagaa agaaacataa cagagatagt   1200
gtatctgacc aacaccacca tagagaagga aatatgcccc aaactagcag aatacagaaa   1260
ttggtcaaaa ccgcaatgta acattacagg atttgcacct ttttctaagg acaattcgat   1320 taggcttcc gctggtgggg acatctgggt gacaagagaa ccttatgtgt catgcgatcc   1380
tgacaagtgt tatcaatttg cccttggaca gggaacaaca ctaaacaacg tgcattcaaa   1440
tgacacagta catgatagga ccccttatcg gaccctattg atgaatgagt taggtgttcc   1500
atttcatctg gggaccaagc aagtgtgcat agcatggtcc agctcaagtt gtcacgatgg   1560
aaaagcatgg ctgcatgttt gtgtaacggg ggatgataaa aatgcaactg ctagcttcat   1620
ttacaatggg aggcttgtag atagtattgt ttcgtggtcc aaagaaatcc tcaggaccca   1680
ggagtcagaa tgcgtttgta tcaatggaac ttgtacagta gtaatgactg atgggagtgc   1740
ttcaggaaaa gctgatacta aaatactatt cattgaggag gggaaaatcg ttcatactag   1800
cacattgtca ggaagtgctc agcatgtcga ggagtgttcc tgctatccta gatatcctgg   1860
tgtcagatgt gtctgcagag acaactggaa aggctccaat aggcccatag tagatataaa   1920
cataaaggat tatagcattg tttccagtta tgtgtgctca ggacttgttg gagacacacc   1980
cagaaaaaac gacagctcca gcagtggcca ttgcttggat cctaacaatg aagaaggtgg   2040
tcatggagtg aaaggctggg cctttgatga tggaaatgac gtgtgatgg gaagaacgat   2100 cagcgagaag ttacgctcag gatatgaaac cttcaaagtc attgaaggct ggtccaaccc   2160
taattccaaa ttgcagataa ataggcaagt catagttgac agaggtaata ggtccggtta   2220
ttctggtatt ttctctgttg aaggcaaaag ctgcatcaat cggtgctttt atgtggagtt   2280
gataagggga agaaaagagg aaactgaagt cttgtggacc tcaaacagta ttgttgtgtt   2340
ttgtggcacc tcaggtacat atggaacagg ctcatggcct gatgggcgg acatcaatct   2400 catgcctata taatctagag ggcccgttta aaccgctga tcagcctcga ctgtgccttc   2460
tagttgccag ccatctgttg tttgcccctc ccccgtgcct tccttgaccc tggaaggtgc   2520
cactcccact gtccttttcct aataaaatga ggaaattgca tcgcattgtc tgagtaggtg   2580
tcattctatt ctggggggtg gggtggggca ggacagcaag ggggaggatt gggaagacaa   2640
tagcaggcat gctggggatg cggtgggctc tatggcacgc gttgacattg attattgact   2700
agttattaat agtaatcaat tacggggtca ttagttcata gcccatatat ggagttccgc   2760
gttacataac ttacggtaaa tggcccgcct ggctgaccgc ccaacgaccc ccgcccattg   2820
acgtcaataa tgacgtatgt tcccatagta acgccaatag ggactttcca ttgacgtcaa   2880
tgggtggagt atttacggta aactgcccac ttggcagtac atcaagtgta tcatatgcca   2940
```

```
agtacgcccc ctattgacgt caatgacggt aaatggcccg cctggcatta tgcccagtac   3000
atgaccttat gggactttcc tacttggcag tacatctacg tattagtcat cgctattacc   3060
atggtgatgc ggttttggca gtacatcaat gggcgtggat agcggtttga ctcacgggga   3120
tttccaagtc tccaccccat tgacgtcaat gggagtttgt tttggcacca aaatcaacgg   3180
gactttccaa aatgtcgtaa caactccgcc ccattgacgc aaatgggcgg taggcgtgta   3240
cggtgggagg tctatataag cagagctctc cctatcagtg atagagatct ccctatcagt   3300
gatagagatc gtcgacgagc tcgtttagtg aaccgtcaga tcgcctggag acgccatcca   3360
cgctgttttg acctccatag aagacaccgg gaccgatcca gcctccggac tctagcgttt   3420
aaacttaagc ttggtaccga gctcggatcc cttgcagaag ttggtcgtga ggcactgggc   3480
aggtaagtat caaggttaca agacaggttt aaggagacca atagaaactg gcttgtcga   3540 gacagagaag actcttgcgt ttctgatagg cacctattgg tcttactgac atccactttg   3600
cctttctctc cacaggtgtc cactcccagt tcaattacag ctcttaaggc tagagtactt   3660
aatacgactc actataggct agcatgaaga ctatcattgc tttgagctac attctatgtc   3720
tggttttcgc tcaaaaactt cccggaaatg acaacagcac ggcaacgctg tgccttgggc   3780
atcatgcagt accaaacgga acgatagtga aaacaatcac gaatgaccaa attgaagtta   3840
ctaatgctac tgagctggtt cagagttcct caacaggtgg aatatgcgac agtcctcatc   3900
agatccttga tggagaaaac tgcacactaa tagatgctct attgggagac cctcagtgtg   3960
atggcttcca aaataagaaa tgggaccttt ttgttgaacg cagcaaagcc tacagcaact   4020 gttacccttta tgatgtgccg gattatgcct cccttaggtc actagttgcc tcatccggca   4080
cactggagtt taacaatgaa agcttcaatt ggactggagt cactcaaaat ggaacaagct   4140
ctgcttgcaa aaggagatct aataacagtt tctttagtag attgaattgg ttgacccact   4200
taaaattcaa atacccagca ttgaacgtga ctatgccaaa caatgaaaaa tttgacaaat   4260
tgtacatttg gggggttcac cacccgggta cggacaatga ccaaatcttc ctgtatgctc   4320
aagcatcagg aagaatcaca gtctctacca aaagaagcca acaaactgta atcccgaata   4380
tcggatctag acccagagta agggatatcc ccagcagaat aagcatctat ggacaaatag   4440
taaaaccggg agacatactt ttgattaaca gcacagggaa tctaattgct cctagggggtt   4500 acttcaaaat acgaagtggg aaaagctcaa taatgagatc agatgcaccc attggcaaat   4560
gcaattctga atgcatcact ccaaatggaa gcattcccaa tgacaaacca tttcaaaatg   4620
taaacaggat cacatatggg gcctgtccca gatatgttaa gcaaaacact ctgaaattgg   4680
caacagggat gcgaaatgta ccagagaaac aaactagagg catatttggc gcaatcgcgg   4740
gtttcataga aaatggttgg gagggaatgg tggatggttg gtacggtttc aggcatcaaa   4800
attctgaggg aataggacaa gcagcagatc tcaaaagcac tcaagcagca atcaatcaaa   4860
tcaatgggaa gctgaatagg ttgatcggga aaaccaacga gaaattccat cagattgaaa   4920
aagaattctc agaagtagaa gggagaattc aggacctcga gaaatatgtt gaggacacta   4980
aaatagatct ctggtcatac aacgcggagc ttcttgttgc cctggagaac caacatacaa   5040
ttgatctaac tgactcagaa atgaacaaac tgtttgaaag aacaaagaag caactgaggg   5100
aaaatgctga ggatatgggc aatggttgtt tcaaaatata ccacaaatgt gacaatgcct   5160
gcataggatc aatcagaaat ggaacttatg accatgatgt atacagagat gaagcattaa   5220
acaaccggtt ccagatcaaa ggcgttgagc tgaagtcagg atacaaagat tggatcctat   5280
ggatttcctt tgccatatca tgttttttgc tttgtgttgc tttgttgggg ttcatcatgt   5340
```

```
gggcctgcca aaaaggcaac attaggtgca acatttgcat ttgagctaga gggcccgttt      5400
aaacccgctg atcagcctcg actgtgcctt ctagttgcca gccatctgtt gtttgccct       5460 cccccgtgcc ttccttgacc ctggaaggtg ccactcccac tgtcctttcc taataaaatg      5520
aggaaattgc atcgcattgt ctgagtaggt gtcattctat tctgggggt ggggtggggc       5580 aggacagcaa gggggaggat tgggaagaca atagcaggca tgctggggat gcggtgggct      5640
ctatgg                                                                 5646
```

<210> SEQ ID NO 15
<211> LENGTH: 5598
<212> TYPE: DNA
<213> ORGANISM: Artificial Sequence
<220> FEATURE:
<223> OTHER INFORMATION: DNA sequence encoding influenza H5 and N1,
      including the 5' and 3' expression control region

<400> SEQUENCE: 15

```
gttgacattg attattgact agttattaat agtaatcaat tacggggtca ttagttcata        60
gcccatatat ggagttccgc gttacataac ttacggtaaa tggcccgcct ggctgaccgc       120
ccaacgaccc ccgcccattg acgtcaataa tgacgtatgt tcccatagta acgccaatag       180
ggactttcca ttgacgtcaa tgggtggagt atttacggta aactgcccac ttggcagtac       240
atcaagtgta tcatatgcca agtacgcccc ctattgacgt caatgacggt aaatggcccg       300
cctggcatta tgcccagtac atgaccttat gggactttcc tacttggcag tacatctacg       360
tattagtcat cgctattacc atggtgatgc ggttttggca gtacatcaat gggcgtggat       420
agcggtttga ctcacgggga tttccaagtc tccaccccat tgacgtcaat gggagtttgt       480
tttggcacca aaatcaacgg gactttccaa aatgtcgtaa caactccgcc ccattgacgc       540
aaatgggcgg taggcgtgta cggtgggagg tctatataag cagagctctc cctatcagtg       600
atagagatct cccatcagt gatagagatc gtcgacgagc tcgtttagtg aaccgtcaga       660
tcgcctggag acgccatcca cgctgttttg acctccatag aagacaccgg gaccgatcca       720
gcctccggac tctagcgttt aaacttaagc ttggtaccga gctcggatcc cttgcagaag       780
ttggtcgtga ggcactgggc aggtaagtat caaggttaca agacaggttt aaggagacca       840
atagaaactg gcttgtcga cagagaag actcttgcgt ttctgatagg cacctattgg         900
tcttactgac atccactttg cctttctctc cacaggtgtc cactcccagt tcaattacag      960
ctcttaaggc tagagtactt aatacgactc actataggct agaatgaacc ccaaccagaa     1020
gatcatcacc atcggctcca tctgcatggt gaccggtatc gtgtccctga tgctgcagat    1080
cggtaacatg atctccatct gggtgtccca ctccatccac accggtaacc agcaccagtc    1140
cgagcccatc tccaacacca gttcctcac cgagaaggct gtggcttccg tgaagctggc   1200
tggtaactcc tccctgtgcc ccatcaacgg ttgggctgtg tactccaagg acaactccat    1260
ccgtatcggt tccaagggtg acgtgttcgt gatccgtgag cccttcatct cctgctccca    1320
cctggagtgc cgtaccttct tcctgaccca gggtgctctg ctgaacgaca agcactccaa    1380
cggcaccgtg aaggaccgtt cccccaccg taccctgatg tcctgccccg tgggcgaggc    1440
tccctccccc tacaactccc gtttcgagtc cgtggcttgg tccgcttccg cttgccacga    1500
cggcacctct ggctgaccca tcggtatctc cggtcccgac aacggtgctg tggctgtggt    1560
gaagtacaac ggcatcatca ccgacaccat caagtcctgg cgtaacaaca tcctgcgtac    1620
ccaagagtcc gagtgcgct gcgtgaacgg ttcctgcttc accgtgatga ccgacggtcc    1680
```

| | | | | |
|---|---|---|---|---|
| ctccaacggc | caggcttccc | acaagatctt | caagatggag | aagggcaagg tggtgaagtc | 1740 |
| cgtggagctg | gacgctccca | actaccacta | cgaggagtgc | tcttgctacc ccgacgctgg | 1800 |
| cgagatcacc | tgcgtgtgcc | gtgacaactg | gcacggttcc | aaccgtccct gggtgtcctt | 1860 |
| caaccagaac | ctggagtacc | agatcggtta | catctgctcc | ggcgtgttcg gtgacaaccc | 1920 |
| ccgtcccaac | gacggaaccg | gttcttgcgg | tcccgtgtcc | tccaacggtg cttacggtgt | 1980 |
| caagggcttc | tccttcaagt | acggtaacgg | tgtctggatc | ggtcgtacca agtccaccaa | 2040 |
| ctcccgctcc | ggtttcgaga | tgatctggga | ccccaacggt | tggaccgaga ccgactcctc | 2100 |
| cttctccgtg | aagcaggaca | tcgtggctat | caccgactgg | tccggttact ccggttcctt | 2160 |
| cgtgcagcac | cccgagctga | ccggtctgga | ctgtatccgt | ccctgcttct gggtggagct | 2220 |
| gatccgtggt | cgtcccaagg | agtccaccat | ctggacctcc | ggctcctcca tctctttctg | 2280 |
| cggtgtgaac | tccgacaccg | tgggctggtc | ctggcccgac | ggtgccgagc tgcccttcac | 2340 |
| catcgacaag | taggcggccg | cgggcccgtt | taaacccgct | gatcagcctc gactgtgcct | 2400 |
| tctagttgcc | agccatctgt | tgtttgcccc | tcccccgtgc | cttccttgac cctggaaggt | 2460 |
| gccactccca | ctgtcctttc | ctaataaaat | gaggaaattg | catcgcattg tctgagtagg | 2520 |
| tgtcattcta | ttctgggggg | tggggtgggg | caggacagca | agggggagga ttgggaagac | 2580 |
| aatagcaggc | atgctgggga | tgcggtgggc | tctatggacg | cgttgacatt gattattgac | 2640 |
| tagttattaa | tagtaatcaa | ttacggggtc | attagttcat | agcccatata tggagttccg | 2700 |
| cgttacataa | cttacggtaa | atggcccgcc | tggctgaccg | cccaacgacc cccgcccatt | 2760 |
| gacgtcaata | atgacgtatg | ttcccatagt | aacgccaata | gggactttcc attgacgtca | 2820 |
| atgggtggag | tatttacggt | aaactgccca | cttggcagta | catcaagtgt atcatatgcc | 2880 |
| aagtacgccc | cctattgacg | tcaatgacgg | taaatggccc | gcctggcatt atgcccagta | 2940 |
| catgacctta | tgggactttc | ctacttggca | gtacatctac | gtattagtca tcgctattac | 3000 |
| catggtgatg | cggttttggc | agtacatcaa | tgggcgtgga | tagcggtttg actcacgggg | 3060 |
| atttccaagt | ctccacccca | ttgacgtcaa | tgggagtttg | ttttggcacc aaaatcaacg | 3120 |
| ggactttcca | aaatgtcgta | acaactccgc | cccattgacg | caaatgggcg gtaggcgtgt | 3180 |
| acggtgggag | gtctatataa | gcagagctct | ccctatcagt | gatagagatc tccctatcag | 3240 |
| tgatagagat | cgtcgacgag | ctcgtttagt | gaaccgtcag | atcgcctgga gacgccatcc | 3300 |
| acgctgtttt | gacctccata | gaagacaccg | ggaccgatcc | agcctccgga ctctagcgtt | 3360 |
| taaacttaag | cttggtaccg | agctcggatc | ccttgcagaa | gttggtcgtg aggcactggg | 3420 |
| caggtaagta | tcaaggttac | aagacaggtt | taaggagacc | aatagaaact gggcttgtcg | 3480 |
| agacagagaa | gactcttgcg | tttctgatag | gcacctattg | gtcttactga catccacttt | 3540 |
| gcctttctct | ccacaggtgt | ccactcccag | ttcaattaca | gctcttaagg ctagagtact | 3600 |
| taatacgact | cactataggc | tagcatggag | aagatcgtgc | tgctgttcgc tatcgtgtcc | 3660 |
| ctggtgaagt | ccgaccagat | ctgcatcggt | taccacgcta | caaactccac cgagcaggtg | 3720 |
| gacaccatca | tggagaagaa | cgtcaccgtg | acccacgctc | aggacatcct ggaaaagacc | 3780 |
| cacaacggca | agctgtgcga | cctggacggt | gtcaagcccc | tgatcctgcg tgactgctcc | 3840 |
| gtggctggtt | ggctgctggg | taaccccatg | tgcgacgagt | tcatcaacgt gcccgagtgg | 3900 |
| tcctacatcg | tggagaaggc | taaccccgtg | aacgacctgt | gctacccegg tgacttcaac | 3960 |
| gactacgagg | agctgaagca | cctgctgtcc | cgtatcaacc | acttcgagaa gatccagatc | 4020 |

```
atccccaagt cctcttggct gtcccacgag gcttccctgg gcgtgtcctc cgcttgccca    4080 tacccagggca agtccagctt cttccgtaac gtggtgtggc tgatcaagaa gaactctacc    4140
taccccacca tcaagcgttc ctacaacaac accaaccagg aggacctgct ggtcctgtgg    4200
ggtatccacc accccaacga cgctgccgag cagaccaagc tgtaccagaa ccccaccacc    4260
tacatctccg tgggcacctc cacccctgaac cagcgtctgg tgccccgtat cgctacccgt    4320
tccaaggtga acggccagtc cggtcgtatg gagttcttct ggaccatcct gaagcctaac    4380
gacgctatca acttcgagtc caacggcaac ttcatcgctc ccgagtacgc ttacaagatc    4440
gtgaagaagg gcgactccac catcatgaag tccgagctgg agtacggtaa ctgcaacacc    4500
aagtgccaga ccccccatggg tgctatcaac tcctccatgc ccttccacaa catccacccc    4560
ctgaccatcg gcgagtgccc caagtacgtg aagtccaacc gtctggtgct ggctaccggt    4620
ctgcgtaact cccccccagcg tgagcgtcgt aagaagcgtg gtctgttcgg cgctatcgct    4680
ggtttcatcg agggcggttg gcagggcatg gtggacggtt ggtacggtta ccaccactct    4740
aacgagcagg gttccggtta cgctgctgac aaggagtcca cccagaaggc tatcgacggc    4800
gtcaccaaca aggtgaactc catcatcgac aagatgaaca cccagttcga ggctgtgggt    4860
cgtgagttca caaacctgga gcgtcgtatc gagaacctga acaagaagat ggaggacggt    4920
ttcctggacg tgtggaccta caacgccgag ctgctggtgc tgatggagaa cgagcgtacc    4980
ctggacttcc acgactccaa cgtgaagaac ctgtacgaca aggtccgcct gcagctgcgt    5040
gacaacgcta aggagctggg taacggttgc ttcgagttct accacaagtg cgacaacgag    5100
tgcatggagt ccgtgcgtaa cggcacctac gactacccccc agtactccga ggaggccaag    5160
ctgaagcgtg gcgagatctc cggcgtgaag ctggagtcca tcggtatcta ccagatcctg    5220
tccatctact ccaccgtggc ttcctccctg gctctggcta tcatggtggc tggtctgtcc    5280
ctgtggatgt gctccaacgg ttccctgcag tgccgtatct gcatctaggc ggccgcgcta    5340
gagggcccgt ttaaacccgc tgatcagcct cgactgtgcc ttctagttgc cagccatctg    5400
ttgtttgccc ctcccccgtg ccttccttga ccctggaagg tgccactccc actgtccttt    5460
cctaataaaa tgaggaaatt gcatcgcatt gtctgagtag gtgtcattct attctggggg    5520
gtggggtggg gcaggacagc aagggggagg attgggaaga caatagcagg catgctgggg    5580
atgcggtggg ctctatgg                                                  5598
```

<210> SEQ ID NO 16
<211> LENGTH: 26
<212> TYPE: DNA
<213> ORGANISM: Artificial Sequence
<220> FEATURE:
<223> OTHER INFORMATION: RT-PCR primer

<400> SEQUENCE: 16

```
attaggcttt ccgctggtgg ggacat                                           26
```

<210> SEQ ID NO 17
<211> LENGTH: 28
<212> TYPE: DNA
<213> ORGANISM: Artificial Sequence
<220> FEATURE:
<223> OTHER INFORMATION: RT-PCR primer

<400> SEQUENCE: 17

```
gcattctgac tcctgggtcc tgaggatt                                         28
```

HIGH-YIELD TRANSGENIC MAMMALIAN EXPRESSION SYSTEM FOR GENERATING VIRUS-LIKE PARTICLES

REFERENCE TO RELATED APPLICATIONS

This application is a continuation-in-part patent application of U.S. patent application Ser. No. 11/515,843, filed on Sep. 5, 2006, which was published as US 20080063664 on Mar. 13, 2008, now abandoned the disclosure of which is incorporated herein by reference.

FIELD OF THE INVENTION

The present invention relates to a mammalian expression system for generating virus-like particles (VLPs), and uses of VLPs generated by the mammalian expression system.

BACKGROUND OF THE INVENTION

The spread of a newly evolved coronavirus (CoV) caused a global threat of severe acute respiratory syndrome (SARS) pandemics in 2003 (Kuiken, T. et al., 2003, *Lancet* 362: 263-270). Coronaviruses are taxonomically classified in the order Nidovirales, based on features of their genome organization and replication strategy. As with other coronaviruses, SARS-CoV has the morphology of enveloped particles with typical peripheral projections, termed "corona" or "spikes," surrounding the surface of a viral core (Ksiazek, T. G. et al., 2003, *N Engl J Med* 348: 1953-1966; Lin, Y. et al., 2004, *Antivir Ther* 9: 287-289). Outside the coronavirus particle core is a layer of lipid envelope containing mainly three membrane proteins, the most abundant M (membrane) protein, the small E (envelope) protein, and the S (spike) protein. The homo-trimers of the S protein collectively form the aforementioned corona, which is involved in viral binding to host receptors, membrane fusion for viral entry, cell-to-cell spread and tissue tropism of coronaviruses. The viral core inside the envelope, termed nucleocapsid, harbors a positive-strand viral genome RNA of approximately 30 kb packaged by the N (nucleocapsid) protein.

Unlike other human coronaviruses, such as HCoV-229E and HCoV-OC43, that can cause only symptoms like the common cold, SARS-CoV causes a highly transmittable, severe and virulent disease that can often be lethal in adults and especially the elderly. Research and clinical interest on SARS-CoV has grown rapidly owing to the high infectivity and mortality. There is especially an urgent need for an effective and safe vaccine against SARS-CoV to deal with possible future reemergence of the SARS epidemics.

Most antiviral vaccines currently in use contain whole viruses, either inactivated or live-attenuated. Inactivated, or killed, viruses are treated chemically or by irradiation to disable their replication and are generally safe and easy to make. While eliciting neutralizing antibodies, they are unlikely to deliver viral antigens to cytosol for cytotoxic CD8+ T lymphocytes (CTLs) activation, which is critical to defend animals from infection. Live-attenuated vaccines are significantly more potent than killed vaccines. However, live-attenuated viruses pose the risk of reversion or recombination with circulating wild type into a virulent strain. Moreover, the manufacture of vaccines based on whole viruses also carries the risk of viral escape.

To avoid the danger of using the whole virus (such as killed or attenuated viruses) as a vaccine, recombinant viral proteins have been pursued not only as research tools but also as potential advanced subunit vaccines. However, subunit vaccines are known to suffer often from poor immunogenicity, owing to incorrect folding, poor antigen presentation, or difference in carbohydrate and lipid composition. Virus-like particles (VLPs) are self-assembled microscopic antigenic structures that resemble a virus in size and shape but lack genetic materials. VLPs can concurrently present viral proteins, carbohydrates and lipids in a similar and authentic conformation and thus have been viewed as an ideal vaccine against viruses (McGuigan, L. C. et al., 1993, *Vaccine* 11: 675-678). VLPs display intact viral antigens on the surface in a repeated arrangement, with which they afford the natural binding of a large viral entity to membrane receptors of antigen-presenting cells (APCs), such as dendritic cells (DCs). DC-targeted uptake of VLPs enables potent stimulation of CD4+ T cells against VLP-associated antigens. Besides stimulating humoral immunity, VLPs are permissive for cross-presentation in DCs that allows priming of CTL response with VLP-associated antigens (Moron, G. et al., 2002, *J Exp Med* 195: 1233-45).

VLPs for over thirty different viruses have been generated in insect and mammalian systems for vaccine purpose (Noad, R. and Roy, P., 2003, *Trends Microbiol* 11: 438-44). It has been shown that cellular expression of the M protein accompanied by the E protein of coronaviruses was a minimal requirement and sufficient for the assembly of VLPs (Vennema, H. et al., 1996, *EMBO J.* 15: 2020-2028). While being dispensable in forming VLPs, the S protein can be integrated into the VLPs whenever available (Godeke, G. J. et al., 2000, *J Virol* 74: 1566-1571).

Researchers have used baculovirus expression systems to produce SARS VLPs (Ho, Y. et al., 2004, *Biochem Biophys Res Commun* 318: 833-838; Mortola, E. and Roy, P., 2004, *FEBS Lett* 576: 174-178). However, due to the intrinsic differences between insect cells and mammalian cells, the VLPs assembled in the insect (SF9) cells exhibited a size of 110 nm in diameter, which is much larger than the 78 nm of the authentic SARS-CoV virions (Lin, Y. et al., 2004, supra, and Ho, Y. et al., 2004, supra). Moreover, immunogenicity of the insect cell-based SARS-VLP remains uninvestigated. Other researchers also tried to use mammalian expression systems to produce SARS VLPs (Huang, Y. et al., 2004, *J Virol* 78: 12557-65). However, the extracellular release of VLPs is not efficient, and the yield of VLPs is not satisfying.

Therefore, there is still a need for an efficient method for the large-scale production of SARS VLPs in order to provide an effective and safe vaccine against SARS.

Influenza infection is a major threat to human health and results in significant morbidity and mortality worldwide. According to World Health Organization estimates, seasonal influenza epidemics influence 5~15% of the global populations annually and are responsible for more than 3-5 million hospitalizations and about 250,000 to 500,000 deaths per year (www.who.int/mediacentre/factsheets/fs211/en/index.html). Recently, in addition to the yearly circulating seasonal influenza variants caused by antigenic drift, other influenza virus strains with pandemic potential such as the highly pathogenic avian H5N1 or emerged novel A/H1N1 pose greater threats than in the past (www.who.int/csr/disease/avian_influenza/country/en/, and www.who.int/csr/don/2009_08_19/en/index.html) since they have become better adapted to humans by reassortment. The most efficient way of reducing the transmission of and the subsequent huge economic loss caused by seasonal or pandemic outbreaks of influenza is preventive vaccination. The manufacture of the current licensed influenza vaccines, either in the form of a split subvirion (disrupted, highly purified virus) or a subunit vaccine (purified hemagglutinin, HA, and neuraminidase, NA), is absolutely dependent on fertilized chicken eggs as a production bioreactor. This method has substantial limitations since the manufacturing capacity is restricted by the availability of eggs, which may be insufficient to meet the urgent requirements for vaccine during a pandemic [1,2,3]. In addition, these vaccines induce antibodies primarily to the viral HA and are efficacious in healthy adults, but display lower protective rates in high-risk groups (e.g., the elderly) and may be poorly immunogenic in young children. These problems are compounded once the wild population of virus undergoes significant antigenic drift in the HA component [1,2,4,5,6]. Consequently, the protective immunity elicited by inactivated vaccines is of too short a duration to protect from newly developed influenza variants. Therefore, the development of vaccines with cross-protective efficacy to allow a rapid response to influenza evolution and/or to prolong the efficacy of vaccination needs to be addressed.

Alternatively, an improvement in the preparation of seasonal influenza vaccines licensed in Europe uses reverse genetics in mammalian cell-based culture systems rather than in eggs [2]. Using mammalian cell culture systems such as Vero or MDCK cells as adaptive hosts for vaccine viruses has several advantages, not only increasing the flexibility and consistency of the manufacture process but also recovering the host-dependent specific glycosylation of viral antigens which may not be glycosylated properly in egg- or baculovirus-dependent systems. In eukaryotic cells, protein glycosylation is involved in correct folding or directing the cellular localization of newly translated proteins and plays important roles in protein function. Different glycosylation patterns underlie some of the differences between various strains of the influenza virus.

Recently, the use of noninfectious virus-like particles (VLPs) that self-assemble by spontaneous interactions of viral structural proteins has been considered to offer good potential for advanced vaccines for a wide range of viruses that cause disease in humans [7]. The VLP-based vaccine approach is an attractive alternative to replace or complement the conventional inactivated virus vaccines or subunit vaccines with improved safety and efficacy, especially for children and the elderly. It is worth noting that a VLP-based human papillomavirus (HPV) vaccine produced in yeast system which is capable of inducing protective immune response against the HPV responsible for cervical cancer was approved for the market in 2006 [8, 27, 28]. Influenza VLPs expressed by recombinant baculovirus systems that present multi-component antigens, including HA and matrix 1 (M1), with or without NA, and that are capable of inducing cognate or innate immune responses against homologous or heterologous strains of influenza virus, have been described [3,9,10,11,12,13,14, 29]. Clinical studies for baculovirus-expressed influenza VLPs are currently being undertaken.

In light of the great threats posed by seasonal and pandemic influenza infection, there is a need for further improved means for the development of flexible, effective, and safe vaccine for influenza infection.

BRIEF SUMMARY OF THE INVENTION

The present invention provides an efficient method for generating VLPs, wherein the resulting VLPs are highly immunogenic and can serve as a useful vaccine; particularly SARS VLPs for use as a vaccine against SARS, and influenza VLPs for use as a vaccine or to stimulate immune response against influenza infection.

A flexible platform based on the production of influenza VLPs from recombinant Vero cells presents a practical new approach to safe and effective vaccine production, which does not have the drawbacks of the egg-based or the baculovirus culture-based methodology, and is an alternative to the conventional reverse genetics approaches used in influenza vaccine manufacture.

In some embodiments of the present invention, there is provided a method for generating virus-like particles (VLPs) of a mammalian-hosted virus, the method comprising:

constructing a plasmid comprising a nucleotide sequence encoding a combination of at least two structural proteins of the virus;

transfecting Vero cells with the plasmid; and expressing the viral structural proteins in the transfected cells to generate VLPs of the virus.

In other embodiments of the present invention, there is provided a method for generating antibodies against SARS-CoV, comprising immunizing a mammal or bird with SARS-VLPs generated according to the present invention, and harvesting antibodies against the VLPs from the blood of the mammal or bird.

In further embodiments of the present invention, there is provided a method for detecting an infection of SARS-CoV in a subject, comprising contacting a serum sample from the subject with SARS-VLPs generated according to the present invention, and determining the presence in the sample of an antibody/antigen complex, whereby the presence of the complex indicates a positive result.

In further embodiments of the present invention, there is provided a method for detecting an infection of SARS-CoV in a subject, comprising contacting a tissue sample from the subject with antibodies against the SARS-VLPs generated according to the present invention, and determining the presence in the sample of an antibody/antigen complex, whereby the presence of the complex indicates a positive result.

In still other embodiments of the present invention, there is provided a method for preventing an infection of SARS-CoV in a subject, comprising immunizing the subject with SARS-VLPs generated according to the present invention.

In still other embodiments of the present invention, there is provided an immunogenic composition comprising SARS-VLPs generated according to the present invention.

A further aspect of the present invention relates to a method of preparing an influenza virus-like particle (VLP), the method comprising:

obtaining a founder Vero cell stably transfected with a sequence encoding an influenza M1 and a sequence encoding an influenza M2;

constructing at least one recombinant DNA molecule comprising a sequence encoding an influenza hemagglutinin (HA) and a sequence encoding an influenza neuraminidase (NA);

introducing the at least one recombinant DNA molecule into the founder Vero cell to obtain a co-expression Vero cell stably transfected with the sequences encoding the influenza M1 and the influenza M2, and further transfected with the sequences encoding the influenza HA and the influenza NA, wherein the expressions of the influenza M1, M2, HA and NA proteins in the co-expression Vero cell are controlled by one or more inducible expression systems;

culturing the co-expression Vero cell under conditions to allow expressions of the influenza M1, the influenza M2, the influenza HA and the influenza NA, and assembly of the VLP comprising the influenza M1, the influenza M2, the influenza HA and the influenza NA; and isolating the VLP from the culture supernatant of the co-expression Vero cell.

Another aspect of the present invention relates to a method of preparing an influenza virus-like particle (VLP), the method comprising:

obtaining a co-expression Vero cell stably transfected with a sequence encoding an influenza M1 and a sequence encoding an influenza M2, and further transfected with a sequence encoding an influenza hemagglutinin (HA) and a sequence encoding an influenza neuraminidase (NA), wherein the expressions of the influenza M1, M2, HA and NA proteins in the co-expression Vero cell are controlled by one or more inducible expression systems; and culturing the co-expression Vero cell under conditions to allow expressions of the influenza M1, the influenza M2, the influenza HA and the influenza NA, and assembly of the VLP comprising the influenza M1, the influenza M2, the influenza HA and the influenza NA; and isolating the VLP from the culture supernatant of the co-expression Vero cell.

Another aspect of the present invention relates to an influenza virus-like particle (VLP), comprising:

an influenza M1, an influenza M2, an influenza hemagglutinin (HA) and an influenza neuraminidase (NA), wherein the influenza proteins are recombinantly expressed from a Vero cell; and at least one cellular protein of the Vero cell.

Another aspect of the invention relates to a founder Vero cell that is a Vero cell stably transfected with a sequence encoding an influenza M1 and a sequence encoding an influenza M2, wherein the expressions of the influenza M1 and M2 proteins in the founder Vero cell are controlled by an inducible expression system. In one embodiment, the founder Vero cell is recombinantly made from Vero E6 cell.

Another aspect of the invention relates to a method of obtaining a founder Vero cell. The method comprises:

introducing into a Vero cell a sequence encoding an influenza M1 and a sequence encoding an influenza M2; and obtaining the founder Vero cell stably transfected with the sequence encoding the influenza M1 and the sequence encoding the influenza M2, wherein the expressions of the influenza M1 and M2 proteins in the founder Vero cell are controlled by an inducible expression system.

An embodiment of the invention relates to a co-expression Vero cell that is a Vero cell stably transfected with a sequence encoding an influenza M1 and a sequence encoding an influenza M2, and further transfected with a sequence encoding an influenza HA and a sequence encoding an influenza NA, wherein the expressions of the influenza M1, M2, HA and NA proteins in the co-expression Vero cell are controlled by one or more inducible expression systems. In one embodiment, the co-expression Vero cell is recombinantly made from Vero E6 cell.

Another embodiment of the invention relates to a method of obtaining a co-expression Vero cell. The method comprises:

obtaining a founder Vero cell stably transfected with a sequence encoding an influenza M1 and a sequence encoding an influenza M2;

introducing into the founder Vero cell a sequence encoding an influenza HA and a sequence encoding an influenza NA; and obtaining a co-expression Vero cell stably transfected with the sequence encoding the influenza M1 and the sequence encoding the influenza M2, and further transfected with the sequence encoding the influenza HA and the sequence encoding the influenza NA, wherein the expressions of the influenza M1, M2, HA and NA proteins in the co-expression Vero cell are controlled by one or more inducible expression systems.

Embodiments of the invention further relate to immunogenic compositions comprising the influenza VLPs according to embodiments of the present invention, and antibodies against the influenza VLPs according to embodiments of the present invention.

Methods related to the influenza VLPs, the immunogenic compositions and antibodies are also included in the present invention.

Other aspects, features and advantages of the invention will be apparent from the following disclosure, including the detailed description of the invention and its preferred embodiments and the appended claims.

BRIEF DESCRIPTION OF THE SEVERAL VIEWS OF THE DRAWINGS

The patent or application file contains at least one drawing executed in color. Copies of this patent or patent application publication with color drawings will be provided by the Office upon request and payment of the necessary fee.

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1 comprises FIGS. 1A and 1B. FIG. 1A comprises an illustration of the construction of the fluorescent SARS VLP-expressing plasmid. FIG. 1B comprises fluorescent images showing the locations of the expressed VLPs. Regarding FIG. 1A, two tet operator-regulated, CMV promoter-driven expression cassettes were constructed into the same plasmid for inducible expression of M-GFP fusion protein (i.e., the M protein fused with a green fluorescent protein (GFP)) and E protein from one cassette, and S protein from the other. FIG. 1B shows the results of the expression and assembly of fluorescent SARS VLPs in the VeroE6/S-MG-E-55 producer cell line, wherein cells were induced by adding 1 µg/ml doxycycline (Dox) to culture medium for 1 day, fixed, and then stained indirectly with antibodies specifically against M, GFP, S and E proteins as marked. The green fluorescence from GFP in the stained cells was scanned and merged for co-localization with different proteins contained in the VLP inside the producer cells.

FIG. 2 comprises FIGS. 2A-2D, and shows the results of the purification and characterization of Vero E6-secreted SARS-VLPs. Regarding FIG. 2A, secreted VLPs were purified by sucrose gradient ultra-centrifugation. Protein concentration (measured by Bradford Assay) and GFP fluorescence level in each fraction were plotted as marked. Regarding FIG. 2B, proteins contained in each fraction were analyzed by SDS-PAGE and Coomassie blue staining. Regarding FIG. 2C, identities of the protein bands marked in FIG. 2B were verified by western blot analysis using antibodies against S, M, E, or GFP proteins. FIG. 2D is an electron microscopic image of negatively stained SARS-VLPs (fractions 9 to 15 of FIG. 2B) purified by sucrose gradient from cell culture medium (the bar indicates a scale of 50 nm).

Figure 3A:
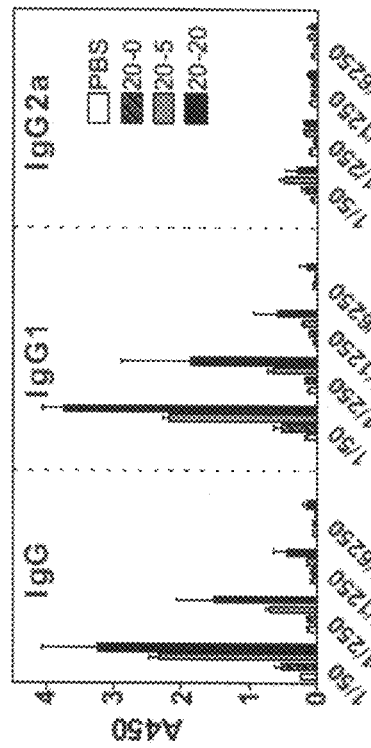
Figure 3B:
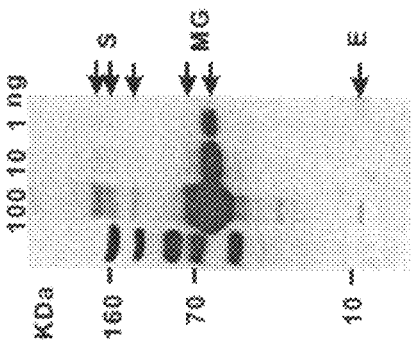
Figure 3C:
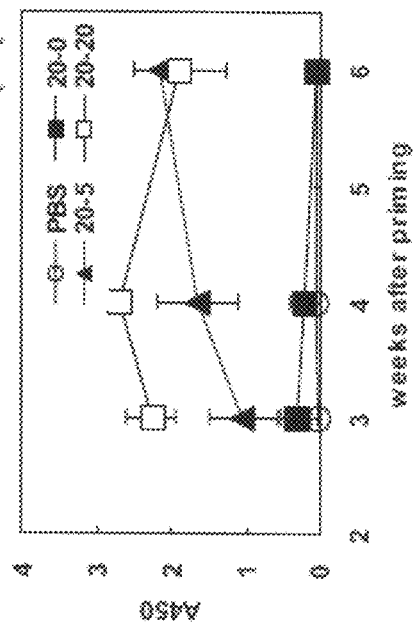
Figure 3D:
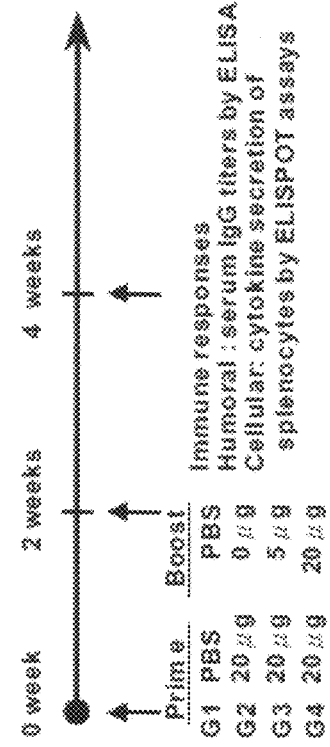
Figure 3E:
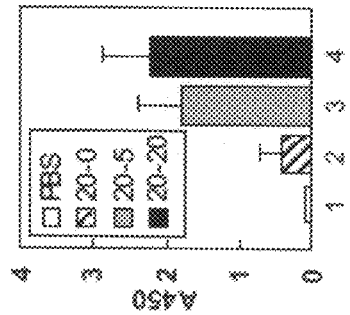

FIG. 3 comprises FIGS. 3A-3E and shows the results of immunization with SARS-VLPs induced humoral immune responses in mice. Regarding FIG. 3A, a diagram of immunization protocol, groups of four mice were subcutaneously injected with different dosage of SARS-VLPs at two time points as marked. Serum samples were examined for VLP-specific antibody responses in tested mice by ELISA after serial dilution. FIG. 3B shows graphs relating to ELISA titers of VLP-specific IgG, IgG1, and IgG2a using SARS-VLP as the capture antigen. Serum samples were collected on the 28th day after primary immunization. Dilution of test samples is marked on the X-axis. The background-subtracted absorbance (450 nm) was plotted as means±standard deviations (error bar). Presented data summarize the results of three different experiments. FIG. 3C is a graph that relates to cross-reaction of VLP-specific IgG antibodies with real SARS-CoV. Anti-sera as shown in FIG. 3B were diluted (1:250) in PBS. The SARS-specific antibody titer elicited by SARS-VLP vaccination was detected by a commercial SARS ELISA test kit (Euroimmun) according to the manufacture's protocol, except for a modification by replacing the anti-human IgG secondary antibody with anti-mouse IgG. Mean titer and standard deviation in each group of immunized mice was summarized and plotted as means±standard deviations. FIG. 3D is a graph relating to a time course of VLP-elicited antibody responses. Serum samples were collected from immunized mice at the indicated time points. Anti-sera were diluted (1:250) in PBS and titers of VLP-specific IgG were measured by ELISA analysis as in FIG. 3B. FIG. 3E relates to antigen determinants of VLP-elicited antibodies. Three doses (100, 10, 1 ng) of purified VLP were loaded as Western blot antigens. Anti-sera as shown in FIG. 3B were diluted (1:1000) in PBS and subjected to western blot analysis.

Figures 4A, 4B:
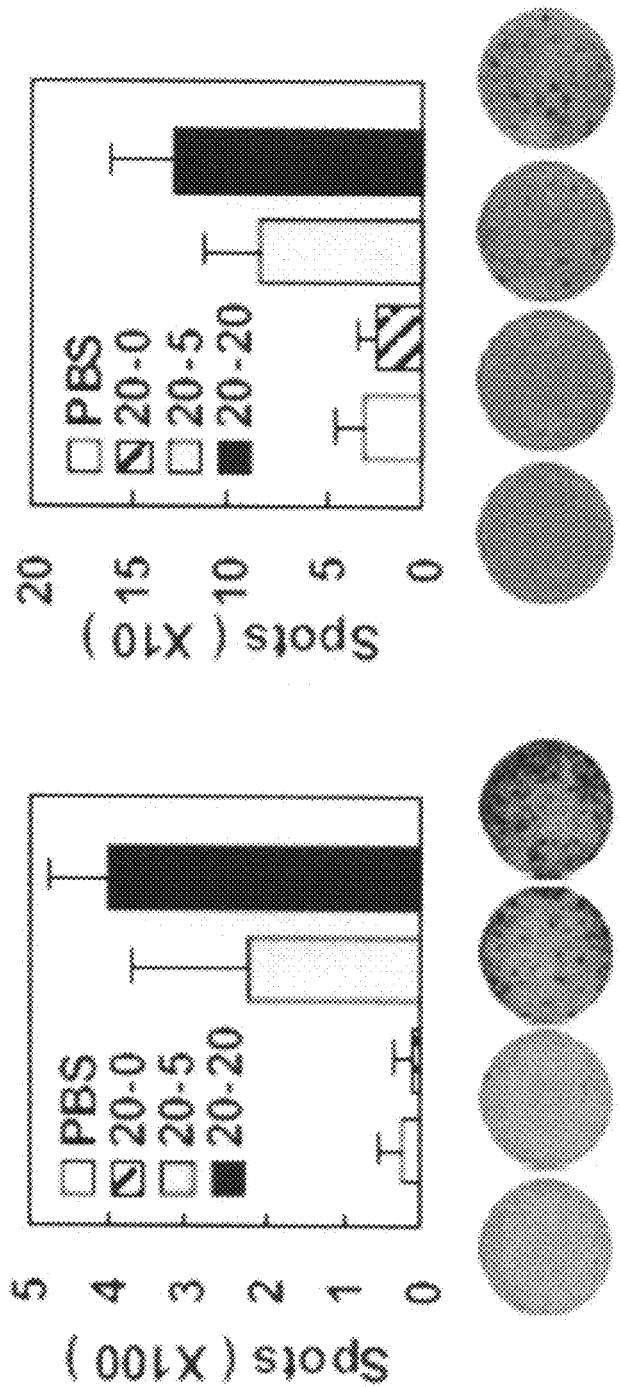
Figure 7A:
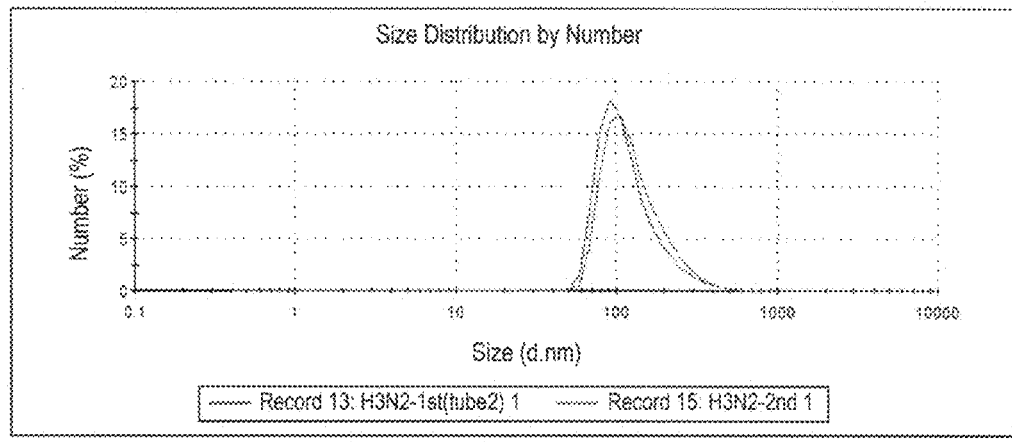
Figure 7B:
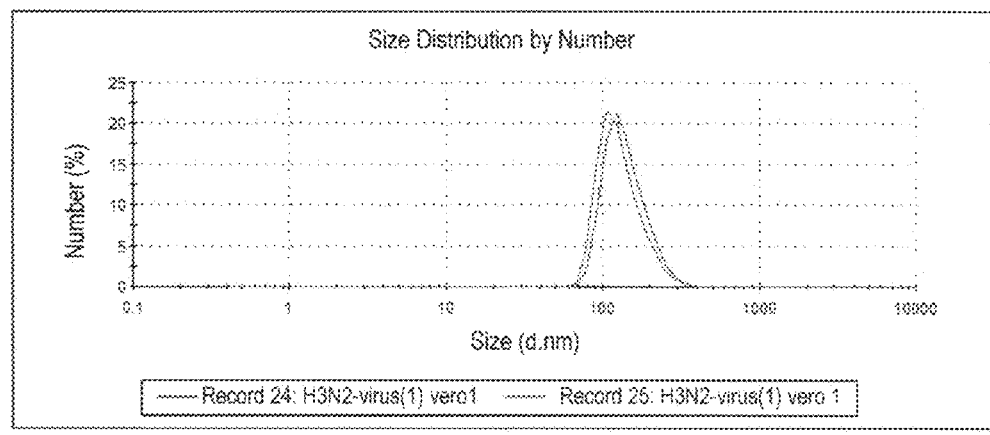

FIG. 4 comprises FIGS. 4A and 4B and relates to immunization with SARS-VLPs induced cellular immune responses in mice. Primary culture of splenocytes obtained from tested mice 28 days after priming as shown in FIG. 3B were re-stimulated with SARS-VLP for 40 hours. Responsive cells that secrete Interferon-γ (FIG. 4A) and interleukin-4 (FIG. 4B) were determined by ELISPOT assays. Presented data summarize the results of three different experiments as means±standard deviations (error bar).

FIG. 5 illustrates the construction and cellular expression of influenza virus-like particles (VLPs) in Vero cells:

FIG. 5A are diagrams of mammalian expression vectors of influenza VLPs, which indicate the arrangement of various genetic components including the CMV constitutive promoter (CMV), tetracycline repressor gene (TetR), polyadenylation signals (PA), CMV doxycycline (Dox)-inducible promoter (CMV-TO), chimeric intron (In), encephalomyocarditis virus internal ribosomal entry site (IRES), and coding sequences of influenza proteins (M1 and M2, matrix 1 and 2; HA, hemagglutinin; NA, neuraminidase);

FIGS. 5B and 5C are pictures showing expression of viral genes in selected quadruple VLP producer cells, where expressions of M1, M2, H3, H5, and N1 were detected by Western blot assays: the total cell lysates were extracted from VLP producing Vero cells without (−) or with (+) Dox induction, proteins in the cell lysates were separated by SDS-PAGE, then probed with respective specific antibodies against HA, NA, M1 and M2 in Western blot assays, molecular masses of expressed HA, NA, M1 and M2 are indicated on the right; expression of N2 (shown in FIG. 5B) without (−) or with (+) Dox induction was detected by RT-PCR; and FIGS. 5D and 5E show in vivo immunofluorescence staining of expressed viral proteins in VLP producing Vero cells with antibodies against HA and NA (red) as marked and counterstained with DAPI (blue).

FIG. 6 shows the morphology and antigen presence determinations of purified influenza VLPs produced by Vero cells:

FIGS. 6A and 6B are the pictures of purified secreted influenza VLPs under TEM: the secreted VLPs were purified by sucrose density gradient ultracentrifugation, negatively stained with 2% uranyl acetate, and observed by TEM at 100,000× magnification; pictures of the respective virus strains are also shown below the VLPs; and FIGS. 6C and 6D are pictures of purified secreted influenza VLPs from immunogold electron microscopy analysis: the primary antibodies used are labeled under individual panels; secondary antibody was goat anti-rabbit conjugated to 12 nm gold beads, bars represent 100 nm.

FIGS. 7A-D illustrate the dynamic light scattering (DLS) measurements of average particle sizes and distributions of H3N2 VLPs, H3N2 virus, H5N1 VLPs and H5N1 virus in solution, respectively: the average particle diameters of H3N2 VLPs and H5N1 VLPs in phosphate buffer (pH 7.4), at 25° C. were 108.2±17.9 nm (A) and 125.6±10.5 nm (C), respectively; the average particle diameters of H3N2 virus and H5N1 virus in phosphate buffer (pH 7.4), at 25° C. were 133.5±15.4 nm (B) and 104.1±12.4 nm (D), respectively; two representative determinations of different batches of VLPs or virus are shown as red and green lines; the size distribution of VLP populations ranged from 70 to 200 nm with a 95% confidence interval (CI).

FIG. 8 shows the characterization of purified influenza VLPs produced by Vero cells:

FIGS. 8A and 8C show pictures of SDS-PAGE analysis of H3N2 VLPs and H5N1 VLPs as compared with H3N2 virus and H5N1 virus, respectively: the total proteins of the VLPs or virus were resolved by SDS-PAGE in a 7.5-17.5% gradient gel and stained with Coomassie blue; each relevant band on the gel, as marked with an arrow and a number, was subjected to LC/MS/MS analysis to identify its composition; the identified viral protein bands of the VLPs are marked with parentheses in panels; and molecular masses of protein markers are labeled on the right;

FIGS. 8B and 8D show pictures of Western blot analyses of viral proteins in H3N2 VLPs and H5N1 VLPs as compared with H3N2 virus and H5N1 virus, respectively: after the SDS-PAGE described in FIGS. 8A and 8C, Western blot was performed with specific antibodies as labeled: the relative abundances of HA and NA, quantified by Chemigenius 2 (SYNGENE, Frederick, Md.) and GeneTools (version 3.07) software, were 4:1 for H3N2 VLPs and 3:2 for H5N1-VLPs; the HA protein attributes to 12.8% or 18% of total proteins in H3N2 VLPs or H5N1 VLPs, respectively; and FIG. 8E demonstrates the assessment of HA function by hemagglutination assay: the amounts of VLPs or virus used are indicated, in a twofold serial dilution; THE (buffer of VLPs) and PBS were included as the negative controls in the hemagglutination assays.

Figure 9:
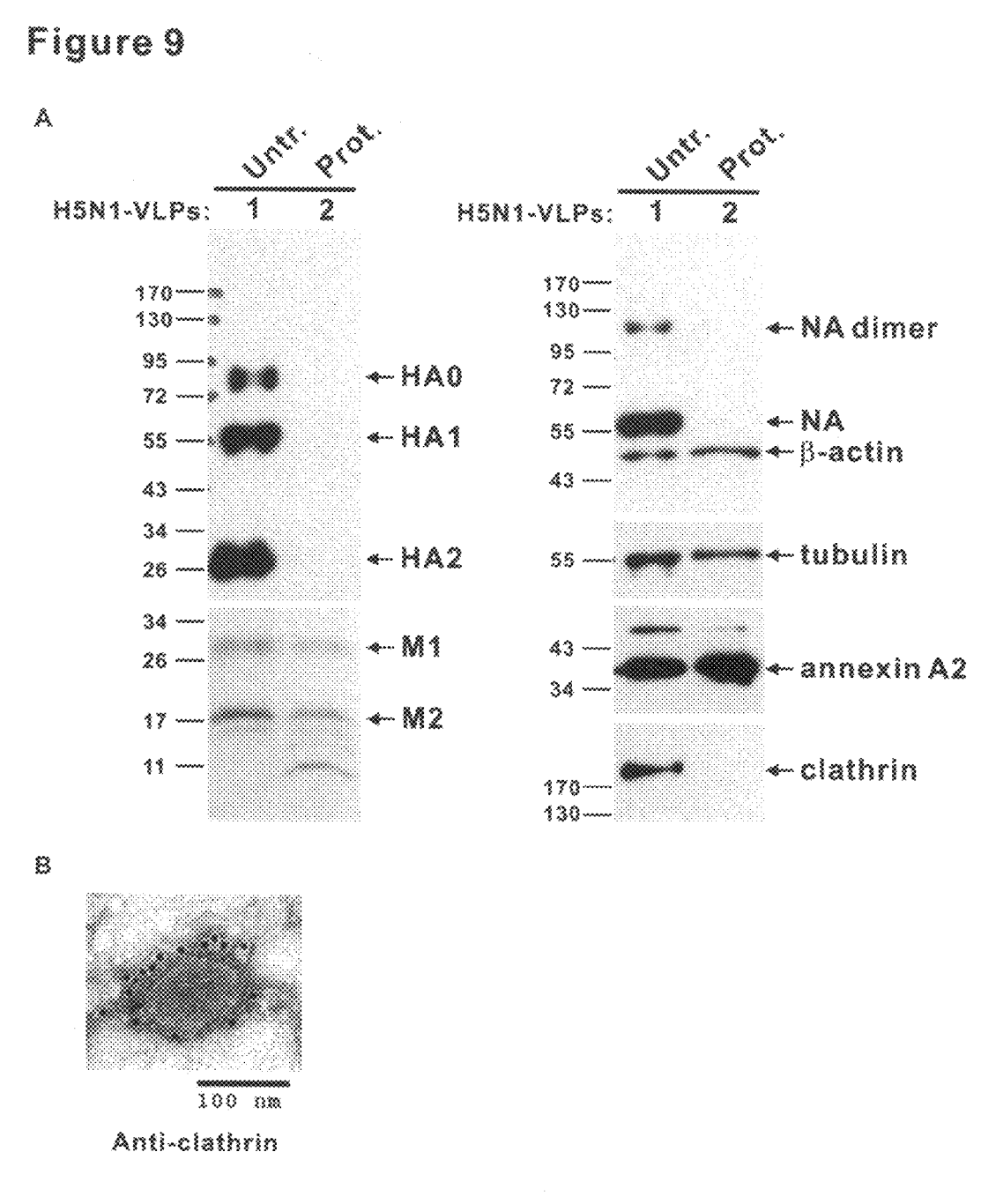

FIG. 9 shows specific integration of Vero cellular proteins in H5N1 VLPs:

FIG. 9A shows pictures of Western blot analyses of viral proteins (left) and Vero cell proteins (right) in H5N1 VLPs: purified VLPs were either mock-treated (Untr., lane 1) or digested overnight with typsin (Prot., lane 2) followed by purification with a 20% sucrose cushion; 2.5 μg each of the purified VLPs were further analyzed by SDS-PAGE followed by Western blotting with antibodies against the indicated proteins including HA, NA, M1, M2, β-actin, tubulin, annexin A2, and clathrin; molecular weight markers are marked on the left; and FIG. 9B shows immunogold labeling of clathrin on the surface of purified H5N1 VLPs: secreted VLPs purified from conditioned medium were immunogold labeled with antibody against clathrin, negatively stained with 2% uranyl acetate, and observed by electron microscopy (100,000× magnification); bar represents 100 nm.

FIG. 10 shows glycosylation profiling of HA and NA in influenza VLPs produced by Vero cells: mock-treated and deglycosylase-treated proteins of H5N1-VLPs were separated by SDS-PAGE, stained with Coomassie blue (A), and further analyzed by Western blotting using antibodies against H5 (B) and N1 (C); proteins of H5N1 virus were also analyzed by Western blotting using antibodies against H5 (B); mock-treated and deglycosylase-treated proteins of H3N2-VLPs or H3N2 virus were also analyzed by Western blotting using the antibody against H3 (D); the molecular markers are labeled on the left; the positions of PNGase F and Endo-H are indicated; the glycosylated HA1, HA2, NA, and H3 are labeled as HA1, HA2, NA and, H3, respectively; # represents glycosylated proteins harboring a residue moiety of complex-type glycans sensitive to PNGase F, but not Endo-H; π represents unknown posttranslational modifications on the NA of H5N1-VLPs.

Figure 11A:
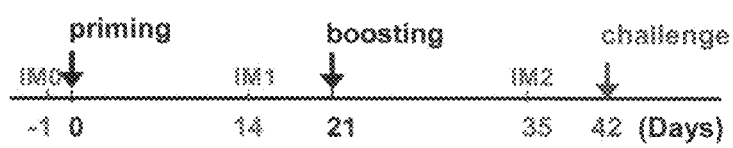
Figure 11B:
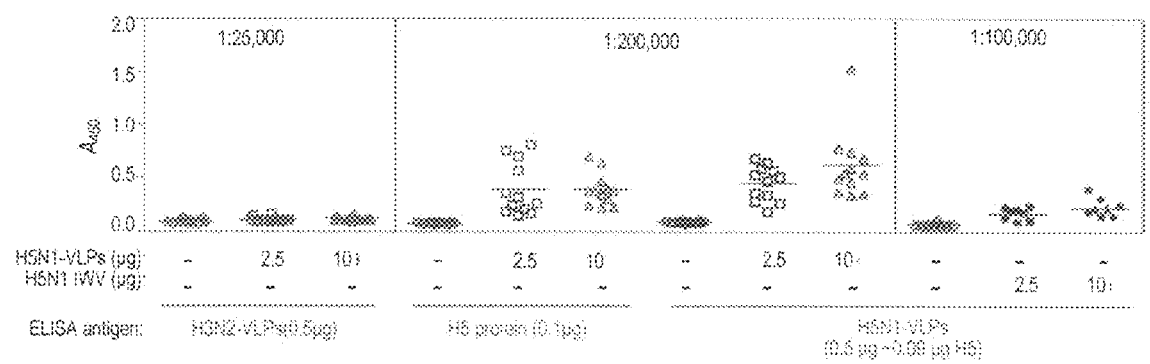
Figure 11C:
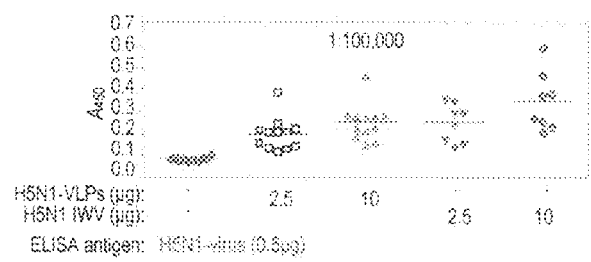
Figures 11D, 11E, 11F:
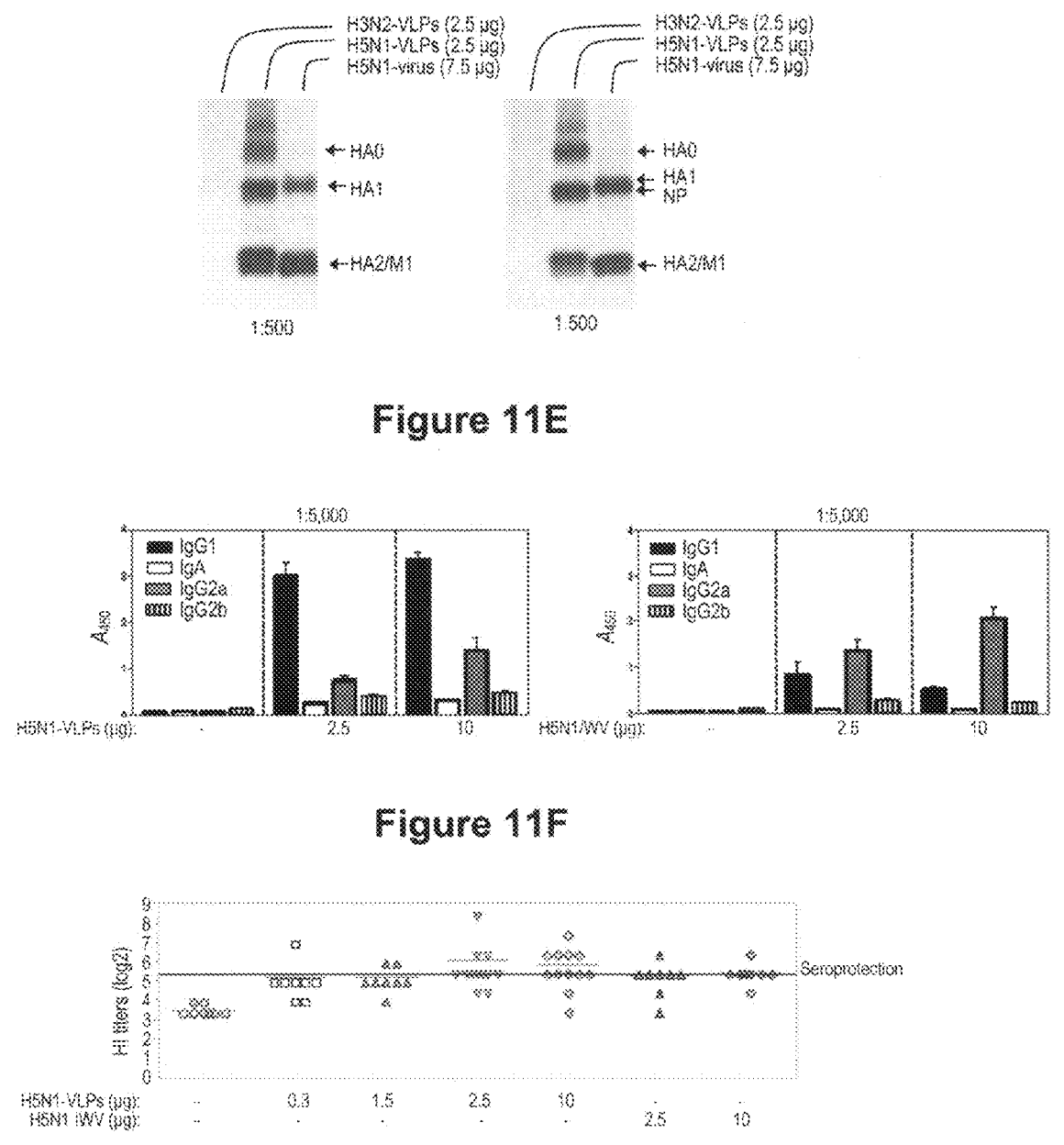

FIG. 11 illustrates humoral immune response of influenza VLPs made from Vero cells:

FIG. 11A shows the regimen of prime and boost vaccination followed by viral challenge: IM0, IM1, and IM2 represented the mouse serum collected at pre-immune, and 14 days after priming, and boosting, respectively;

FIG. 11B shows antigen-specific IgG antibodies from the serum of each mouse group taken at IM2 assayed against distinct antigens of H3N2-VLP, H5 protein (recombinant baculovirus expressed), and H5N1-VLP (same as the immunization antigen) by ELISA after vaccination of H5N1-VLP or inactivated whole virus (IWV): groups of mice (n=8-12) were either intramuscularly immunized with 2.5 μg and 10 μg dose of VLPs, or IWV, as marked; the dilution of used serum samples in the ELISA assays are labeled at the top; H3N2-VLPs contain all the host cell proteins integrated in the VLP antigen except with different subtype of HA and NA as negative control, whereas the baculovirus-produced H5 protein was positive control; the used amounts of coating antigens were equivalent as labeled;

FIG. 11C shows results of ELISA of serum IgG antibodies induced by H5N1-VLPs or IWV vaccines against H5N1 virus as ELISA antigen;

FIG. 11D shows results of Western blot analysis of mice serum IgG antibodies elicited by either H5N1-VLP (left panel) or IWV (right panel) vaccines: the used antigens and individual amounts are labeled at the top of panels;

FIG. 11E shows the specific IgG isotype and IgA elicited by VLPs and IWV vaccines assayed using H5N1-VLP as ELISA antigen; and FIG. 11F shows HI titer of each vaccinated mouse and plot of the mean values of the same group: HI titer of 40 was set as threshold of seroprotection.

FIGS. 12A-D show vaccine protection against lethal-dose challenge of H5N1 virus: at day 42, vaccinated mice were challenged intranasally with a lethal dose (100 $LD_{50}$) of recombinant H5N1 (NIBRG-14) virus and monitored daily for weight loss and mortality; the percentages of survival rate and changes of body weight and temperature were recorded: (A) survival for H5N1-VLP groups; (B) survival for IWV groups, mice that lost greater than 30% body weight were euthanized; (C) body weight and temperature for H5N1-VLP groups; for the groups receiving 0.3 μg and 1.5 μg antigen dose, only data of surviving mice are shown; and (D) body weight and temperature for IWV groups.

DETAILED DESCRIPTION OF THE INVENTION

Unless defined otherwise, all technical and scientific terms used herein have the same meaning as commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

To generate VLPs as a SARS vaccine, technical challenges include mammalian post-translational modifications and correct folding of viral proteins, their delicate organization into a lipid envelope, and sustainable yield for practical usage. The SARS-S protein is deduced as a huge glycoprotein containing 1255 aa residues with 23 putative N-linked glycosylation sites, and at least 12 N-glycans have been identified (Krokhin, O. et al., 2003, Mol Cell Proteomics 2: 346-56). In SARS-CoV infected cells and purified virion, protein M contains one high-mannose type N-glycan (Voss, D. et al., 2006, FEBS Lett 580: 968-73). Thus, mammalian expression and cell culture-based approaches are of interest to the inventors to attain massive production of SARS-VLPs.

In one aspect, the present invention provides a method for generating virus-like particles (VLPs) of a mammalian-hosted virus, such as SARS-CoV, the method comprising:
constructing a plasmid comprising a nucleotide sequence encoding a combination of at least two structural proteins of the virus;
transfecting Vero cells with the plasmid; and
expressing the viral structural proteins in the transfected cells to generate VLPs of the virus.

The method of the present invention is suitable for generating various mammalian-hosted viruses, including but not limited to arenaviruses, coronaviruses, hepadnaviruses, herpes viruses, orthomyxoviruses, paramyxoviruses, papovaviruses, parvoviruses, and retroviruses. In a preferred embodiment of the present invention, the mammalian-hosted virus is a coronavirus. More preferably, the mammalian-hosted virus is SARS-CoV.

The term "viral structural protein" or "structural protein of a virus" and equivalent terms as used herein refers to viral genome-encoded proteins that form the structure of a virus, including membrane glycoproteins and capsid proteins. The genome of a virus also encodes non-structural regulatory proteins involved in virus replication. For example, the structural proteins of a coronavirus comprise the M (membrane), E (envelope), S (spike) and N (nucleocapsid) proteins.

In an embodiment of the method used to generate SARS-VLPs according to the invention, the structural proteins to be expressed in transfected cells can be any combinations derived with the E, M, N and S proteins of SARS-CoV, such as, for example, M+E, M+E+S, M+S, N+M+E, N+M+E+S, and N+M+S. In a preferred embodiment, the combination of the structural proteins is M+E. Most preferably, the combination of the structural proteins is M+E+S.

The plasmid used in the present invention can be any plasmid or vector suitable for expressing heterologous proteins in mammalian cells. Many commercially available mammalian expression vectors can be readily used in the present invention, for example, the pcDNA™ series by Invitrogen Corporation (Carlsbad, Calif., USA).

To construct the recombinant plasmid used in the present invention, nucleotide sequences encoding a combination of the viral structural proteins can be grouped into one or more "expression cassettes" for controlled expression. As used herein, the term "expression cassette" refers to a nucleic acid construct, generated recombinantly or synthetically, with a series of specified nucleic acid elements which permit transcription of a nucleotide sequence of interest in a host cell. The expression cassette can be incorporated into a plasmid or chromosome. Typically, the expression cassette portion of an expression vector includes, among other sequences, a nucleotide sequence to be transcribed, a promoter, and a polyadenylation signal. In the present invention, the term "expression cassette" is used interchangeably with the term "transgene."

For optimal expression of the viral proteins of the present invention, the expression cassette may include an inducible system that allows high-level expression upon induction. In a preferred embodiment of the present invention, a tetracycline-inducible expression system is utilized for high-level expression of the viral proteins, wherein the induction is achieved by the addition of doxycycline into the culture medium. Examples of commercially available inducible expression systems include but not limited to the T-REx™ System and GeneSwitch™ System by Invitrogen Corporation, and the BD Tet-On™ and BD Tet-Off™ Gene Expression Systems by Clontech Laboratories, Inc. (Mountain View, Calif., USA).

According to an embodiment of the present invention, the cells used in the generation of VLPs are Vero cells. The Vero cell line, i.e. the cell line of ATCC No. CCL-81™, was initiated from the kidney of a normal adult African green monkey on Mar. 27, 1962, by Y. Yasumura and Y. Kawakita at the Chiba University in Chiba, Japan. The cell line was brought to the Laboratory of Tropical Virology, National Institute of Allergy and Infectious Diseases, National Institutes of Health in the 93rd passage from Chiba University by B. Simizu on Jun. 15, 1964. In addition to its use as a vaccine cell substrate, this cell line has been used extensively for virus replication studies and plaque assays. In the present invention, the term "Vero cell" includes not only cells from the original Vero cell line, but also those derived from Vero-derived cell lines such as Vero 76 (ATCC No. CRL-1587™) and Vero E6 (ATCC No. CRL-1586™).

Transfection can be performed by any known method and can result in either transient or stable transfection. Stable transfection is preferred to establish a cell line producing VLPs of interest. Methods for obtaining stable transfection are well known and include, for example, selection for spontaneously stable transfectants, transfection with immortalizing genes, and selection for genes providing resistance to antibiotics such as neomycin, puromycin, zeocin, hygromycin B, and blasticidin S.

As demonstrated in the following examples, SARS-VLPs generated by the method of the present invention can induce high titers of SARS-CoV-specific antibodies in mice. Therefore, the present invention also provides a method for generating antibodies against SARS-CoV, comprising immunizing a mammal or bird with SARS-VLPs generated according to the present invention, and harvesting antibodies against the VLPs from the blood of the mammal or bird.

According to the following examples, in addition to eliciting humoral immune responses, SARS-VLPs generated by the method of the present invention also stimulates systemic activation of T helper ($T_H$) cells. Therefore, the present invention also provides a method for preventing an infection of SARS-CoV in a subject, comprising immunizing the subject with SARS-VLPs generated according to the present invention. Preferably, the subject is a mammal, such as a dog, a cat, a rabbit, a rat, a mouse, a pig, a sheep; a goat, and a cow, and more preferably, a human.

Immunization can be performed traditionally. Suitable regimes for initial administration and booster doses are variable, but may include an initial administration followed by subsequent booster administrations. The quantity of SARS-VLPs to be administered depends on the subject to be immunized, including, for example, the capacity of the individual's immune system to synthesize antibodies, and if needed, to produce a cell-mediated immune response. Precise amounts of VLPs required to be administered depend on the judgment of the practitioner. However, suitable dosage ranges are readily determinable by one skilled in the art without undue experimentation in view of the present disclosure. The dosage may also depend on the route of administration and will vary according to the size of the host. Non-limiting exemplary dosages include, for instance, a preferred dosage of about 0.01 mg/kg to about 10 mg/kg body weight, and a more preferred dosage of about 0.1 mg/kg to about 1 mg/kg body weight.

In another aspect, the present invention provides a method for detecting an infection of SARS-CoV in a subject, comprising contacting a serum sample from the subject with SARS-VLPs generated according to the present invention, and determining the presence in the sample of an antibody/antigen complex, whereby the presence of the complex indicates a positive result.

Preferably, the method involves an immunoassay. In a particularly preferred embodiment of the present invention, the method involves an enzyme-linked immunosorbent assay (ELISA). In ELISA assays, the VLPs are immobilized onto a selected surface, for example, a surface capable of binding proteins, such as the wells of a polystyrene microtiter plate. After washing to remove incompletely adsorbed material, a nonspecific protein, such as a solution of bovine serum albumin (BSA) that is known to be antigenically neutral with regard to the test sample may be bound to the selected surface. This allows for blocking of nonspecific adsorption sites on the immobilizing surface and thus reduces the background caused by nonspecific binding of proteins in the antisera onto the surface.

The immobilizing surface is then contacted with a sample, such as a serum sample from a subject suspected of a SARS-CoV infection, in a manner conducive to immune complex (antigen/antibody) formation. This may include diluting the sample with diluents, such as solutions of BSA, bovine gamma globulin (BGG) and/or phosphate buffered saline (PBS)/Tween. The sample is then allowed to incubate for about 2 to about 4 hours, at suitable incubation temperatures, such as of the order of about 25° C. to about 37° C. Following incubation, the sample-contacted surface is washed to remove non-immunocomplexed material. The washing procedure may include washing with a solution, such as PBS/Tween™ or a borate buffer. Following formation of specific immunocomplexes between the test sample and the bound protein, and subsequent washing, the occurrence, and even the amount, of immunocomplex formation may be determined by subjecting the immunocomplex to a second antibody having specificity for the first antibody. If the test sample is of human origin, the second antibody is an antibody having specificity for human immunoglobulins and in general IgG. To provide for the detection, the second antibody may have an associated activity such as an enzymatic activity that will generate, for example, a color development upon incubating with an appropriate chromogenic substrate. Quantification may then be achieved by measuring the degree of color generation using, for example, a spectrophotometer.

The present invention also provides another method for detecting an infection of SARS-CoV in a subject, comprising contacting a tissue sample from the subject with antibodies against the SARS-VLPs generated according to the present invention, and determining the presence in the sample of an antibody/antigen complex, whereby the presence of the complex indicates a positive result.

Preferably, the method involves an immunoassay. In a particularly preferred embodiment of the present invention, the method involves indirect immunofluorescence staining. Indirect immunofluorescence staining involves intracellular staining of specific proteins with antibodies and tracking of the signals via respective fluorescence-labeled second antibodies. For example, target cells were first fixed, permeated, and washed, and the cells were blocked with 1% gelatin/PBST for 1 hour and then reacted with the first antibody (such as anti-S, M, E and GFP) in appropriate dilution with 1% gelatin/PBST at 4° C. for overnight. Subsequent to another three washes in PBST, the cells were incubated with the fluorescence-conjugated secondary antibody, washed and scanned under a confocal microscope.

In a further aspect, the present invention provides an immunogenic composition comprising SARS-VLPs generated according to the present invention. An immunogenic composition preferably generates immunological responses, such as antibody or T-cell responses, in a subject to whom it is administered.

SARS-VLPs generated according to the present invention can be purified after being harvested from a culture medium or cell suspension and before being used in an immunogenic composition. Any method can be used that is known to separate VLPs or viruses from surrounding proteins, lipids, nucleic acids, membranes, intact cells, and the like. Especially preferred are affinity chromatography methods; for example, an immobilized monoclonal antibody specific for SARS-VLPs can be used. Additional suitable methods are gel filtration chromatography, ion exchange chromatography, and density gradient sedimentation.

The immunogenicity of SARS-VLPs generated according to the present invention may be further improved when co-administered with adjuvants. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

For example, preferred adjuvants to enhance effectiveness of an immunogenic composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59™, containing 5% Squalene™, 0.5% Tween™ 80, and 0.5% Span™ 85 (optionally containing various amounts of MTP-PE (see below), although not required) formulated into submicron particles using a microfluidizer such as Model 1 10Y microfluidizer (Microfluidics, Newton, Mass., U.S.A.), (b) SAF™, containing 10% Squalane™, 0.4% Tween™ 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont., U.S.A.) containing 2% Squalene™, 0.2% Tween™ 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass., U.S.A.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (e.g., IL-1, IL-2, IL-4, IL-5, IL-6, IL-7, IL-12, etc.), interferons (e.g., gamma interferon), macrophage colony stimulating factor (M-CSF), tumor necrosis factor (TNF), etc; (6) detoxified mutants of a bacterial ADP-ribosylating toxin such as a cholera toxin (CT), a pertussis toxin (PT), or an E. coli heat-labile toxin (LT), particularly LT-K63, LT-R72, CT-Si09, PT-K9/G129; and (7) other substances that act as immunostimulating agents to enhance the effectiveness of the composition.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-s-n-glycero-3-hydroxyphosphoryloxy)-ethylamine (MTP-PE), etc.

Pharmaceutically acceptable salts can also be used in immunogenic compositions of the present invention. For example, mineral salts such as hydrochlorides, hydrobromides, phosphates, or sulfates, as well as salts of organic acids such as acetates, propionates, malonates, or benzoates.

Immunogenic compositions of the present invention generally contain pharmaceutically acceptable excipients, such as water, saline, glycerol, and ethanol, and may contain substances such as wetting agents, emulsifying agents, or pH buffering agents.

Immunogenic compositions of the present invention may be prepared as indictable, as liquid solutions, suspensions or emulsions, and administered parenterally, by injection subcutaneous, intradermal or intramuscularly injection. Alternatively, the immunogenic compositions of the present invention may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. Oral formulations can take the form of solutions, suspensions, tablets, pills, capsules, sustained release formulations or powders.

The immunogenic composition of the present invention may further comprise antigens from other pathogens to be a multivalent immunogenic composition.

In another aspect of the present invention, the mammalian-hosted virus is an orthomyxovirus, i.e., a family of RNA viruses that includes five genera: influenza virus A (such as H1N1, H2N2, H3N2, H5N1, H7N7, H1N2, H9N2, H7N2, H7N3, H10N7), influenza virus B, influenza virus C, isavirus and thogotovirus. Preferably, the mammalian-hosted virus is an influenza virus.

The structural proteins of an influenza virus, include, but are not limited to, hemagglutinin (HA), neuraminidase (NA), matrix (M1) and proton ion-channel protein (M2).

M1 is the most abundant protein in influenza particles. It forms a layer inside the viral envelope, which is derived from portions of the host cell membranes (phospholipids and proteins), but include some viral glycoproteins. M1 is able to direct viral assembly and budding. It is reported that the expression of M1 alone induces the release of VLPs from insect cells (see US20050186621A1 and references therein).

M2 is a proton-selective ion channel protein, integral in the viral envelope. It has an important role in the life cycle of the influenza virus, enables hydrogen ions to enter the viral particle (virion) from the endosome, thus lowering the pH inside of the virus and causing dissociation of the viral matrix protein M1 from the ribonucleoprotein RNP. This is a crucial step in uncoating of the virus and exposing its content to the cytoplasm of the host cell.

HA is an antigenic glycoprotein found on the surface of the influenza viruses. It is a type of hemagglutinin, i.e., a protein has the ability to cause red blood cells (erythrocytes) to clump together (agglutinate) in vitro. HA mediates binding of the influenza virus to target cells and entry of the viral genome into the target cell, e.g., by binding to the sialic acid-containing receptors on the surface of its target cells and causing the fusion of host endosomal membrane with the viral membrane. At least 16 different influenza HA subtypes have been discovered so far, H1 to H16.

NA is another antigenic glycoprotein found on the surface of the influenza viruses. It is involved in the release of progeny virus from infected cells, e.g., by catalyze the hydrolysis of terminal sialic acid residues from the newly formed virions and from the host cell receptors. Its activities also include assistance in the mobility of virus particles through the respiratory tract mucus and in the elution of virion progeny from the infected cell. At least 9 different influenza NA subtypes have been discovered so far, N1 to N9.

HA and NA are the sources of the major immunodominant epitopes for virus neutralization and protective immunity. They are considered the most important components for prophylactic influenza vaccines. Influenza A viruses are classified into subtypes based on antibody responses to HA and NA. Changes in HA and/or NA can significantly alter the host specificity of an influenza virus, e.g., making the virus infectious to a new host species or more infectious to an old host. When a new strain of influenza virus having a new subtype of HA and/or NA emerges, antibodies developed after vaccination against older influenza strains may not provide effective protection against the new strain. New influenza vaccines must be developed to take into account of the antigenic drift in flu viruses.

Currently, there are two types of seasonal influenza vaccines: the flu shot and the nasal-spray flu vaccine. The flu shot contains killed influenza virus that is given with a needle, usually in the arm. The flu shot is approved for use in people older than 6 months, including healthy people and people with chronic medical conditions. The nasal-spray flu vaccine contains live, weakened flu viruses that do not cause the flu (sometimes called LAIV for "live attenuated influenza vaccine" or FluMist®). LAIV (FluMist®) is approved for use in healthy people 2-49 years of age who are not pregnant.

Each seasonal influenza vaccine are formulated as a blend of three strains of influenza viruses, e.g., two strains of influenza A and one strain of influenza B. The viruses in the seasonal vaccine change each year based on international surveillance and scientists' estimations about which types and strains of viruses will circulate in a given year. About 2 weeks after vaccination, antibodies that provide protection against influenza virus infection develop in the body. However, the seasonal influenza vaccine may not be able to provide protection against all influenza in circulation among the human population for a given year. For example, the seasonal flu vaccine containing one influenza A (H3N2) virus, one regular seasonal A (H1N1) virus, and one influenza B virus does not provide protection against 2009 H1N1 flu, which has an unusual mix of swine, avian and human influenza genetic sequences. An influenza vaccine separate from the seasonal flu vaccine, such as that against 2009 H1N1, may be required to effectively prevent the outbreak or pandemic of influenza infection.

Yearly flu vaccination begins in September or as soon as vaccine is available and continues throughout the influenza season, into December, January, and beyond. This is because the timing and duration of influenza seasons vary. While influenza outbreaks can happen as early as October, most of the time influenza activity peaks in January or later.

According to embodiments of the present invention, a platform to generate influenza VLPs from Vero cells, such as Vero E6 cell, presents a practical new approach to safe and effective vaccine production. This platform does not have the drawbacks of the egg-based or the baculovirus culture-based methodology, and is an alternative to the conventional reverse genetics approaches used in influenza vaccine manufacture. The Vero cell system according to embodiments of the present invention produces influenza VLPs including not only HA and NA but also the matrix proteins M1 and M2, because both M1 and M2 have equally critical roles in influenza virus assembly and budding processes, suggesting their similar importance for mammalian VLP budding efficiency [31,32, 33,34,35,36]. The incorporation of M1 and M2 into influenza VLPs not only increased the VLP production yield from Vero cells, but also supplemented interior viral antigens, which can provide highly conserved T-cell and B-cell epitopes to fight homologous and heterologous viruses [37,38].

The flexibility of this approach has been demonstrated by exchanging the surface antigens of HA and NA to generate VLPs mimicking two subtypes of influenza (FIGS. 6 and 8). This can shorten the lead time for adjusting the match of vaccine specificity against the circulating strains of viruses. The preclinical-scale production of influenza VLPs from recombinant Vero cells has been achieved. This Vero cell VLP system alleviates safety restrictions and bottlenecks associated with dependence on live viruses. It also allows rapid and scaleable production, independent of a reliance on egg availability for manufacturing vaccines.

Generation of influenza VLPs from a mammalian cell has been previously reported by transient coexpression of HA and NA proteins in human 293T cells [30]. However, the present invention is the first report to reveal the proteome of VLPs made from a mammalian cell with sufficient quantities of HA and NA proteins as confirmed by SDS-PAGE analysis, including their further characterization by deglycosylation and hemagglutination assays. It is now discovered, for the first time, that VLPs expressed from Vero cells include multiple proteins from Vero cells, e.g. beta-actin, tubulin, etc., which are missing from VLPs made from other expression systems.

It is also discovered, for the first time, that VLPs expressed from Vero cells induce predominantly IgG1 antibodies, which is the same as that induced by the split or subunit vaccine and is indicative of Th2 type immune response. Vaccination of animals with VLPs expressed from Vero cells elicited HA-specific IgG1 antibodies and resulted in full protection against lethal infection of homologous virus. Whereas VLPs expressed from baculovirus induce IgG2a dominant antibody, which is the same as that induced by inactivated whole virus vaccine and is indicative of Th1 dominant immune response. The Th1 type response is prone to have adverse side effects.

It is further discovered, for the first time, that HA in Vero cell expressed VLPs contains both complex type and high-mannose type of glycans. Such glycosylated HA is not possible to make from the baculovirus system. By modifying the host insect cell, the baculovirus system can only choose one kind of glycosylation.

According to an embodiment of the present invention, an influenza virus-like particle (VLP) is prepared by a method comprising:

obtaining a founder Vero cell stably transfected with a sequence encoding an influenza M1 and a sequence encoding an influenza M2;

constructing at least one recombinant DNA molecule comprising a sequence encoding an influenza hemagglutinin (HA) and a sequence encoding an influenza neuraminidase (NA);

introducing the at least one recombinant DNA molecule into the founder Vero cell to obtain a co-expression Vero cell stably transfected with the sequences encoding the influenza M1 and the influenza M2, and transfected further with the sequences encoding the influenza HA and the influenza NA;

culturing the co-expression Vero cell under conditions to allow expressions of the influenza M1, the influenza M2, the influenza HA and the influenza NA, and assembly of the VLP comprising the influenza M1, the influenza M2, the influenza HA and the influenza NA; and isolating the VLP from the culture supernatant of the co-expression Vero cell.

The founder Vero cell can be obtained by stably transfecting a Vero cell with a DNA sequence encoding an influenza M1 and a DNA sequence encoding an influenza M2. The coding sequences of the influenza M1 and M2 can be derived from any influenza virus, such as H1N1, H5N1, H3N2, etc. The sequences encoding influenza M1 and M2 can be derived from the same influenza virus, or different influenza viruses. The sequences can be the same as those naturally occurring in the viruses. The sequences can also contain one or more modifications, preferably those do not alter the functions of the encoded influenza M1 and M2. For example, the sequences can be modified based on the degeneracy of genetic codon to optimize gene expression in Vero cells, without introducing any changes in the amino acid sequences of the encoded influenza M1 and M2.

The coding sequences of an influenza M1 and M2 are cloned into one or more expression vectors so that they are operably linked to expression control elements that allow expression of the influenza M1 and M2 in Vero cells. The expression control elements comprise a promoter for Vero cell expression, translation initiation codon, transcription and translation termination sequences. The expression control elements can also contain a regulatory sequence that allows regulation of gene expression, e.g., that for inducible expression of the influenza proteins.

The expression vector is introduced into a Vero cell using methods known in the art in view of the present disclosure. Sequences encoding the influenza M1 and M2, which include the coding sequences of the influenza M1 and M2 and the operably linked expression control elements, are integrated into the genome of the Vero cell. The resulting Vero cell, i.e., the founder Vero cell, is stably transfected with the sequences encoding the influenza M1 and M2. Such stably transfected cells are selected and verified using methods known in the art in view of the present disclosure. The sequences encoding the influenza M1 and M2 can be stably transfected into the Vero cell using a single expression vector, or two separate expression vectors.

In a particular embodiment of the present invention, the founder Vero cell is stably transfected with a sequence comprising SEQ ID NO:12, which encodes the influenza M1 and M2 of influenza A/Taiwan/083/2006. In SEQ ID NO:12, a CMV/TO promoter controls the transcription of the M1 and M2 coding sequences, which are linked with a internal ribosome entry site (IRES). A sequence (SEQ ID NO:13) that constitutively expresses a tet repressor is also stably transfected into the Vero cell to regulate the expression of all genes controlled by the CMV/TO promoter. In SEQ ID NO:13, a CMV promoter controls the transcription of the tet repressor coding sequence.

Expression vectors, cell lines, and methods similar to that describe above for the construction of recombinant Vero cells for SARS-CoV VLPs can be used for the construction of the founder Vero cells stably transfected with a sequence encoding an influenza M1 and a sequence encoding an influenza M2.

Live cultures of the founder Vero cells can be stored, e.g., by cryogenic storage at very low temperature, such as in liquid nitrogen. The cells can be conveniently retrieved and used for subsequent manipulation in a method according to embodiments of the present invention.

The coding sequences of HA and NA of one or more influenza viruses can be obtained using standard molecular biology techniques, such as RT-PCR, followed by DNA cloning and sequencing. The influenza viruses of interest can be potentially pandemic or seasonal influenza virus strains, i.e., the types and strains of flu viruses that will likely circulate among the human population for a given year based on international surveillance and scientists' estimations. The coding sequences of HA and NA can be derived from the same influenza virus, or different influenza viruses. The sequences can be the same as those naturally occurring in the viruses. The sequences can also contain one or more modifications, preferably those do not alter the antigenic specificity of the encoded influenza HA and NA. For example, the sequences can be modified based on the degeneracy of genetic codon to optimize gene expression in Vero cells, without introducing any changes in the amino acid sequences of the encoded influenza HA and NA. Or, selective residuals of the amino acid sequences can be mutated for specific purposes, such as enabling a protease cleavage site, disabling glycosylation sites or enabling fusion of designed epitopes.

The coding sequences of an influenza HA and NA are cloned into one or more expression vectors so that they are operably linked to expression control elements that allow expression of the influenza HA and NA in Vero cells. The expression control elements comprise a promoter for Vero cell expression, translation initiation codon, transcription and translation termination sequences. The expression control elements can also contain a regulatory sequence that allows regulation of gene expression, e.g., that for inducible expression of the influenza proteins.

The expression vector is introduced into the founder Vero cell using methods known in the art in view of the present disclosure. Sequences encoding the influenza HA and NA, which include the coding sequences of the influenza HA and NA and the operably linked expression control elements, can be integrated into the genome of the founder Vero cell, resulting in a co-expression Vero cell stably transfected with sequences encoding influenza proteins M1, M2, HA and NA. Sequences encoding the influenza HA and NA can also remain on the expression vector independent of the genome inside the cell, resulting in a co-expression Vero cell stably transfected with sequences encoding the influenza M1 and M2, but transiently transfected with the influenza HA and NA. Embodiments of the present invention include co-expression Vero cells that are stably or transiently transfected with sequences encoding the influenza HA and NA. The sequences encoding the influenza HA and NA can be transfected into the founder Vero cell using a single expression vector, or two separate expression vectors.

In particular embodiments of the present invention, the co-expression Vero cell is stably transfected with a sequence comprising SEQ ID NO:12, which encodes the influenza M1 and M2 of influenza A/Taiwan/083/2006, and further transfected, preferably stably transfected, with a sequence comprising SEQ ID NO:14, which encodes H3 and N2 of influenza A/Taiwan/083/2006. SEQ ID NO:14 also includes the 5'- and 3'-expression control elements for H3 and N2 expressions.

In another particular embodiments of the present invention, the co-expression Vero cell is stably transfected with a sequence comprising SEQ ID NO:12, which encodes the influenza M1 and M2 of influenza A/Taiwan/083/2006, and further transfected, preferably stably transfected, with a sequence comprising SEQ ID NO:15, which encodes H5 and N1 of influenza A/Hanoi/30408/2005(H5N1). SEQ ID NO:15 also includes the 5'- and 3'-expression control elements for H5 and N1 expressions.

One or more DNA sequences encoding additional proteins can be further introduced into the founder Vero cell for recombinant production of influenza VLPs further comprising the additional proteins.

In one embodiment of the present invention, one or more DNA sequences encoding an adjuvant, such as a flagellin of a pathogenic bacterium, can be introduced into the founder cell for recombinant production of VLPs containing the adjuvant.

In another embodiment of the present invention, sequences encoding HAs and NAs from two or more different influenza virus strains, e.g., two or more potentially pandemic or seasonal influenza virus strains, can be transfected into the founder Vero cell. The resulting co-expression Vero cell is stably transfected with sequences encoding the influenza M1 and M2, and transiently or stably transfected with sequences encoding HAs and NAs from the two or more different influenza virus strains. The co-expression Vero cell produces VLPs comprising a blend of HAs and NAs useful for prophylactic prevention of infection by the two or more different influenza virus strains.

Expression vectors and methods similar to that described above for the construction of recombinant Vero cells for SARS-CoV VLPs can be used for the construction of the co-expression Vero cells for influenza VLPs.

In an embodiment of the present invention, expressions of the sequences encoding the viral protein, e.g., influenza M1, M2, HA and NA, are under the control of one or more inducible gene expression systems, so that viral proteins are produced and assembled into influenza VLPs under inducible conditions. Any inducible gene expression system, such as those described above for inducible production of SARS-CoV VLPs, can be used for inducible production of influenza VLPs in view of the present disclosure. The viral proteins can be controlled by the same inducible gene expression system. Each of the viral proteins can also be controlled independently by different inducible gene expression systems.

Live cultures of the co-expression Vero cells can be stored, e.g., by cryogenic storage at very low temperature, such as in liquid nitrogen. The cells can be conveniently retrieved and used for subsequent production of influenza VLP.

Accordingly, an embodiment of the present invention relates to a method of preparing an influenza virus-like particle (VLP), the method comprising:

obtaining a co-expression Vero cell stably transfected with a sequence encoding an influenza M1 and a sequence encoding an influenza M2, and further transfected with a sequence encoding an influenza hemagglutinin (HA) and a sequence encoding an influenza neuraminidase (NA), wherein the expressions of the influenza M1, M2, HA and NA proteins in the co-expression Vero cell are controlled by one or more inducible expression systems; and culturing the co-expression Vero cell under conditions to allow expressions of the influenza M1, the influenza M2, the influenza HA and the influenza NA, and assembly of the VLP comprising the influenza M1, the influenza M2, the influenza HA and the influenza NA; and isolating the VLP from the culture supernatant of the co-expression Vero cell.

Embodiments of the present invention relate to a founder Vero cell that is a Vero cell stably transfected with a sequence encoding an influenza M1 and a sequence encoding an influenza M2, wherein the expressions of the influenza M1 and M2 proteins in the founder Vero cell are controlled by an inducible expression system.

Methods of obtaining a founder Vero cell are also encompassed by embodiments of the present invention. The method comprises:

introducing into a Vero cell a sequence encoding an influenza M1 and a sequence encoding an influenza M2; and obtaining the founder Vero cell stably transfected with the sequence encoding the influenza M1 and the sequence encoding the influenza M2, wherein the expressions of the influenza M1 and M2 proteins in the founder Vero cell are controlled by an inducible expression system.

The sequence encoding the influenza M1 and the sequence encoding the influenza M2 can be introduced into the Vero cell on a single nucleic acid molecule or on two separate nucleic acid molecules.

In an embodiment of the present invention, the founder Vero cell is a Vero E6 cell stably transfected with a sequence encoding an influenza M1 and a sequence encoding an influenza M2, wherein the expressions of the influenza M1 and M2 proteins in the founder Vero E6 cell are controlled by an inducible expression system.

The founder Vero cell can be used as a host cell for construction of recombinant Vero cells comprising one or more transfected sequences encoding one or more influenza proteins that are different from the influenza M1 and M2.

Embodiments of the present invention relate to a co-expression Vero cell that is a Vero cell stably transfected with a sequence encoding an influenza M1 and a sequence encoding an influenza M2, and further transfected with a sequence encoding an influenza HA and a sequence encoding an influenza NA, wherein the expressions of the influenza M1, M2, HA and NA proteins in the co-expression Vero cell are controlled by one or more inducible expression systems. In one embodiment, the co-expression Vero cell is recombinantly made from Vero E6 cell.

Method of obtaining a co-expression Vero cell are also encompassed by embodiments of the present invention. The method comprises:

obtaining a founder Vero cell stably transfected with a sequence encoding the influenza M1 and a sequence encoding the influenza M2;

introducing into the founder Vero cell a sequence encoding an influenza HA and a sequence encoding an influenza NA; and obtaining a co-expression Vero cell stably transfected with the sequence encoding the influenza M1 and the sequence encoding the influenza M2, and further transfected with the sequence encoding the influenza HA and the sequence encoding the influenza NA, wherein the expressions of the influenza M1, M2, HA and NA proteins in the co-expression Vero cell are controlled by one or more inducible expression systems.

The sequence encoding the influenza HA and the sequence encoding the influenza NA can be introduced into the Vero cell on a single nucleic acid molecule or on two separate nucleic acid molecules. The co-expression cell can be stably or transiently transfected with the sequence encoding the influenza HA and the sequence encoding the influenza NA.

The expression of each of the influenza M1, M2, HA and NA proteins can be independently controlled by the same or different inducible expression system. In one embodiment, the expression of the influenza M1, M2, HA and NA proteins are controlled by the same inducible expression system.

Influenza proteins, e.g., M1, M2, HA and NA, are expressed in the co-expression Vero cell under suitable conditions, e.g., when the cell is grown in a medium containing inducer for the inducible expression system. These viral proteins, together with some cellular proteins from Vero cell, self-assemble into noninfectious VLPs with the antigenic HA and NA presented on the surface of the VLPs. The VLPs are secreted into the culture medium of the co-expression Vero cell. They are subsequently separated from the cells and isolated using methods that preserve the integrity of the VLPs, such as by density gradient centrifugation, and the like.

Methods similar to that described above for the production and isolation of SARS-CoV VLPs can be used for the preparation of influenza VLPs according to embodiments of the present invention.

It is now discovered for the first time that the cellular constituents specifically present in authentic influenza virus particles were also incorporated into the influenza VLP produced from Vero cells. This indicates that the particular interactions between host proteins and viral proteins involved in the biosynthesis of VLPs reflected similar processes as that during virus assembly and budding of the authentic virus particles (Table 1 and FIG. 9). In addition, several cellular proteins are found to be associated with the influenza VLPs according to embodiments of the present invention, but not with the virus particles, suggesting that these proteins may play a role in Vero cell production of influenza VLPs, but not influenza virus particles.

Accordingly, another embodiment of the present invention relates to an influenza virus-like particle (VLP), comprising: an influenza M1, an influenza M2, an influenza hemagglutinin (HA) and an influenza neuraminidase (NA), and at least one cellular protein of a Vero cell, wherein the influenza proteins are recombinantly expressed from the Vero cell.

In a particular embodiment of the present invention, the Vero cell is Vero E6 cell.

The influenza M1, M2, HA and NA in the influenza VLP can be derived from the same or different influenza virus strains. In one embodiment of the present invention, the influenza M1 and M2 are derived from the same influenza virus, and the HA and NA are derived from one or more different influenza virus trains, such as one or more potentially pandemic or seasonal influenza virus strains. In an embodiment of the present invention, the influenza HA and the influenza NA are derived from the same potentially pandemic or seasonal influenza virus strain.

In another embodiment of the present invention, the influenza VLP comprise two or more HAs and two or more NAs derived from two or more different influenza virus strains, e.g., two or more potentially pandemic or seasonal influenza virus strains.

In particular embodiments of the present invention, the influenza VLP comprises the M1 (SEQ ID NO:6) and the M2 (SEQ ID NO:7) of influenza A/Taiwan/083/2006, and the H3 (SEQ ID NO:8) and N2 (SEQ ID NO:9) of influenza A/Taiwan/083/2006.

In another particular embodiments of the present invention, the influenza VLP comprises the M1 (SEQ ID NO:6) and the M2 (SEQ ID NO:7) of influenza A/Taiwan/083/2006, and H5 (SEQ ID NO:10) and N1 (SEQ ID NO:11) of influenza A/Hanoi/30408/2005(H5N1).

In one embodiment of the present invention, the cellular proteins in the influenza VLP according to an embodiment of the present invention include those that are also present in authentic influenza viruses, such as those listed in Table 1, e.g., cytoskeleton protein, extra cellular matrix (ECM) proteins, heat shock proteins, annexins, tetraspanins, and glycolytic enzymes.

In another embodiment of the present invention, the influenza VLP comprises a cellular protein that is not present in influenza virus particles, such as those listed in Table 2, e.g., one or more selected from the group consisting of clathrin heavy chain 1, spectrin beta, plexin B2, CD109 homolog, prostaglandin F2 receptor negative regulator, Na+/K+-ATPase alpha 1, tumor rejection antigen (gp96) 1 and flotillin I.

The glycosylation profiles of HA and NA spike in influenza VLPs according to embodiments of the present invention were examined by N-deglycosylation (FIG. 10). In the case of H3N2-VLPs, the glycosylation profiles of HA were highly similar to that of influenza virus replicating in the Vero cells [25]. When examined by transmission electron microscopy (TEM), the influenza VLPs according to embodiments of the present invention were found to closely resemble influenza virus in size, particle morphology, and fine structure of the surface spikes (FIGS. 6 and 7). It was found that influenza VLPs according to embodiments of the present invention stimulated antibody response in mice administered with the VLPs. It was also demonstrated that vaccination of the influenza VLPs according to embodiments of the present invention provided total protection to mouse against avian influenza infection. All these results indicate that influenza VLPs provide a safe and effective means against influenza infection.

An embodiment of the present invention relates to an immunogenic composition comprising an immunogenic effective amount of the influenza VLP according to an embodiment of the present invention and a pharmaceutically acceptable excipient. The immunogenic composition can further comprise an adjuvant. Any of the pharmaceutically acceptable excipient or adjuvant, such as those described above for the immunogenic composition comprising SARS-CoV VLPs, can be used in the immunogenic composition comprising the influenza VLP.

In one embodiment of the present invention, the immunogenic composition according to an embodiment of the present invention is administered to a subject to induce immunity against an influenza virus in the subject. The immunogenic composition comprises an influenza VLP comprising the HA and the NA derived from the target influenza virus. The induction of the immunity in the subject results in the prevention, amelioration, or reduction of at least one symptom related to influenza virus infection in the subject. The "immunogenic effective amount of the influenza VLP" generally refers to the amount of the influenza VLP sufficient to induce immunity to prevent, ameliorate, or reduce at least one symptom related to infection of influenza virus.

In another embodiment of the present invention, protection against an influenza virus in a subject is provided by vaccinating the subject with a vaccine comprising an influenza VLP according to an embodiment of the present invention, wherein the influenza VLP comprises the HA and the NA derived from the influenza virus.

In an embodiment of the present invention, a blend of influenza VLPs comprising HAs and NAs from more than one influenza virus strains is administered to a subject to induce immunity against the more than one influenza virus strains in the subject.

In another embodiment of the present invention, an influenza VLP according to an embodiment of the present invention is used in a method of diagnosing infection by an influenza virus in a subject. The method comprises:

obtaining a biological sample from the subject;

contacting the biological sample with the influenza VLP, wherein the influenza VLP comprises the HA and the NA derived from the influenza virus; and measuring in the biological sample the amount of an antibody that forms an antibody-antigen complex with the influenza VLP, whereby a higher than a threshold amount of the antibody indicates that the subject has ever been infected by the influenza virus or vaccinated by a similar strain of virus.

The biological sample can be, for example, a serum sample or a tissue fluid. The amount of the antibody that forms an antibody-antigen complex with the influenza VLP can be measured using any methods, such as ELISA, in view of the present disclosure. The threshold amount of the antibody can be determined from a positive control, e.g., a biological sample taken from a subject known to be infected by a threshold titer of the influenza virus.

Another embodiment of the present invention relates to an antibody against the influenza VLP according to embodiments of the present invention.

The antibody can be prepared using methods known in the art in view of the present disclosure. For example, the antibody can be prepared by administering the VLP to a vertebrate; and harvesting the antibody against the VLP from the blood of the vertebrate. The antibody can be polyclonal or monoclonal.

The antibody can be used for various purposes, such as for the treatment or diagnosis of infection by an influenza virus.

In one embodiment of the present invention, a method of treating infection by an influenza virus in a subject comprises administering to the subject an antibody against an influenza VLP. The influenza VLP comprises the HA and the NA derived from the target influenza virus.

The antibody can be administered to the subject together with a pharmaceutically acceptable excipients as those described above. The antibody recognizes and binds to antigenic sites on the HA and NA on the surface of the influenza virus, thus mediates an immune response against the influenza virus in the subject. The HA-specific antibody plays an important role for neutralization of the influenza virus, and the NA-specific antibody lessens the release of virus from infected cells. The antibodies can also block the influenza virus from entering cells in the subject or block replication of the influenza virus. Early intervention with an antibody therapy or passive immunization with immune plasma involving antibodies against influenza VLP can help to control the outbreak of acute influenza virus infection, particularly in subjects with weak, suppressed, or compromised immune systems.

In another embodiment, the antibody can be used in a method for detecting infection by an influenza virus in a subject. The method comprises:

obtaining a biological sample from the subject;

contacting the biological sample with the antibody of claim 17; and detecting in the biological sample an antigen that forms an antibody-antigen complex with the antibody, wherein the presence of the antigen in the biological sample indicates that the subject is infected by the influenza virus.

The biological sample can be, for example, serum, throat swap, tear, or tissue specimen, etc., from the subject.

Embodiments of the present invention include compositions and methods related to the influenza VLPs produced by Vero cells similar to those described above for SARS-CoV VLPs.

The present invention is further illustrated by the following examples, which are provided for the purpose of demonstration rather than limitation.

Example 1

Expression and Assembly of SARS-VLPs

Cell Lines and Plasmids

Vero E6 cells were obtained from American Type Culture Collection (ATCC No. CRL-1586™) and routinely cultured in MEM medium supplemented with 10% fetal bovine serum. Vero E6-based tetracycline-inducible founder cells, Vero/TR, were derived by a stable transfection with the pcDNA6/TR plasmid (Invitrogen). Inducible M-GFP and E expression cassettes were constructed by PCR linking consecutively a β-globin/IgG chimeric intron (from pCI vector, Promega), M-GFP coding sequence, an internal ribosome entry site (IRES) from the encephalomyocarditis virus (ECMV), and an E coding sequence, and the construct was then inserted into the backbone of the pcDNA4/TO plasmid (Invitrogen). Inducible S expression cassette was constructed by inserting a cDNA of the S protein of TW1 strain into the pcDNA5/TO plasmid (Invitrogen). Subsequently, the entire S expression cassette was inserted into the expression plasmid for M-GFP and E to generate the pcDNA4/TO-S-MG-E vector. The sequence of the entire plasmid was verified by DNA sequencing.

Plasmid Construction

As shown in FIG. 1A, transgenes encoding the three SARS-CoV envelope proteins, S, M-GFP (i.e., the M protein fused with a green fluorescent protein (GFP) for tracking the VLPs) and E, were constructed in the same plasmid (pcDNA4/TO-S-MG-E). In one plasmid, the vector harbors two expression cassettes. The CMV/TO-MG-E cassette (SEQ ID NO: 1) transcribes an RNA transcript that holds two open-reading frames encoding the M-GFP and E proteins, which are connected by an internal ribosome entry sequence (IRES), and the CMV/TO-S cassette (SEQ ID NO: 2) expresses only the S protein. Both transcription units are regulated by a tetracycline-inducible promoter.

VLP Expression

Stable transfection of the pcDNA4/TO-S-MG-E vector into a planned Vero E6-derived founder cell line was conducted to obtain SARS-VLP expression. The founder cell has been previously stably transfected with a tetracycline repressor gene (pcDNA6/TR); therefore, the recombinant SARS-CoV genes will not express until induction. According to the fluorescence intensity of GFP, two clones were selected for prolific production of SARS-VLP, namely Vero/S-MG-E-55 and Vero/S-MG-E-68. Expression of the viral genes was induced by addition of doxycycline (1 µg/ml) to the cell culture, as verified by RT-PCR for inducible expression of RNA encoding the S, M and E (data not shown). Expression level of VLP in Vero/S-MG-E-55 is higher than Vero/S-MG-E68, therefore is primarily used.

For confocal-microscopy analysis, test cells were grown on 12 mm coverslips and treated with doxycycline (1 µg/ml)

for 1 day. Cells were fixed with 4% paraformaldehyde on ice for 20 mins, permeabilized with 0.2% (v/v) Triton X™-100/PBS, and then washed with PBS three times. After blocking in 1% (v/v) fish gelatin/PBST (PBS with 0.1% Tween™-20) for 1 hr, samples were incubated with a specific antibody at 4° C. for 18 hrs, followed by 3 washes with PBST, and then probed with the respective fluorescence-conjugated secondary antibody for 1 hr at room temperature. Finally, samples were washed with PBST three times and mounted in mounting medium (Vector). The samples were scanned for GFP and antibody-stained signals, thereafter analyzed for co-localization according to the manufacture's software (Zeiss LSM 510 META).

Upon induction, GFP dots appear evident inside the producer cells within one day and accruing for longer than five days as shown in microscopic studies (FIG. 1B). The GFP dots of various sizes in the cytoplasm from the peri-nuclear region toward plasma membrane, showing indicative pattern all along the secretory pathway of mammalian cells from endoplasmic reticulum (ER) to the plasma membrane. This intracellular distribution corresponds with the CoV assembly of SARS and others, which is located at ER-Golgi-intermediate-compartment.

Intracellular expression of each VLP component protein (S, M, E and GFP) and their assembly were next inspected by immuno-fluorescence staining and overlaid with the fluorescence tracks of GFP, as exemplified by VLP producer cells induced for one day (FIG. 1B). Staining with antibodies against either M protein or GFP results in signals which completely overlap with GFP tracks and thus indicates that GFP fusion faithfully labels the M protein (FIG. 1B). In additional to peri-nuclear staining (Golgi complex), the S protein is stained intensely as reticular ER pattern in addition to the profiles of Golgi and secretory vesicles (FIG. 1B). However, the co-localization of S protein with M-GFP principally limits to Golgi and secretory vesicles. More S protein accumulates in ER, suggesting its longer duration for de novo synthesis and glycosylation in ER. While most secretory M-GFP dots co-localize with the staining of E protein, peri-nuclear M-GFP shows two ways, positively and negatively co-localized with E protein. These data collectively suggest that E protein as soon as it is translated initiates VLP assembly with M-GFP and S protein nearby the Golgi and resulting in punctual co-staining of M-GFP, E, and S proteins as secretory vesicles (FIG. 1B). As negative controls, the same immuno-staining with the S, M or E Ab in parental Vero E6 cells detected no signals; neither was seen for fluorescence tracks of GFP (data not shown). In agreement with previous studies on CoV budding, VLP assembly for SARS-CoV and others in mammalian cells, our data indicated the peri-nuclear assembly of SARS-M, E and S and their co-localization in a secretory vesicle profile. Assembly of the three proteins into SARS-CoV-like particles is further demonstrated by their co-sedimentation in a sucrose gradient and forming spiky spherical particles (FIG. 2D).

Example 2

Purification and Characterization of SARS VLPs

Purification of VLP was initially performed by concentrating conditioned culture medium of the induced cells on a 45% sucrose cushion by ultracentrifugation at 200,000×g at 4° C. for 2 hrs. The interface was collected and further separated on a step-wise gradient between 25% and 35% sucrose at 200,000×g at 4° C., for 48 hrs. Sedimentation fractions were taken from the bottom of the tube every 0.5 ml volume. Each fraction was analyzed for protein concentration by Coomassie (Bradford) Protein Assay Kit (Pierce) and GFP fluorescence measured by VICTOR$^{2}$™ fluorometer (PerkinElmer).

For western blot analysis, polyclonal antibodies against E and M proteins were separately raised in rabbits using *E. coli* expressed M (a.a. 53-221 of SEQ ID NO: 3) and E (a.a. 1-76 of SEQ ID NO: 4) proteins as antigens by intraspleenic injection. Anti-S polyclonal antibodies were raised in ducks using *E. coli* expressed S (a.a. 679-888 of SEQ ID NO: 5) as antigens, and IgY antibodies were purified from egg white (Wu, H. S. et al., 2004, *J Biomed Sci* 11: 117-126).

As shown in FIG. 2A, distribution of both proteins and GFP exhibited a coherent major peak concentrated in 25% sucrose layer (fractions 9 to 15). Unexpectedly, we also find a minor protein peak concentrated in 35% sucrose layer, which is absent in the Vero/S-MG-E-68 clone (fractions 2 to 6). Protein analysis by SDS-PAGE and Coomassie blue staining reveal that the two distinct peaks are obviously of different protein compositions (FIG. 2B). Each VLP constituent protein of expected size as marked in FIG. 2B is confirmed by western blot analysis using specific antibodies against S, M, E and GFP proteins (FIG. 2C). The SARS-VLP contains multiple forms of S protein, predominantly of mature form with apparent $M_r$ 180 kDa (○), and less with 170 kDa (★), and 140 kDa (+) (FIG. 2B). According to previous studies on individual expression of S and M proteins in mammalian cells, the 180 kDa (○) band represents a complex-type glycosylated form (EndoH-resistant yet PNGaseF-sensitive); the 170 kDa (★) band represents a high-mannose-type glycosylated form (EndoH-sensitive); and the 140 kDa (+) band represents a non-glycosylated form. The purified SARS-CoV contains two forms of M. The more abundant form with apparent $M_r$ 22 kDa is not glycosylated, and the less abundant 27 kDa form contains an EndoH-sensitive, high-mannose-type N-glycan linked to the Asn-4 residue (Voss, D. et al., 2006, supra). In agreement, the M-GFP in SARS-VLP is mainly of 65 kDa (#), and less of 70 kDa (*) (FIG. 2B). Since GFP fusion contributes $M_r$ ~27 kDa, both forms of M-GFP in SARS-VLP show an additional 16 kDa increase in apparent $M_r$ due to unknown reasons. The E protein associates with M protein in sucrose gradient sedimentation and perhaps lacks glycosylation as per its 9 kDa size.

The SARS-VLP resides in the expected major peak; whereas the unexpected minor peak comprises primarily S protein of the 170 kDa form, less for M-GFP of the 65 kDa form, but no E protein, and not observable by electron microscopy; therefore, it is not further characterized here (data not shown). The SARS-VLP of interest to the inventors (i.e., fractions 9 to 15 in FIGS. 2A-2C) contains primarily M-GFP, with less S protein and the least E protein, which is a ratio similar to CoV of SARS and others. The S protein of the secreted SARS-VLP is the predominant 180 kDa form containing complex-type N-glycans whose maturation was suggested to occur before S protein trimerizes. All forms of S protein contained in the secreted SARS-VLP were found not cleaved as estimated by their mobility in SDS-PAGE.

Morphology of the SARS-VLP was further examined by transmission electron microscopy (EM). For EM, aliquots of 10 μl of purified SARS-VLPs were loaded onto a carbon-coated grid, and let stand still for 3 mins. Grids were then stained with 2% uranyl acetate for 2 mins, and examined directly under an electron microscope. As can be seen in FIG. 2D, the negatively-stained VLP appeared as spherical particles with a spiky surface resembling SARS-CoV particle and a diameter ranging between 50 nm and 70 nm. The diameter of Vero E6 cell-secreted empty VLP is smaller than the extra-cellular whole SARS-CoV whose diameter is between 60 nm and 100 nm.

Noteworthy, the protein yield of the SARS-VLP described above is fascinatingly high, which makes the system very attractive for all relevant applications. The result demonstrated in FIG. 2 represents a routine purification of VLP from a pool of 750 ml culture medium collected on day 3 and day 5 after induction. Summation of fractions 9 to 15 (3 ml in each fraction) yields 250 mg protein of purified VLP in total (FIG. 2A). The inventors' routine yield of mammalian cell-based SARS-VLP from Vero/S-MG-E-55 cells is 449.7±69.3 (N=12) mg/L of culture medium (using $1.2 \times 10^8$ producer cells), and is over 1.000-fold higher than the reported level of insect cell-based SARS-VLP ($200 \mu g/L \times 10^9$ host cells, estimated to be 0.5 to 1 L of cell culture) (Mortola E. and Roy, P., 2004, supra). The inventors believe the unprecedentedly high expression level of SARS-VLP in this study may result from the best match of Vero E6 as host cells to express the SARS viral proteins and insertion of the transgenes into a chromatin position which is highly active in gene transcription, because the inventors also isolated many other transgenic Vero E6 clones whose intracellular expression of GFP dots were at apparently lower levels. However, it may also involve with the much stronger expression from the inducible CMV promoter used in our cell line. Production of SARS-VLPs in Vero E6 cells by stable transfection gives the best high yields to the inventors' understanding and the production process is ready to be adapted for large scale manufacture, offering an attractive approach for development of an effective and economical vaccine.

Example 3

Vaccination Experiments with SARS-VLPs

With the high-yield SARS-VLP available from mammalian expression as described above, the subsequent important question is its immunogenicity and SARS-CoV-neutralizing antibody response. To address this issue, the inventors designed a series of vaccination experiments in mice and examined the systemic immune responses (FIG. 3A). Groups of four female C57BL/6 mice, 6-8 weeks of age, were s.c. injected with 20 µg of SARS-VLP in 100 µl of PBS without additional adjuvant, and boosted with different dosages (0, 5 µg, 20 µg) after 2 weeks. Mock immunization mice were injected with 100 µl of PBS as controls.

Immunization with SARS-VLP Elicits an Antigen-Specific IgG1 Response in Mice.

Two weeks after booster immunization, serum titers of antigen-specific IgG were measured by ELISA using native SARS-VLPs as the absorbent antigen. For ELISA, serum was collected by tail vein bleeding, allowing clotting at 4° C. overnight and cleared up by centrifugation. ELISA plates (Nunc) was coated with 1 µg native VLP at 4° C. overnight and blocked with 5% dry milk in PBS. ELISA plates were then incubated with serum samples of indicated dilution at 37° C. for 1 hr, traced with HRP-conjugated secondary antibodies, and developed color with TMB substrate (PIERCE). Washes with PBST for 5 times were applied between each step of ELISA. Finally, the ELISA was read out with absorbance of 450 nm wavelength ($A_{450}$) by a microplate reader (Power Wave XS, Bio-Teck). VLP-specific IgG titer ($A_{450}$) was calculated by subtracting the background readout of mock samples.

As shown in FIG. 3B, a single dose of 20 µg VLP positively induced antibody response up to 50-fold. The specific antibody titers were dose-dependently increased by a booster immunization for over 6250-fold (FIG. 3B). Similar ELISA for various IgG subtypes detected that the antibody response mainly restricted in IgG1 subtype which generally acts on neutralization (FIG. 3B). In contrast, IgG2a subtype of VLP-specific antibody titer was very low in these experiments (FIG. 3B). Together, the response of antibody subtype indicates an induction of $T_H2$-type effector functions against the epitopes on the SARS-VLP surface. Most prominently, the IgG antibody stimulated by the SARS-VLP effectively cross-reacted with genuine SARS-CoV virion inactivated by the gamma-radiation and heat, as demonstrated by ELISA using a commercial kit advised in the World Health Organization website (FIG. 3C). The antigen-specific antibody in mice serum retains high titers for longer than 4 weeks following the booster immunization, indicating a long persistence of antibody response caused by SARS-VLP immunization (FIG. 3D). The ELISA results in FIG. 3B-3C are particularly meaningful to SARS-CoV neutralization because they discern the antibody that binds surface of VLP and whole virus. These results endorse the resemblance in surface between the VLP and intact SARS-CoV and indicate a potential neutralizing antibody response induced by SARS-VLP vaccine in mice.

SARS-VLP-Induced Serum IgG Antibodies Recognize S and M Proteins.

The antigen determinants with which VLP protein the mouse anti-bodies would react were examined by western blot assay loaded with three different amounts of SARS-VLP. As shown in FIG. 3E, the VLP-specific antibody detects the most intensely against M-GFP, followed by S protein, and minimally to E protein. The VLP-specific antibody efficiently reacted with all forms of S and M proteins. The observations specify that M and S proteins in the context of SARS-VLP are much more immunogenic than E protein, which also agrees with the antibody specificity found in SARS patients.

Immunization with SARS-VLP Induces Antigen-Specific T Helper ($T_H$) Responses in Mice.

The type of $T_H$ response upon SARS-VLP vaccination was investigated by IFN-γ and IL-4 ELISPOT (enzyme-linked immunospot) assays for commitment to secrete $T_H1$ and $T_H2$ cytokines by splenocytes. For ELISPOT assays, PVDF-bottom plates (Millipore) were coated with 0.1 ml INF-γ and IL-4 capture antibodies (1:60; R&D systems) at 4° C. overnight. After washing with PBS twice, the plates were and then blocked with 1% BSA in PBS at room temperature for 4 hrs. Splenocytes were isolated from tested mice 14 days after booster administration, and allowing erythrocyte lysis. Splenocytes of single cell were suspended in RPMI containing 10% heat-inactive FBS, 50 µM β-mercapto-ethanol, and $3 \times 10^5$ cells/well were grown in INF-γ or IL-4 ELISPOT plates with 1 µg VLP for 40 hrs. Washes with PBST for 5 times were applied between each step of ELISPOT. The plates were incubated with 0.1 ml biotinylated INF-γ or IL-4 detection antibodies of 1/60 dilution (R&D systems) at 4° C. overnight, incubated with streptavidin-alkaline phosphatase of 1/60 dilution (R&D systems) at room temperature for 1.5 hrs, washed, and rinsed twice with water. The color of ELISPOT was developed in darkness for 30 mins with BCIP/NBT solution (R&D systems). Development was stopped by washing with water and air-dried. The signals were counted by ImmunoSpot analyzer and analyzed by ImmunoSpot software (CTL).

When the primary culture of splenocytes isolated from SARS-VLP-immunized mice re-exposed to SARS-VLP ex vivo, both INF-γ- and IL-4-producing populations rise along with the booster dose of SARS-VLP, indicating development of VLP-recognizing $T_H1$ cells and $T_H2$ cells in spleen provoked by SARS-VLP vaccination dose-dependently in vivo (FIGS. 4A, 4B). However, a $T_H2$-biased Ab response as indicated by induction of IgG1-dominant antibodies in serum further indicates the effector function of $T_H1$ cells in vaccinated mice was to activate CTL. Further, both $T_H1$ and CTL can secrete INF-γ when DC presents them against the VLP-antigens (FIGS. 3B, 3C). Together, these data demonstrate that SARS-VLP per se is a potent vaccine that raised humoral and cellular immune responses.

Example 4

Expression and Purification of Influenza VLPs from Vero Cells

Establishment of Vero Cell System Producing Influenza VLPs

Vero cells were obtained from the Bioresource Collection and Research Center, (Hsinchu, Taiwan) and maintained in minimal essential medium (HyClone, South Logan, Utah) supplemented with 10% fetal bovine serum (Gibco, San Diego, Calif.) in a humidified incubator at 37° C. with 5% $CO_2$.

The cDNAs of M1 and M2 derived from the sequences of influenza A/Taiwan/083/2006 virus were cloned into the backbone modified from pcDNA6/TR (Invitrogen, Carlsbad, Calif.) linked by IRES separately into a single eukaryotic expression vector to give the plasmid of pCI6/TO-M1-M2 (FIG. 5A). The amino acid sequences of the encoded M1 and M2 are SEQ ID NO:6 and SEQ ID NO:7, respectively. The cDNAs of HA and NA were synthesized sequences based on the distinct virus strains of A/Taiwan/083/2006 and A/Hanoi/30408/2005(H5N1) (a kind gift from Dr. Po-Huang Liang at Institute of Biological Chemistry, Academia Sinica) optimized for mammalian codon usage and further cloned into expression vectors as illustrated for pCI4/TO-HA-NA (FIG. 5A). The amino acid sequences of the encoded HA and NA based on A/Taiwan/083/2006 are SEQ ID NO:8 and SEQ ID NO:9, respectively. The amino acid sequences of the encoded HA and NA based on A/Hanoi/30408/2005(H5N1) are SEQ ID NO:10 and SEQ ID NO:11, respectively.

For the H3N2- and H5N1-VLPs producing Vero cells, the plasmid pCI6/TO-M1-M2 was stably transfected into Vero cells to derive a founder Vero cell line, which was further transfected with HA-NA expression vectors to obtain the quadruple co-expression Vero cell line with HA, NA, M1, and M2 proteins.

To confirm the gene expression of N2 in the H3N2-VLP producer cell line, total RNAs were extracted separately from cells with and without doxycycline (Dox) induction and RT-PCR assays performed using a primer pair corresponding to the internal sequence of the N2 gene. These primers were N2-F, 5'-ATTAGGCTTTCCGCTGGTGGGGACAT-3' (SEQ ID NO:16) and N2-R, 5'-GCATTCTGACTCCTGGGTCCT-GAGGATT-3' (SEQ ID NO:17).

Expression of the proteins was confirmed by Western blot analyses and immunofluorescence staining as follows. Quadruple VLP-expression cells were induced with Dox for 48 h, or left untreated as a control. The cells were then fixed in 4% paraformaldehyde for 10 min and immersed in 0.05% Triton-X 100 for 1 min. After blocking with 1% gelatin, the cells were incubated with distinct primary specific antibodies, followed with goat anti-mouse or goat anti-rabbit IgG conjugated with Cy3 dye. Fluorescence images were acquired by confocal microscopy (LSM 510 META NLO DuoScan, Carl Zeiss, GmbH). The antibodies used in this study were polyclonal: H3 (ab20084), N1 (ab21305), M1 (ab20734), annexin A2 (ab41803), and clathrin (ab21679) from Abcam (Cambridge, Mass.), β-actin (sc-1616-R) from Santa Cruz Biotechnology (Santa Cruz, Calif.), and monoclonal: M2 (ab5416), and tubulin (ab6160) from Abcam and H5 (MCA2660, used for IFA) from AbD Serotec (Raleigh, N.C.). Rabbit polyclonal antibody against H5 used for Western blotting was provided by Dr. Che Ma (Genomics Research Center, Academia Sinica).

In this study, mammalian cell culture-based approaches were used to generate influenza VLPs. To stably transfect the viral genes of HA, NA, M1, and M2 critical for VLP production into cultured Vero cells, such as Vero E6 cell, four gene expression cassettes were designed and placed into two vectors as illustrated (FIG. 5A). A tetracycline repressor gene and tet operator-regulated gene expression cassette were also inserted in the plasmid expressing M1 and M2, giving the vector pCI6/TO-M1-M2. By stable transfection of the M1-M2 vector into Vero cells, founder cells that would not express the M1-M2 transgene until doxycycline (Dox) induction were constructed. Another two tet operator-regulated, CMV promoter-driven expression cassettes were inserted separately into the other plasmid carrying HA and NA genes, giving the expression vector pCI4/TO-HA-NA. After stable transfection of pCI4/TO-HA-NA vector into an M1-M2 founder cell line, a mammalian-expressed VLP system in Vero cell was established.

To verify that co-expression of all four viral genes was indeed driven by the inducible promoter (CMV-TO), total cell lysates of quadruple-transfected Vero cell line of H3N2 were analyzed by Western blot with specific viral antibodies against H3, M1, and M2 (FIG. 5B). As there is no available antibody to N2, RT-PCR was used to confirm the expression of the N2 gene. The cellular localization of H3 was also observed by confocal laser scanning microscope (FIG. 5D). The utility of this system as an alternative platform to reverse genetics for vaccine development was shown by the simple substitution of a separate plasmid carrying the HA and NA genes of H3N2 with those of H5N1 (FIGS. 5C and 5E). The resulting quadruple H5N1-VLP cell line again co-expressed HA and NA, this time of the H5 and N1 varieties. Two subtypes of quadruple Vero cell lines that generated the putative H3N2- and H5N1-VLPs, respectively, have been constructed and verified. Vero cell expression systems for producing other influenza VLPs can also be constructed and verified using similar methods in view of the present disclosure.

Microcarrier Culture and Purification of Influenza VLPs Made from Vero Cells

To scale up the cultivation of VLP producer cells, 60 g microcarriers (HyClone) and cells (about $2 \times 10^8$) were added to a 3 L spinner flask (BellcoGlass com., Vineland, N.J.), stirred at around 35 rpm with a pendant glass ball, and maintained in minimal essential medium supplemented with 10% fetal bovine serum in a humidified incubator at 37° C. with 5% $CO_2$. After 7 days cultivation, the cells had attached to the surface of the collagen-coated microcarrier and grown to confluence. For VLP expression and secretion from cells, the culture medium was removed and replaced with serum-free medium (SFM4 MegaVir, HyClone) containing 1 μg/mL Dox to begin induction.

After Dox-induction for 72 h, the conditioned medium of VLPs producer cells was harvested, filtered with 0.45 μm Stericap, concentrated by Vivaflow 50 (Sartorius Stedim Biotech, Göttingen, Germany), and then layered onto a 30% sucrose-TNE (10 mM Tris-HCl, pH 7.4, 100 mM NaCl, 1 mM EDTA) cushion. Following centrifuge at 112,600×g for 2 h at 4° C. in a Beckman SW28 rotor (Beckman Coulter, Fullerton, Calif.), the resulting pellet was resuspended in TNE buffer, and further purified over a 20-30-60% sucrose gradient (112,600×g, 2 h at 4° C.). Finally, the banded VLPs were collected, dialyzed with TNE buffer overnight, and stored at ±80° C. To analyze the protein constituents of purified VLPs, the samples quantified by Quant-iT Protein Assay Kit (Invitrogen) were mixed with Lämmle SDS-PAGE sample buffer, boiled for 5 min, and separated in a 7.5-17.5% gradient gel.

The mammalian Vero cell system successfully produced influenza VLPs on a preclinical scale by stable co-expression of four viral proteins: M1, M2, HA and NA. Typically, the pilot production of 3 L-scale microcarrier systems yielded an average 1.2 mg/L medium of influenza VLPs after purification. Each inoculation of 3 L-culture attained $10^9$ cells and could be induced to continuously express VLPs three times.

Example 5

Characterization of Influenza VLPs Made by Vero Cells

Morphology and Antigen Presentation of Purified H3N2 VLPs and H5N1VLPs

Immunogold electron microscopy was performed on purified influenza VLPs made from Vero cells. Sucrose gradient purified influenza VLPs of 1 µg were adsorbed onto formvar/carbon-coated nickel grids (Electron Microscopy Sciences, Fort Washington, Pa.). After a 2 min wash with TBS buffer (50 mM Tris-HCl, pH 7.5, 150 mM NaCl), the sample was blocked with 1% BSA in TBS for 1 h. Primary antibody (10 µg/mL) was diluted in 1% BSA/TBS and adsorbed onto the grid for 1 h at room temperature. Following three washes with TBS, secondary gold-conjugated antibody was added for 1 h at room temperature. The grids were then washed twice with TBS, fixed with 1% glutaraldehyde, washed with water, and negatively stained with 2% uranyl acetate for 30 sec. The images of stained mammalian VLPs were captured using a Hitachi H-7000 transmission electron microscope.

The morphologies of mammalian VLPs purified from culture medium of transfected cells were negative stained with 2% uranyl acetate and observed by TEM as compared to their corresponding viruses propagated in Vero cells (FIGS. 6A and 6B).

The influenza VLPs displayed generally spherical morphologies and densely stained cores. The spike projections on the surface of VLPs were no different in appearance to those on authentic influenza viruses. The HA and NA glycoproteins on the surface of VLPs were immunogold labeled with individual specific antibodies, and counterstained with gold spheres coupled to secondary antibodies (FIGS. 6C and 6D).

Dynamic Light Scattering (DLS) Determination of Average Particle Size of Influenza VLPs In complement the morphology analysis by TEM, the average sizes of secreted VLPs in native solution were estimated by DLS assays. To be an effective vaccine, it has been proposed that particles ranging from 20 to 200 nm could facilitate the drainage of free antigens to the lymph nodes and induce strong responses in dendritic cells (DC) for long-term protective purposes [15]. Laser-based DLS can monitor changes in Brownian motion of nanoparticles in solution, giving information related to the average size and frequency distribution of particles.

Stock solutions of influenza VLPs were diluted to 0.1 µg/mL in 20 mM phosphate buffer at pH 7.4, passed through 0.45 µm filters, and analyzed on a Nano ZS particle-size analyzer (Malvern Zetasizer, Malvern Instruments Ltd, UK). For each sample analyzed by DLS, two consecutive measurements were taken on a single sample and measured with a light-scattering data collection time of 60 sec according to the manipulation instruction. The accompanying software (Nanov510) was used to convert the intensity-based measurement to a size distribution based on the number of particles in each size class, and was presented as a diagram of curves showing the frequency distribution of the sample where the area under the curve was proportional to the numbers of VLPs detected in the relevant size range. The average diameters of VLPs were then calculated as the mean size of VLP population±standard deviation (SD) of three independent experiments.

As shown in FIG. 7, DLS here revealed the average diameters of H3N2- and H5N1-VLPs were 108.2±17.9 nm and 125.6±10.5 nm, respectively, at pH 7.4, 25° C. The sizes of the VLPs are comparable to the sizes of their corresponding viruses, e.g., 133.5±15.4 nm and 104.1±12.4 nm for H3N2 and H5N1 viruses, respectively. The size distributions of both subtypes of VLPs ranged from 70-200 nm (95% CI), suggesting that the influenza VLPs produced by Vero cells were in the preferred size range for DC uptake and promise to stimulate a potent immune response (FIG. 7). DLS will be a useful approach to monitor the batch-to-batch consistency of VLPs by rapidly providing information on the whole population of particles. Together, the DLS and TEM measurements of influenza VLPs were consistent and showed the VLPs made by Vero cells to be of comparable size and morphology to native influenza viruses.

Identification of Influenza VLP Composition and VLP-Associated Cellular Proteins To verify the protein constituents of mammalian expressed VLPs, 10 µg of H3N2- and H5N1-VLPs were separated on a 7.5%-17.5% gradient gel, and stained with Coomassie blue (FIGS. 8A and 8C) or probed with specific antibodies against viral proteins in separate experiments (FIGS. 8B and 8D). Besides the viral proteins of HA, NA, M1, and M2, a wide spectrum of minor bands were also observed in the influenza VLPs similar to those in the authentic viruses (FIGS. 8A and 8C).

To identify the basic protein profiles of these VLPs, the more obvious protein bands (indicated by arrows in FIGS. 8A and 8C) were excised from the gels, subjected to in-gel trypsin digestions, and analyzed by liquid chromatography tandem mass spectrometry (LC/MS/MS). Briefly, the protein bands from 1-D gel were manually excised from the gel and cut into small pieces (~0.5 mm³). The gel pieces were washed in a microcentrifuge tube with a solution containing 50% methanol and 5% acetic acid for 2-3 h, twice with a solution of 25 mM $NH_4HCO_3$ in 50% acetonitrile for 10 min each, and then dried in a vacuum centrifuge. After DTT reduction and iodoacetamide alkylation, a solution containing 75 ng of sequencing grade modified trypsin (Promega Corporation, Madison, Wis.) in 25 µL of 25 mM $NH_4HCO_3$ was added and incubated with dried gel pieces at 37° C. for 12-16 h. Following digestion, tryptic peptides were extracted twice with 50% acetonitrile containing 5% formic acid for 15 min each time with vortex. The extracted solutions were pooled and evaporated to dryness under vacuum. The dried pellet was re-dissolved in 10-20 µL of 0.1% formic acid for LC/MS/MS analysis as described below. The NanoLC-nanoESi-MS/MS analysis was performed on a nanoAcquity system (Waters, Milford, Mass.) connected to an LTQ-Orbitrap XL hybrid mass spectrometer (Thermo Electron, Bremen, Germany) equipped with a PicoView nanospray interface (New Objective, Woburn, Mass.). Peptide mixtures were loaded onto a 75 µm ID, 25 cm length C18 BEH column (Waters) packed with 1.7 µm particles with a pore size with of 130 Å and were separated using a segmented gradient in 90 min from 5% to 50% solvent B (acetonitrile with 0.1% formic acid) at a flow rate of 300 mL/min and a column temperature of 35° C. Solvent A was 0.1% formic acid in water. The mass spectrometer was operated in the data-dependant mode. Briefly, survey full-scan MS spectra were acquired in the orbitrap (m/z 350-1600) with the resolution set to 60,000 at m/z 400 and automatic gain control (AGC) target at 106. The 10 most intense ions were sequentially isolated for CID MS/MS fragmentation and detection in the linear ion trap (AGC target at 7000) with previously selected ions dynamically excluded for 90 sec. Ions with single and/or unrecognized charge state were also excluded.

The MS and MS/MS raw data were processed with Bioworks 3.3.1 and searched against an in-house generated NCBI protein database, using a Mascot Daemon 2.2 server. Search criteria used were trypsin digestion, variable modifications set as carbamidomethyl (C) and oxidation (M), allowing up to 2 missed cleavages, mass accuracy of 10 ppm on the parent ion and 0.60 Da on the fragment ions.

The major VLP constituents identified by searching against the NCBI database are shown as Tables 1 and 2. It was found that HA and NA proteins of mammalian VLPs were distributed in multiple gel slices in addition to the expected locations shown in Table 1. This likely reflects the fact that they are the most abundant proteins in VLPs and form HA and NA protein oligomers (FIGS. 8B and 8D).

In addition, another 22 VLP-associated cellular proteins were identified, which are identical or functionally analogous to those cellular proteins commonly found in the interior or exterior of influenza virions [16]. Most of them could be classified into functional groups including cytoskeleton protein, extra cellular matrix (ECM) proteins, heat shock proteins, annexins, tetraspanins, and glycolytic enzymes.

TABLE 1

Viral and cellular proteins associated with influenza VLPs identified by mass spectrometry (LC/MS/MS). SDS-PAGE and LC/MS/MS Analysis

| Protein Type | Protein Name | Mass (Da) | Protein band number[a] H5N1/H3N2* | Mascot score[b] | Sequence coverage (%)[c] | Reported in influenza virion[d] |
|---|---|---|---|---|---|---|
| Viral proteins | Hemagglutinin (H5) | 64163 | 5, 6, 10$ | 227, 812, 1053 | 26, 18, 40 | yes |
| | Neuraminidase (N1) | 51298 | 6 | 71 | 10 | |
| | Hemagglutinin (H3) | 63595 | /4 | /239 | /24 | |
| | Neuraminidase (N2) | 52018 | /5 | /230 | /40 | |
| | Matrix 1 protein (M1) | 27860 | 10/10 | 35/45 | 36/16 | |
| | Matrix 2 protein (M2) | 11157 | 11/11 | 34/44 | 50/35 | |
| Cytoskeletal proteins | β-actin | 41710 | 8/8 | 1519/447 | 72/73 | yes |
| | β-tubulin | 49639 | 7/7 | 41/655 | 15/72 | yes |
| | myosin IA | 118204 | 2/2 | 175/41 | 7/2 | tropomyosin 4 & 1 |
| | Similar to myosin IC | 107102 | 3/3 | 898/107 | 42/15 | |
| ECM proteins | integrin alpha 3 | 118333 | 2/2 | 896/69 | 27/20 | Integrin beta 1 |
| | integrin alpha 5 | 115919 | 2/2 | 687/174 | 37/22 | |
| Heat shock proteins | Heat shock 90 kDa protein | 83185 | 4/4 | 435/368 | 40/43 | HSP 27 kDa |
| | Heat shock 70 kDa protein | 72288 | 5/5 | 615/503 | 54/50 | |
| | Heat shock 27 kDa protein | 22768 | 6 | 112 | 44 | yes |
| Annexin | annexin A11 | 54443 | 9/7 | 284/282 | 38/38 | yes |
| | annexin A2 | 53564/ 38576 | 7, 9/ 7, 9 | 1087, 361/ 153, 613 | 43, 41/ 26, 49 | yes |
| Tetraspanin | CD81 molecule | 25741 | 6 | 117 | 33 | yes |
| | CD9 molecule | 25380 | 7 | 27 | 11 | yes |
| Glycolytic enzymes | enolase 1 | 47182 | 9 | 1011 | 70 | yes |
| | Similar to phosphoglycerate kinase 1 | 44558 | 8 | 572 | 71 | Phosphoglycerate kinase |
| | pyruvate kinase | 64479 | 1/6 | 248/354 | 45/51 | yes |
| | glyceraldehyde-3-phosphate dehydrogenase | 35959 | 6/6 | 64/48 | 23/25 | yes |
| Unclassified proteins | 2',3'-cyclic nucleotide 3' phosphodiesterase | 47509 | 8 | 306 | 56 | yes |

TABLE 1-continued

Viral and cellular proteins associated with influenza
VLPs identified by mass spectrometry (LC/MS/MS).
SDS-PAGE and LC/MS/MS Analysis

| Protein Type | Protein Name | Mass (Da) | Protein band number[a] H5N1/H3N2* | Mascot score[b] | Sequence coverage (%)[c] | Reported in influenza virion[d] |
|---|---|---|---|---|---|---|
| | Aldo-keto reductase family 1 | 35992 | 7 | 99 | 23 | Yes |
| | WD repeat domain 18 | 48167 | 8 | 78 | 18 | WD repeat-containing protein 1 |
| | Gamma-glutamyl-transferase 1 | 61261 | 6/6 | 76/71 | 4/10 | Yes |
| | Peroxiredoxin 2 | 21878 | 7 | 28 | 9 | Peroxiredoxin 1 |

[a]Excised protein bands were numbered as indicated by arrows 1-11 of FIG. 4A and C.
[b]For this search a Mascot score ≥ 25 is significant (p < 0.05).
[c]Sequence coverage is based on peptides with unique sequence.
[d]Viral and cellular proteins have been reported in influenza virion [17].
*The band number, Mascot score, and sequence coverage of cellular proteins both identified in H5N1- and H3N2-VLPs are presented as A/B.
$The band number, Mascot score, and sequence coverage of a single protein distributed in multiple locations is presented as A, B.

Apart from those common proteins identified in virion and VLPs, several unique cellular proteins (as listed in Table 2) were also identified in influenza VLPs with very high Mascot scores in LC/MS/MS analysis. These proteins possibly involved in VLPs biosynthesis.

For real viruses, recruitment or encapsidation of some cellular proteins into the virion may be a critical behavior supporting the completion of the life cycle by some specific interaction with viral proteins or RNA. However, in this case, the mammalian influenza VLP has the components of viral (by transfection) and cellular proteins (by recruitment) without package of any viral genetic material. The cellular proteins identified in the influenza VLPs might be actively involved in the normal virus life cycle, especially during virus assembly and budding from the host cells.

TABLE 2

Unique cellular proteins identified by LC/MS/MS with high Mascot scores in mammalian VLPs.

| Protein Name | Mass (Da) | Protein band number[a] H5N1/H3N2* | Mascot score[b] | Sequence coverage (%)[c] |
|---|---|---|---|---|
| Clathrin heavy chain 1 (Cytoplasmic vesicles formation | 192276 | 1 | 3242 | 63 |
| Spectrin (interacts with actin) Beta (non-erythrocytic) | 274472 | 1 | 1146 | 35 |
| Plexin B2 (interacts with cytoskeleton) | 203451 | 1 | 757 | 26 |
| Similar to CD109 | 161515 | 1 | 738 | 23 |
| Prostaglandin F2 receptor negative regulator | 116885 | 2/2 | 1035/136 | 44/18 |
| Na+/K+-ATPase alpha 1 | 112838 | 3/3 | 1266/452 | 42/29 |
| Tumor rejection antigen (gp96) 1 | 92555 | 3/3 | 1016/614 | 52/60 |
| Flotillin I | 47384 | 9 | 1048 | 68 |

[a]Excised protein bands were numbered as indicated by arrows 1-11 of FIG. 4A and C.
[b]For this search a Mascot score ≥ 25 is significant (p < 0.05).
[c]Sequence coverage is based on peptides with unique sequence.
*The band number, Mascot score, and sequence coverage of cellular proteins both identified in H5N1- and H3N2-VLPs are presented as A/B.

To characterize the functionality of HA spike on mammalian VLPs, hemagglutination assays were performed (FIG. 8E). VLP preparations reacted with 0.75% guinea pig erythrocytes had significant hemagglutination activities, with titers of $2^7$ for H3N2-VLPs and $2^6$ for H5N1-VLPs in samples containing 3.5 μg of VLPs. Both H3N2 and H5N1 viruses of same amount as VLPs were at similar titers ($2^7$) of HA activity. This result suggests the HA spikes compassing around the surface of mammalian VLPs are in a native orientation and function as those of active authentic viruses.

Generally, the results of two independent LC/MS/MS analyses of H5N1- and H3N2-VLPs and Western blotting in this study resemble the reported proteome of influenza virus [16], which suggests that the assembly of influenza VLPs shares much similarity with real virus assembly and escape. Taken together, these data confirm that the mammalian-expressed influenza VLPs are very similar to the authentic viruses, a considerable advantage to their use in further vaccine development.

Confirmation of Cellular Proteins Associated and Incorporated into Influenza VLPs Following proteomic identification of incorporated cellular proteins, several viral and associated cellular proteins were further characterized by Western blot and immunogold labeling. To rule out the possibility that identified proteins may be due to non-specific contamination such as co-purification of microvesicles or exosomes with VLPs, the mammalian influenza VLP preparations were subjected to a protease protection assay that has been shown to efficiently remove microvesicles from HIV-1 virion preparations [17,18].

Purified H5N1-VLPs equivalent to 50 μg of proteins were incubated with or without 20 μg of MSG-Trypsin (G-Biosciences, St. Louis, Mo.) in 20 mM Tris-HCl, pH 8.0 and 1 mM $CaCl_2$ for 18 h at 37° C. After trypsin incubation, the treated and untreated VLPs preparations were separately diluted to 7 mL with THE buffer containing 30 μM PMSF (Sigma, St. Louis, Mo.), and concentrated through a 20% sucrose cushion by ultracentrifugation (200,000×g, 2 h at 4° C. in a Beckman SW41Ti rotor) and then subjected to Western blot analyses with antibodies against HA, NA, M1, M2, β-actin, tubulin, annexin A2, and clathrin (FIG. 9A).

Both HA and NA proteins were lost from the VLPs after trypsin digestion, demonstrating that these proteins were located on the outside of the membrane envelope, integral and attached to the VLP surface. Most co-purified contaminants were eliminated by the protease digestion. However, several representative cellular proteins expected to be inside the virion such as actin, tubulin, and annexin A2 were still found to be present in the protease-digested VLPs, which indicates that these cellular proteins were specifically incorporated into the structure of VLPs (FIG. 9A).

In contrast, a unique cellular protein identified in this study, clathrin heavy chain, an important component of the clathrin-coated pits mediating the endocytosis of many receptors, ion channels, transporters, and other transmembrane proteins as well as various soluble macromolecules and viruses, was lost following protease treatment (FIG. 9A) [19,20]. This finding raised two possibilities: Firstly, clathrin is associated with contaminants rather than the VLPs, or secondly, that clathrin is indeed incorporated into VLPs but is exposed on the surface like HA and NA. To resolve this issue, immunogold labeling was used to look for the presence of clathrin on the surface of intact, undigested VLPs (FIG. 9B). This assay did show clathrin staining on the surface of intact VLPs, just as for HA and NA (FIGS. 6C and 6D). This new discover, i.e., clathrin, an endocytosis mediator protein, was specifically associated with secretory influenza VLPs, can have implications for the route of VLP biosynthesis and for the late stage of virus assembly and budding.

The proteomic analysis and protease protection assays of the secreted VLPs revealed that 22 cellular proteins associated with authentic virus of H1N1 were also specifically incorporated into mammalian H3N2 and H5N1 VLPs (Table 1 and FIG. 8). Among these proteins, tubulin, actin, annexins, enolase, GAPDH, gamma-glutamyltransferase, and HSP 27 have been demonstrated to be derived from lipid raft by proteomic analysis in previous studies [39,40,41,42,43]. Correct assembly and budding of influenza virus requires cooperative action by multiple viral proteins with the lipid bilayers and genomic RNA as well as host proteins [44,45]. In VLP systems, except for the interactions involved in viral RNAs and capsid proteins, the events related to virus particle release are thought to be congruent to real virus assembly and release. A number of the proteins identified in mammalian influenza VLPs shed light on their roles in the influenza virion during assembly/budding stages of the infection process. The similarity between VLP proteomes and the virus cellular protein content also suggests the budding behaviors and constituents of mammalian VLPs are very similar to those of authentic viruses, and therefore that VLPs expressed from a mammalian cell-based system and constituting a non-pathogenic pseudovirion with very similar properties apart from genomic content are most likely to be a promising vaccine candidate.

Glycosylation Profiling of Influenza VLPs

Glycosylation of viral surface antigens is critical for immune recognition, receptor binding, inflammation, and pathogenicity, and therefore has a major influence on the efficacy of vaccine antigens [21,22]. For example, the common phenomenon of amino acid substitutions of the viral HA due to egg-adaptation and the consequent altered glycosylations severely affect the antigenicity of influenza virus [23]. As demonstrated by N-glycan footprinting analyses of HA, the use of different cell lines for replication of the same virus results in different N-glycosylation patterns on HA, which can be attributed to host-mediated changes in the amino acid sequence and potential glycosylation sites of HA, further influencing the antigenic properties of manufactured virus [24,25,26]. Therefore, the glycosylation status of HA and NA antigens in the VLPs were assessed to look for any change that would affect the antigenicity and immune response of a VLP-based vaccine.

Deglycosylation assay of proteins in influenza VLPs were performed. Purified influenza VLPs equivalent to 10 µg of proteins were denatured by heating at 100° C. for 10 min in the presence of 0.5% SDS and 40 mM DTT. Next, either PNGase F or Endo-H (New England Biolabs, Ipswich, Mass.) was added and the mixture incubated at 37° C. for 1 h with distinct reaction buffers, before protein gel electrophoresis and subsequent Western blot analyses.

The N-glycosylation patterns of H3N2- and H5N1-VLPs produced from Vero cells were compared to the glycan profiles of authentic viruses by performing deglycosylation assays with N-endoglycosidases PNGase F and Endo-H. PNGase F can remove all types of N-linked oligosaccharides from glycoproteins such as complex, hybrid, and high-mannose types, whereas Endo-H cleaves the chitobiose core of high-mannose and hybrid oligosaccharides from N-linked glycoproteins. As shown in FIG. 10A, most of the modified HA and NA (labeled as HA 1+NA and HA2**) in purified H5N1-VLP was seen as two major bands in the SDS-PAGE gel before degylcosylation (lane 1); their apparent molecular masses were around 56 and 30 kDa, respectively (FIGS. 10B and 10C, lanes 1). After treatment of H5N1-VLPs with PNGase F, HA1, HA2, and NA bands increased their mobility to molecular masses of 40, 27, and 52 kDa, respectively (FIGS. 10A, 10B, and 10C, lanes 2), demonstrating that the two predominant viral surface antigens were mainly glycosylated by N-linked oligosaccharides. Of note, one form of NA marked as (π) in FIG. 10C whose mobility was not changed by reaction with both enzymes suggests NA may have other types of post-translational modification. When the glycosylated HA from H5N1-VLP was treated with Endo-H, the deglycosylation reaction was only partial, therefore the original bands and the Endo-H digested residue bands marked as (#) of HA1 and HA2 can be seen simultaneously in FIG. 10B, lane 6. However, the HA of H5N1 virus propagated in Vero cells was resistant to Endo-H digestion, suggesting the glycans linked to the viral HA are complex type (FIG. 10B, lane 8). The partial sensitivity of HA in H5N1-VLPs to Endo-H may be a result of hybrid glycan chains due to the overwhelming expression of viral protein thus incomplete glycosylation. However, as the great majority of NA can be deglycosylated by Endo-H, the NA proteins of H5N1-VLP may possess more high-mannose than complex glycans (FIG. 10C, lane 4). In parallel, the deglycosylation assays were performed on H3N2-VLPs (FIG. 10D). In H3 glycoprotein, Endo-H treatment deduced molecular mass 16 kDa and PNGase F treatment reduced 25 kDa, suggesting a higher content of high-mannose or hybrid types than complex type in the H3 glycan pool (FIG. 10D).

The results suggest that VLPs generated from Vero cells have similar glycosylation profiles to the authentic viruses that result from infection in the same host species. Collectively, the VLPs made from Vero cells resemble the real viruses in particle size, morphology, protein composition, and glycosylation profiles and therefore offer great potential as safe and effective influenza vaccine antigens.

Example 6

Virus Propagation, Hemagglutination and Serological Tests

Influenza virus, A/Taiwan/083/2006 and H5N1 (NIBRG-14) strains (National Institute for Biological Standards and Control, Potters Bar, U.K.) were propagated in Vero (for VLP comparison) or MDCK cells (for viral challenge). To assess hemagglutination, 3.5 µg of VLPs or virus and their serial 2-fold dilutions were mixed with a 0.75% suspension of guinea pig red blood cells in 96 well plates. Plates were incubated for 1 h and hemagglutination was assessed by eye. The highest dilution of VLPs or virus giving hemagglutination was determined as 1 HA unit.

To assess hemagglutination inhibition (HI) titers, sera were treated with a receptor-destroying enzyme and heat-inactivated (30 min, 56° C.), tested in 2-fold dilutions starting with an initial dilution of 1:10, then mixed with 8 HA units of H5N1-VLP and incubated at room temperature. After 1 h, a 0.75% suspension of guinea pig red blood cells was added and hemagglutination was assessed 2 h later by eye. HI titer as expressed as the reciprocal of the highest dilution that showed 50% inhibition of hemagglutination. All samples were tested in triplicate.

ELISA plates (Nunc) were coated with indicated H5 glycoprotein, VLPs, or virus at 4° C. overnight and blocked with 1% casein (Blocker Casein, Pierce, Rockford, Ill.) in PBS. ELISA plates were then incubated with serum samples of indicated dilution at 37° C. for 1 h, traced with HRP-conjugated secondary Ab, and developed color with TMB substrate (Pierce). They were washed with PBST five times between each step of ELISA. Finally, the ELISA was read out with absorbance of 450 nm wavelength ($A_{450}$) by a microplate reader (Power Wave XS, Bio-Teck) and results were plotted.

Example 7

Vaccination and Viral Challenge

Female BALB/c mice (6 weeks old) were purchased from National Laboratory Animal Center, randomly assigned to receive two doses of vaccine 21 days apart. Vaccines of 0.3 µg, 1.5 µg, 2.5 µg, or 10 µg H5N1-VLPs comprised of 0.054 µg, 0.27 µg, 0.45 µg, or 1.8 µg of H5 glycoprotein in sequence, and whole virus vaccine were grown in chicken embryo, inactivated by formalin and applied at 2.5 µg or 10 µg doses. Vaccines or PBS (as mock control) were given by intramuscular injection into the quadriceps. Blood was collected from mice via the retro-orbital sinus, transferred to a tube containing a serum separator and clot activator, and allowed to clot at room temperature. Sera were removed after centrifugation and stocked at −80° C. The immunized mice were challenged intranasally with a recombinant H5N1 virus, NIBRG-14, with a lethal dose (100-fold lethal dose to 50% of mice) as performed previously [48]. The mice were monitored daily for 14 days after the challenge for survival and morbidity (i.e. weight loss, inactivity and body temperature). All animal experiments were evaluated and approved by the Institutional Animal Care and Use Committee of Academia Sinica.

Humoral Immune Response of VLPs

To investigate the vaccine effect of mammalian expressed VLPs, mice were vaccinated with VLPs without adjuvantation. The vaccinated mice were analyzed for the antibody response and protection against viral infection. Mice (BALB/c; n=12) were vaccinated twice (day 0 and 21) via intramuscular injection with purified H5N1-VLP or inactivated whole virus of H5N1-pseudotyped vaccine strain (recombinant H5N1 engineered by reverse genetics) at two antigen doses (2.5 µg and 10 µg). Blood samples were collected to analyze humoral immune response before primary (day −1) and after immunizations (day 14 and 35) (FIG. 11A). Sera were tested for influenza virus-specific IgG antibodies by ELISA against baculovirus produced H5 glycoprotein, or mammalian expressed H5N1-VLP and H3N2-VLP (FIG. 11B). Mice vaccinated with H5N1-VLP showed a robust response of IgG antibodies against H5 protein and H5N1-VLP. The ELISA titers of both antigen doses against H5 protein and H5N1-VLP were higher than 1:200,000, in contrast their titers against H3N2-VLP were insignificant (<1:25,000). This suggests that H5N1-VLP was highly immunogenic to stimulate highly specific antibodies against the H5 epitopes. Whole virus vaccine stimulated ELISA titers of approximate 1:100,000, while being highly immunogenic, the H5-specific titer was considerably lower than the VLP vaccine (FIG. 11B). However, ELISA titers for VLP vaccine group reduced to the level of whole virus vaccine group when whole virus was used as ELISA antigen (FIG. 11C). This suggests immunity of H5N1-VLP was more potent and specific to H5 glycoprotein, it may arise from the higher HA content in the VLPs than the viruses. Specificity of the VLP-induced antibody was further detected by Western blotting against all proteins of VLP and the virus. Indeed, the IgG antibodies detected only signals corresponding to the H5 glycoprotein, both HA1 and HA2 fragments in the VLP and virus (FIG. 11D). The lack of signal detecting other host and viral proteins in this experiment indicated the VLP was as "clean" as the inactivated split virus and subunit vaccines, only immunogenic toward the HA glycoprotein.

The IgG antibody isotypes distribution elicited by vaccination is indicative of the type of T cell immune response, as subsets of antigen-specific helper T cell via secreting different cytokines regulate the production of different IgG isotypes. The IgG1 isotype in mice is believed to signal a Th2 response, whereas the IgG2a isotype indicates more of a Th1 response. ELISA test was further used to measure the class and IgG isotypes of antigen-specific antibodies in response to the VLP and whole virus vaccines. As shown, the antibodies induced by VLP were predominantly IgG1 isotype, much less in IgG2a, and low or undetectable in IgG2b and IgA (FIG. 11E, left). However, the antibodies induced by whole virus vaccine were mainly IgG2a, less in IgG1, and insignificant in IgG2b and IgA. These results suggest that mammalian VLP vaccine at the two antigen doses induced primarily a Th2 response, whereas whole virus vaccine stimulated a mixed Th1/Th2 response with Th1 more dominant at higher antigen-dosage.

Vaccine Induced Hemagglutination-Inhibition (HI) Activity and Protection Against Viral Infection The HI assay is the most widely accepted serological test for influenza immunity and is the gold standard measure of functional HA-specific antibodies after vaccination. The serological criteria currently used for approval of pandemic vaccines in the US are based on seasonal influenza vaccines, with seroconversion (i.e. a minimum 4-fold rise in HI titer) rate >40% and seroprotection (i.e. HI titer >1:40) rate ≥70% in adults younger than 65. Antibodies elicited by each vaccine candidate were evaluated for ability to inhibit the VLP-induced agglutination of guinea pig red blood cells (FIG. 11E). After the second dose (day 35), the seroprotective HI titers were induced in 83.3% of mice received 2.5 µg and 10 µg VLP vaccine with mean HI titer reached about 1:60. When the antigen dose of VLP vaccine decreased to 0.3 µg and 1.5 µg, the reciprocal seroprotective rate dropped to 12.5% and 25%. Seroprotective rates of corresponding whole virus vaccine were 75% and 87.5% in parallel experiments.

Figure 12:
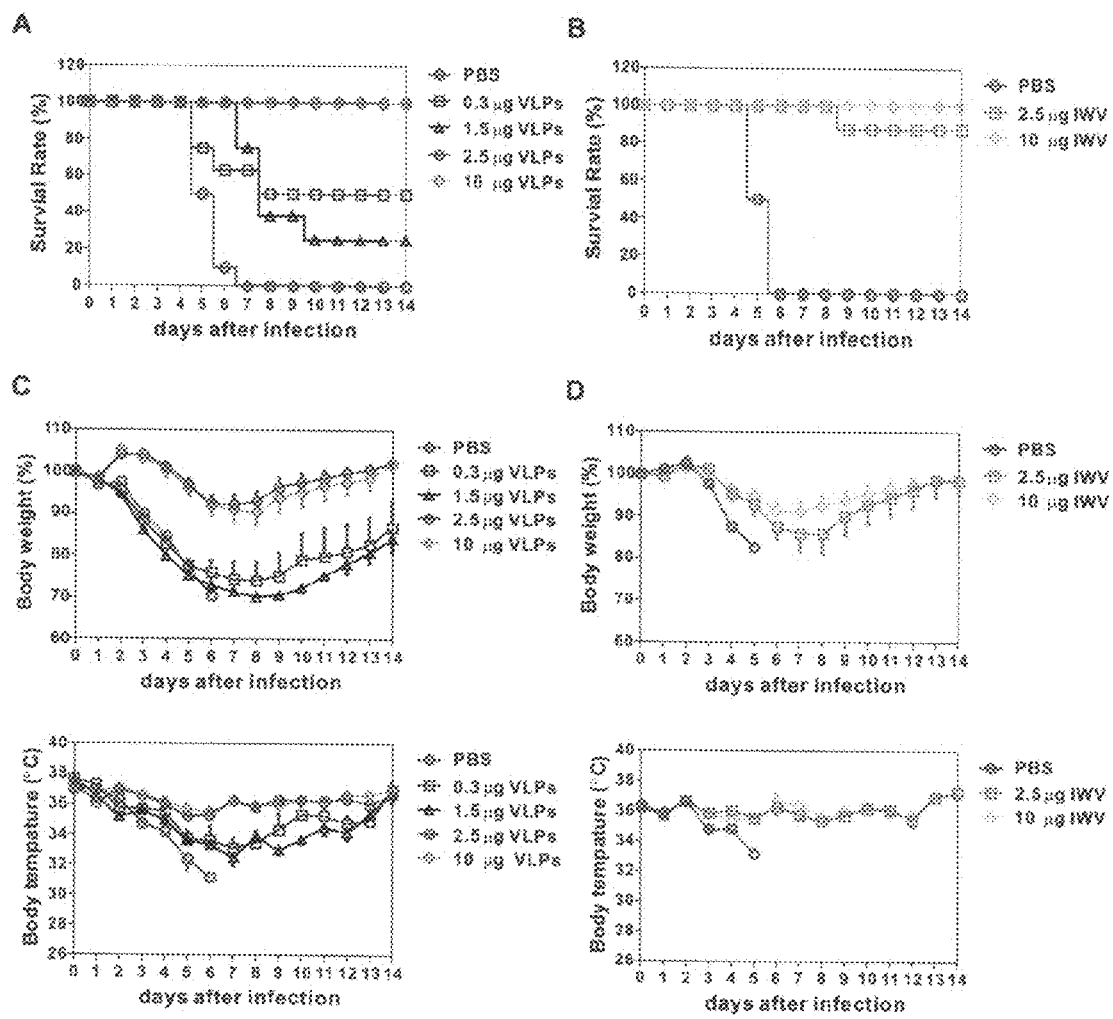

All mice vaccinated with VLP vaccine, whole virus vaccine or mock control were challenged intranasally with predetermined lethal dose of H5N1-pseudotyped recombinant virus to evaluated the protective efficacy of each vaccine candidate. All mice received 2.5 µg and 10 µg VLP vaccine survived from the viral challenge, in contrast to the mock control mice that all died within 7 days after infection (FIG. 12A). Lower dose (0.3 μg and 1.5 μg) of VLP vaccine indeed compromised survival rate (50% and 25%, respectively), which is consistent with a lower seroprotection rate. Also, whole virus vaccine (2.5 μg and 10 μg) was protective to the viral challenge except one mouse in the 2.5 μg dose group lost >30% body weight (FIG. 12B). Body weight and temperature changes of test mice were indicative illness and mice vaccinated with high-dose VLP and whole virus vaccine recovered their original weight by day 13 post-challenge, a result consistent with the survival outcome. However, mice vaccinated with low-dose VLP had more prominent weight loss and temperature decrease, despite some of the survivors recovered at later time.

Efficacy of the VLP created by mammalian expression system to be a new influenza vaccine for human and animal use is demonstrated for the first time in the present study. For example, it was demonstrated that vaccination with mammalian expressed VLPs provided full protection against lethal infection against the homologous strain challenge at doses as low as 2.5 μg VLP (0.45 μg HA) using two dose regimen in BALB/c mice.

The full protection of mammalian VLP vaccine was well-correlated with functional antibody responses (HI assay), which is the licensure criteria accepted for yearly interpandemic vaccines. The presence of numerous cellular proteins integrated in the mammalian expressed VLP may raise concerns of autoimmunity. It was shown that host protein contents of the VLP were akin to the authentic virus in varieties and quantity. Both Vero and Vero E6 cell lines are currently considered as the most widely acceptable cell substrate by regulatory authorities to produce a wide range of viruses for manufacturing human-use vaccine, including influenza, polio virus, rabies virus, smallpox, vesicular stomatitis virus, herpes simplex virus and rotavirus, etc. Furthermore, Vero cells are the only recommended cells to prepare viruses for vaccine production by reverse genetics in the document: "WHO guidance on development of influenza vaccine reference viruses by reverse genetics". For this reason, we chose Vero and Vero E6 cell lines rather than any other human or non-human mammalian cell lines to produce VLPs. In fact, our studies demonstrate that vaccination in mice with VLP void of adjuvant formulation elicited high-titer antibodies against HA only but not other proteins (FIG. 11). Vaccinated mice survived perfectly with two doses of VLP vaccines at 2.5 μg and 10 μg levels via intramuscular immunization, and they all survived the subsequent lethal viral challenge. No adverse effect was found before and after viral challenge throughout the 56-day experiment. Worth of note, the humoral immune response elicited by mammalian expressed VLPs is different from that of baculovirus-derived VLPs, suggesting a distinction between the two forms of VLPs. It may attribute to the glycosylation profile, host protein contents, the overall particle structure that present antigens, or something else.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

References

1. Nicholson K G (2009) Influenza and vaccine development: a continued battle. Expert Rev Vaccines 8: 373-374.
2. Sambhara S, Stephenson I (2009) Moving influenza vaccines forward. Expert Rev Vaccines 8: 375-377.
3. Kang S M, Yoo D G, Lipatov A S, Song J M, Davis C T, et al. (2009) Induction of long-term protective immune responses by influenza H5N1 virus-like particles. PLoS One 4: e4667.
4. Demicheli V, Rivetti D, Deeks J J, Jefferson T O (2004) Vaccines for preventing influenza in healthy adults. Cochrane Database Syst Rev: CD001269.
5. Trollfors B (2006) General vaccination of children against influenza? Acta Paediatr 95: 774-777.
6. Johansson B E, Brett I C (2007) Changing perspective on immunization against influenza. Vaccine 25: 3062-3065.
7. Roy P, Noad R (2008) Virus-like particles as a vaccine delivery system: myths and facts. Hum Vaccin 4: 5-12.
8. Garland S M, Hernandez-Avila M, Wheeler C M, Perez G, Harper D M, et al. (2007) Quadrivalent vaccine against human papillomavirus to prevent anogenital diseases. N Engl J Med 356: 1928-1943.
9. Bright R A, Carter D M, Daniluk S, Toapanta F R, Ahmad A, et al. (2007) Influenza virus-like particles elicit broader immune responses than whole virion inactivated influenza virus or recombinant hemagglutinin. Vaccine 25: 3871-3878.
10. Bright R A, Carter D M, Crevar C J, Toapanta F R, Steckbeck J D, et al. (2008) Cross-clade protective immune responses to influenza viruses with H5N1 HA and NA elicited by an influenza virus-like particle. PLoS One 3: e1501.
11. Galarza J M, Latham T, Cupo A (2005) Virus-like particle vaccine conferred complete protection against a lethal influenza virus challenge. Viral Immunol 18: 365-372.
12. Mahmood K, Bright R A, Mytle N, Carter D M, Crevar C J, et al. (2008) H5N1 VLP vaccine induced protection in ferrets against lethal challenge with highly pathogenic H5N1 influenza viruses. Vaccine 26: 5393-5399.
13. Tao P, Luo M, Zhu D, Qu S, Yang Z, et al. (2009) Virus-like particle vaccine comprised of the HA, NA, and M1 proteins of an avian isolated H5N1 influenza virus induces protective immunity against homologous and heterologous strains in mice. Viral Immunol 22: 273-281.
14. Quan F S, Huang C, Compans R W, Kang S M (2007) Virus-like particle vaccine induces protective immunity against homologous and heterologous strains of influenza virus. J Virol 81: 3514-3524.
15. Manolova V, Flace A, Bauer M, Schwarz K, Saudan P, et al. (2008) Nanoparticles target distinct dendritic cell populations according to their size. Eur J Immunol 38: 1404-1413.
16. Shaw M L, Stone K L, Colangelo C M, Gulcicek E E, Palese P (2008) Cellular proteins in influenza virus particles. PLoS Pathog 4: e1000085.
17. Ott D E, Coren L V, Kane B P, Busch L K, Johnson D G, et al. (1996) Cytoskeletal proteins inside human immunodeficiency virus type 1 virions. J Virol 70: 7734-7743.
18. Wubbolts R, Leckie R S, Veenhuizen P T, Schwarzmann G, Mobius W, et al. (2003) Proteomic and biochemical analyses of human B cell-derived exosomes. Potential implications for their function and multivesicular body formation. J Biol Chem 278: 10963-10972.
19. Kirchhausen T (2000) Three ways to make a vesicle. Nat Rev Mol Cell Biol 1: 187-198.
20. Brodsky F M, Chen C Y, Knuehl C, Towler M C, Wakeham D E (2001) Biological basket weaving: formation and function of clathrin-coated vesicles. Annu Rev Cell Dev Biol 17: 517-568.
21. Hamby S E, Hirst J D (2008) Prediction of glycosylation sites using random forests. BMC Bioinformatics 9: 500.

22. Schwarzer J, Rapp E, Reichl U (2008) N-glycan analysis by CGE-LIF: profiling influenza A virus hemagglutinin N-glycosylation during vaccine production. Electrophoresis 29: 4203-4214.
23. Robertson J S (1987) Sequence analysis of the haemagglutinin of A/Taiwan/1/86, a new variant of human influenza A(H1N1) virus. J Gen Virol 68 (Pt 4): 1205-1208.
24. Romanova J, Katinger D, Ferko B, Voglauer R, Mochalova L, et al. (2003) Distinct host range of influenza H3N2 virus isolates in Vero and MDCK cells is determined by cell specific glycosylation pattern. Virology 307: 90-97.
25. Schwarzer J, Rapp E, Hennig R, Genzel Y, Jordan I, et al. (2009) Glycan analysis in cell culture-based influenza vaccine production: influence of host cell line and virus strain on the glycosylation pattern of viral hemagglutinin. Vaccine 27: 4325-4336.
26. Skehel J J, Stevens D J, Daniels R S, Douglas A R, Knossow M, et al. (1984) A carbohydrate side chain on hemagglutinins of Hong Kong influenza viruses inhibits recognition by a monoclonal antibody. Proc Natl Acad Sci USA 81: 1779-1783.
27. Evans T G, Bonnez W, Rose R C, Koenig S, Demeter L, et al. (2001) A Phase 1 study of a recombinant viruslike particle vaccine against human papillomavirus type 11 in healthy adult volunteers. J Infect Dis 183: 1485-1493.
28. Koutsky L A, Ault K A, Wheeler C M, Brown D R, Barr E, et al. (2002) A controlled trial of a human papillomavirus type 16 vaccine. N Engl J Med 347: 1645-1651.
29. Galarza J M, Latham T, Cupo A (2005) Virus-like particle (VLP) vaccine conferred complete protection against a lethal influenza virus challenge. Viral Immunol 18: 244-251.
30. Chen B J, Leser G P, Morita E, Lamb R A (2007) Influenza virus hemagglutinin and neuraminidase, but not the matrix protein, are required for assembly and budding of plasmid-derived virus-like particles. J Virol 81: 7111-7123.
31. Ali A, Avalos R T, Ponimaskin E, Nayak D P (2000) Influenza virus assembly: effect of influenza virus glycoproteins on the membrane association of M1 protein. J Virol 74: 8709-8719.
32. Enami M, Enami K (1996) Influenza virus hemagglutinin and neuraminidase glycoproteins stimulate the membrane association of the matrix protein. J Virol 70: 6653-6657.
33. Gregoriades A, Frangione B (1981) Insertion of influenza M protein into the viral lipid bilayer and localization of site of insertion. J Virol 40: 323-328.
34. Gomez-Puertas P, Albo C, Perez-Pastrana E, Vivo A, Portela A (2000) Influenza virus matrix protein is the major driving force in virus budding. J Virol 74: 11538-11547.
35. McCown M F, Pekosz A (2006) Distinct domains of the influenza a virus M2 protein cytoplasmic tail mediate binding to the M1 protein and facilitate infectious virus production. Virol 80: 8178-8189.
36. Ruigrok R W, Barge A, Durrer P, Brunner J, Ma K, et al. (2000) Membrane interaction of influenza virus M1 protein. Virology 267: 289-298.
37. Johansson B E, Bucher D J, Pokorny B A, Mikhail A, Kilbourne E D (1989) Identification of PR8 M1 protein in influenza virus high-yield reassortants by M1-specific monoclonal antibodies. Virology 171: 634-636.
38. McMurry J A, Johansson B E, De Groot A S (2008) A call to cellular & humoral arms: enlisting cognate T cell help to develop broad-spectrum vaccines against influenza A. Hum Vaccin 4: 148-157.
39. Blonder J, Terunuma A, Conrads T P, Chan K C, Yee C, et al. (2004) A proteomic characterization of the plasma membrane of human epidermis by high-throughput mass spectrometry. J Invest Dermatol 123: 691-699.
40. Foster L J, De Hoog C L, Mann M (2003) Unbiased quantitative proteomics of lipid rafts reveals high specificity for signaling factors. Proc Natl Acad Sci USA 100: 5813-5818.
41. Li N, Mak A, Richards D P, Naber C, Keller B O, et al. (2003) Monocyte lipid rafts contain proteins implicated in vesicular trafficking and phagosome formation. Proteomics 3: 536-548.
42. Li N, Shaw A R, Zhang N, Mak A, Li L (2004) Lipid raft proteomics: analysis of in-solution digest of sodium dodecyl sulfate-solubilized lipid raft proteins by liquid chromatography-matrix-assisted laser desorption/ionization tandem mass spectrometry. Proteomics 4: 3156-3166.
43. von Haller P D, Donohoe S, Goodlett D R, Aebersold R, Watts J D (2001) Mass spectrometric characterization of proteins extracted from Jurkat T cell detergent-resistant membrane domains. Proteomics 1: 1010-1021.
44. Scheiffele P, Rietveld A, Wilk T, Simons K (1999) Influenza viruses select ordered lipid domains during budding from the plasma membrane. J Biol Chem 274: 2038-2044.
45. Nayak D P, Hui E K, Barman S (2004) Assembly and budding of influenza virus. Virus Res 106: 147-165.
46. Jia N, Wang S X, Liu Y X, Zhang P H, Zuo S Q, et al. (2008) Increased sensitivity for detecting avian influenza-specific antibodies by a modified hemagglutination inhibition assay using horse erythrocytes. J Virol Methods 153: 43-48.
47. Gillim-Ross L, Subbarao K (2006) Emerging respiratory viruses: challenges and vaccine strategies. Clin Microbiol Rev 19: 614-636.
48. Wang C C, Chen J R, Tseng Y C, Hsu C H, Hung Y F, et al. (2009) Glycans on influenza hemagglutinin affect receptor binding and immune response. Proc Natl Acad Sci USA 106: 18137-18142.

We claim:

1. A method of preparing an influenza virus-like particle (VLP) for a target influenza strain, the method comprising:
   (1) obtaining a founder Vero cell, wherein the founder Veto cell is stably transfected with a sequence encoding an influenza M1 and a sequence encoding an influenza M2 comprising the amino acid sequence of SEQ ID NO: 7;
   (2) constructing at least one recombinant DNA molecule comprising a sequence encoding an influenza hemagglutinin (HA) and a sequence encoding an influenza neuraminidase (NA), wherein the influenza HA and NA are derived from the target influenza strain;
   (3) transfecting the founder Vero cell from step (1) with the at least one recombinant DNA molecule from step (2) to obtain a co-expression Vero cell, wherein the co-expression Vero cell expresses the influenza M1, M2, HA and NA proteins from one or more inducible expression systems;
   (4) culturing the co-expression Vero cell from step (3) under conditions for expressions of the influenza M1, M2, HA and NA proteins, assembly of the influenza VLP, and secretion of the influenza VLP into culture supernatant of the co-expression Vero cell; and
   (5) isolating the influenza VLP from the culture supernatant of the co-expression Vero cell,
   wherein the influenza VLP comprises the influenza M1, M2, HA and NA proteins and at least one cellular protein of the Vero cell, and the administration of the VLP to a subject induces an immunity against the target influenza strain in the subject.

2. The method according to claim 1, wherein the founder Vero cell is derived from Vero E6 cell.

3. The method according to claim 1, wherein the target influenza strain is a potentially pandemic or seasonal influenza virus strain.

4. The method according to claim 1, wherein
   the at least one recombinant DNA molecule further comprises a sequence encoding a second influenza HA and a sequence encoding a second influenza NA, wherein the influenza HA and the second influenza HA are derived from different influenza virus strains, and the influenza NA and the second influenza NA are derived from different influenza virus strains;
   the co-expression Vero cell is further transfected with the sequences encoding the second influenza HA and the second influenza NA; and
   the culturing step allows expressions of the influenza M1, the influenza M2, the influenza HA, the influenza NA, the second influenza HA and the second influenza NA, and assembly of the VLP comprising the influenza M1, the influenza M2, at least one of the influenza HA and the second influenza HA, and at least one of the influenza NA and the second influenza NA.

5. An influenza virus-like particle (VLP), comprising:
   an influenza M1, an influenza M2 comprising the amino acid sequence of SEQ ID NO:7, an influenza hemagglutinin (HA) and an influenza neuraminidase (NA), wherein the influenza proteins are recombinantly expressed from a Vero cell; and
   at least one cellular protein of the Vero cell.

6. The influenza VLP of claim 5, wherein the Vero cell is Vero E6 cell.

7. The influenza VLP of claim 5, wherein the influenza HA and the influenza NA are derived from one or more potentially pandemic or seasonal influenza virus strains.

8. The influenza VLP of claim 5, further comprising a second influenza HA and a second influenza NA, wherein the influenza HA and the second influenza HA are derived from different influenza virus strains, and the influenza NA and the second influenza NA are derived from different influenza virus strains.

9. The influenza VLP of claim 7, wherein the influenza M1 comprises the amino acid sequence of SEQ ID NO: 6, and the influenza M2 comprises the amino acid sequence of SEQ ID NO: 7.

10. The influenza VLP of claim 5, wherein the at least one cellular protein is selected from the group consisting of clathrin heavy chain 1, spectrin beta, plexin B2, CD109 homolog, prostaglandin F2 receptor negative regulator, Na+/K+-ATPase alpha 1, tumor rejection antigen (gp96) 1 and flotillin I.

11. An immunogenic composition comprising an immunogenic effective amount of the influenza VLP of claim 5 and a pharmaceutically acceptable excipient.

12. The immunogenic composition of claim 11 further comprising an adjuvant.

13. A founder Vero cell being a Vero cell stably transfected with a sequence encoding an influenza M1 and a sequence encoding an influenza M2 comprising the amino acid sequence of SEQ ID NO:7, wherein the expressions of the influenza M1 and M2 proteins in the founder Vero cell are controlled by an inducible expression system.

14. The founder Vero cell of claim 13, wherein the Vero cell is Vero E6 cell.

15. The founder Vero cell of claim 13 further comprising a sequence encoding an influenza hemagglutinin (HA) and a sequence encoding an influenza neuraminidase (NA), wherein the expressions of the influenza M1, M2, HA and NA proteins in the Vero cell are controlled by one or more inducible expression systems.

16. A method of obtaining a founder Vero cell, the method comprising:
   Introducing into a Vero cell a sequence encoding an influenza M1 and a sequence encoding an influenza M2 comprising the amino acid sequence of SEQ ID NO:7; and
   Obtaining the founder Vero cell stably transfected with the sequence encoding the influenza M1 and the sequence encoding the influenza M2 comprising SEQ ID NO:7,
   Wherein expressions of the influenza M1 and M2 proteins in the founder Vero cell are controlled by an inducible expression system.

17. A method of obtaining a co-expression Vero cell, comprising:
   transfecting the founder Vero cell of claim 16 with a sequence encoding an influenza hemagglutinin (HA) and a sequence encoding an influenza neuraminidase (NA) to obtain the co-expression Vero cell, wherein the co-expression Vero cell expresses the influenza M1, M2, HA and NA proteins from one or more inducible expression systems.

18. The method of claim 1, wherein the influenza M1 comprises the amino acid sequence of SEQ ID NO: 6, and the influenza M2 comprises the amino acid sequence of SEQ ID NO: 7.

19. The method of claim 16, wherein the influenza M1 comprises the amino acid sequence of SEQ ID NO: 6, and the influenza M2 comprises the amino acid sequence of SEQ ID NO: 7.

20. The founder Vero cell of claim 13, wherein the influenza M1 comprises the amino acid sequence of SEQ ID NO: 6, and the influenza M2 comprises the amino acid sequence of SEQ ID NO: 7.

* * * * *